US009470563B1

(12) United States Patent
DeVerse

(10) Patent No.: US 9,470,563 B1
(45) Date of Patent: Oct. 18, 2016

(54) METHODS AND SYSTEMS FOR DETECTING FLUIDIC LEVELS AND FLOW RATE AND FLUIDIC EQUIPMENT MALFUNCTIONS

(71) Applicant: Richard Andrew DeVerse, Kailua-Kona, HI (US)

(72) Inventor: Richard Andrew DeVerse, Kailua-Kona, HI (US)

( * ) Notice: Subject to any disclaimer, the term of this patent is extended or adjusted under 35 U.S.C. 154(b) by 0 days.

(21) Appl. No.: 15/090,450

(22) Filed: Apr. 4, 2016

Related U.S. Application Data

(60) Provisional application No. 62/178,140, filed on Apr. 3, 2015.

(51) Int. Cl.
*G01F 1/58* (2006.01)
(52) U.S. Cl.
CPC ..................... *G01F 1/582* (2013.01)
(58) Field of Classification Search
USPC ............... 73/861.11, 170.11, 861.77, 861.79
See application file for complete search history.

(56) References Cited

U.S. PATENT DOCUMENTS

| 4,258,568 A * | 3/1981 | Boetes | B63B 22/18 367/131 |
| 7,267,014 B2 * | 9/2007 | Winter | G01K 17/12 374/E17.01 |
| 8,051,723 B2 * | 11/2011 | Hendey, Sr. | G01F 15/063 73/861.77 |

* cited by examiner

*Primary Examiner* — Jewel V Thompson
(74) *Attorney, Agent, or Firm* — Knobbe, Martens, Olson & Bear, LLP

(57) ABSTRACT

An improved sensor system is provided that monitors and controls a dendritic fluid system. A dendritic fluid system can include artificial components and/or natural components that carry fluid from a source to a destination through a series of paths. The sensor system can include magnetic field sensors, acoustic sensors, encapsulated sensor systems, pressure regulators, and valve controllers to monitor and control the dendritic fluid system. For example, magnetic field sensors, acoustic sensors, and/or pressure regulators can be used to measure the flow of fluid within a dendritic fluid subsystem and/or to detect potential leaks. The encapsulated sensor systems and/or valve controllers can be used to detect fluid levels in a contained system and control valves to adjust the fluid levels in the contained system to a desired level.

20 Claims, 41 Drawing Sheets

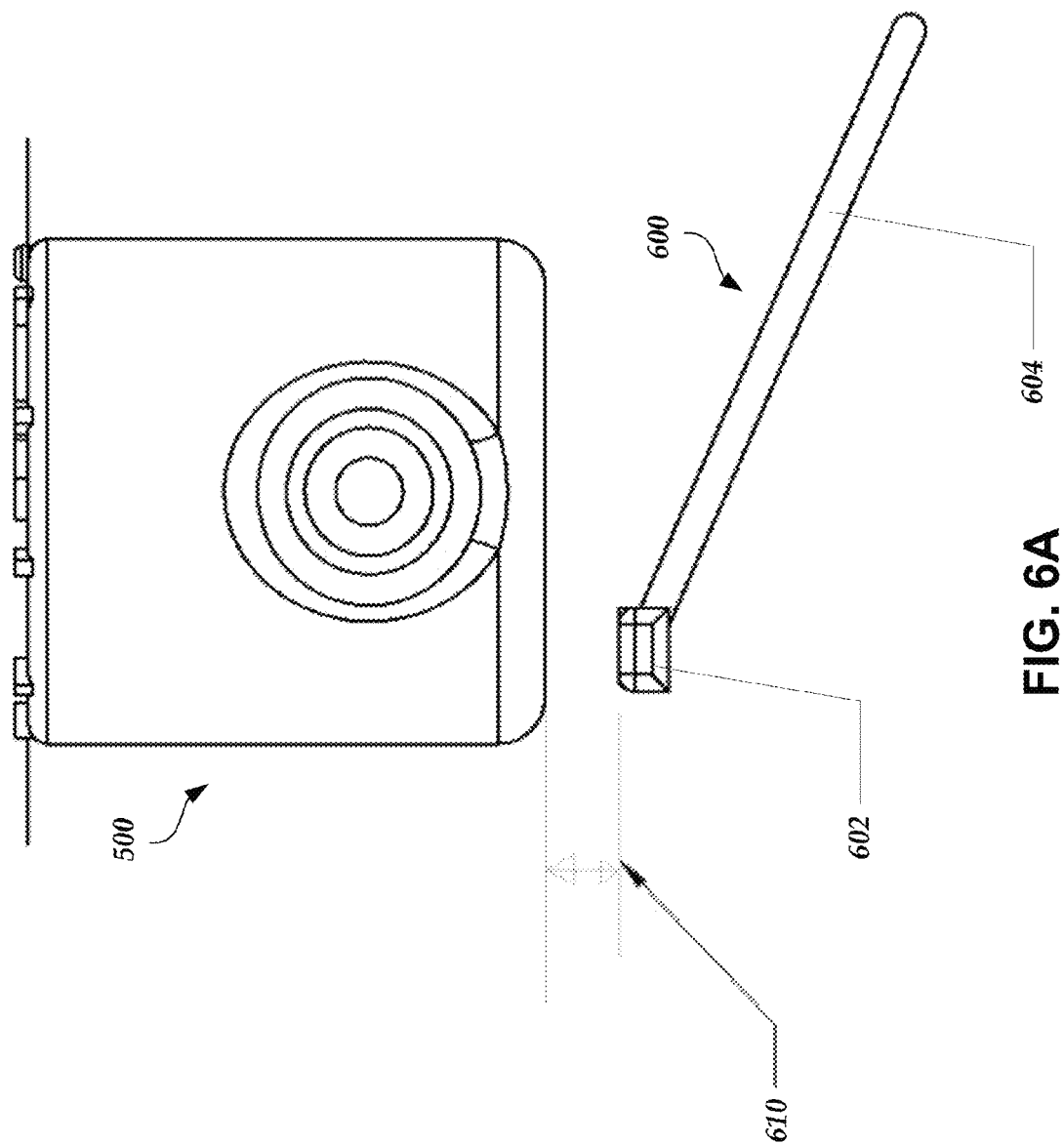

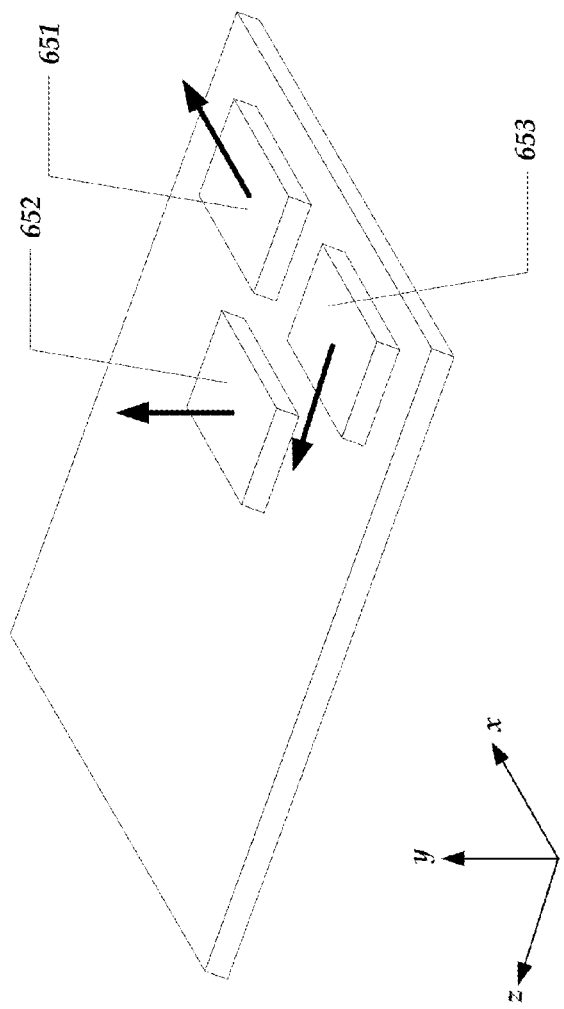

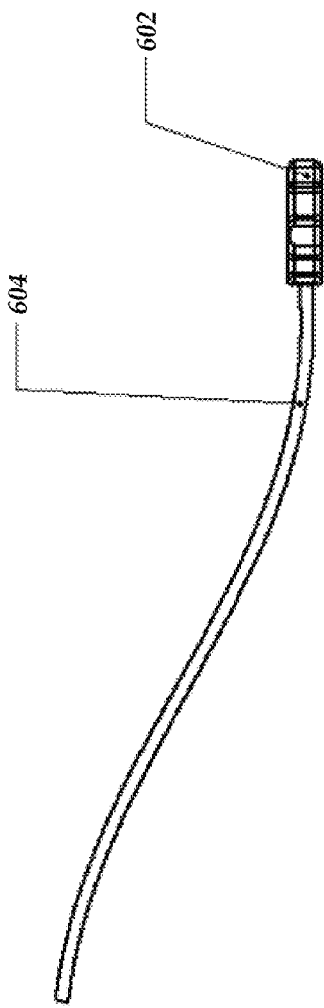
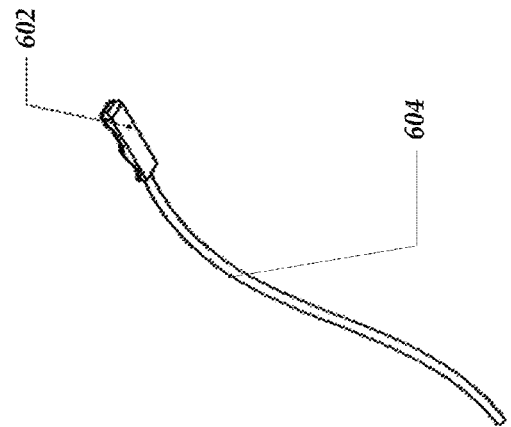
FIG. 7D
FIG. 7E

METHODS AND SYSTEMS FOR DETECTING FLUIDIC LEVELS AND FLOW RATE AND FLUIDIC EQUIPMENT MALFUNCTIONS

CROSS-REFERENCE TO RELATED APPLICATIONS

This application claims priority under 35 U.S.C. §119(e) to U.S. Provisional Application No. 62/178,140, entitled "DEVICES, SENSORS, METHODS AND SYSTEMS FOR IMPROVED SURVEILLANCE" and filed on Apr. 3, 2015, which is hereby incorporated by reference herein in its entirety.

TECHNICAL FIELD

The present disclosure relates generally to the design of printed circuit boards, optical enclosures, and multiplexed signal systems for use in dendritic fluid systems.

BACKGROUND

Wireless radio transmissions can be used to retrieve remotely measurements taken by sensors. Receiving reliable information from individual sensors is often dependent on an appropriate design of the sensor systems, the quality of the individual sensors, and/or the sampling methods implemented by the individual sensors. In addition, the design of the sensor systems can be critical in determining the cost and/or manufacturability of these systems and sensors. Furthermore, the ease of installation and/or maintenance of the systems and sensors and the reliability of the systems and sensors in harsh environments can be key to whether the technology is adopted by the general public.

The use of wireless technology allows for more rapid sensor measurements and allows for an increase in the sampling period. In addition, the use of wireless technology allows for greater temporal precision when simultaneous and/or correlated measurements are desired. However, the sampling and transmitting of sensor data can still be limited by the physical environment, the available bandwidth, and/or the cost of deploying sensor systems. This may be especially true with sensor systems deployed in dendritic fluid systems.

SUMMARY

The systems, methods, and devices described herein each have several aspects, no single one of which is solely responsible for its desirable attributes. Without limiting the scope of this disclosure, several non-limiting features will now be discussed briefly.

One aspect of the disclosure provides a magnetic field sensor comprising a head, a cable, and a transceiver. The head comprises a first sensor, a second sensor, and a third sensor, where the first sensor is oriented to measure a magnetic field generated by a water meter along a first axis, where the second sensor is oriented to measure the magnetic field along a second axis different from the first axis, where the third sensor is oriented to measure the magnetic field along a third axis different from the first axis and the second axis, and where the head is positioned a first distance from the water meter. The cable comprises a first end and a second end, where the first end of the cable is coupled with the head, where the cable is configured to receive a first measurement measured by the first sensor, a second measurement measured by the second sensor, and a third measurement measured by the third sensor, and where the cable is further configured to transport the first measurement, the second measurement, and the third measurement to the second end of the cable. The transceiver is coupled to the second end of the cable, where the transceiver is configured to wirelessly transmit the first measurement, the second measurement, and the third measurement received from the second end of the cable to a remote server over a network.

The magnetic field sensor of the preceding paragraph can have any sub-combination of the following features: where a front surface of the head is positioned the first distance from the water meter; where a left surface of the head is positioned the first distance from the water meter; where the water meter comprises a magnet that rotates about a first axis, and where the head is positioned in a plane that is generally transverse to the first axis; where the third sensor measures a rate of change of a magnetic field generated by the magnet in the water meter along the third axis, and where a faulty meter is detected if the rate of the change of the magnetic field generated by the magnet in the water meter along the third axis is greater than a threshold value; where the first sensor is a hall-effect sensor; where the first sensor is positioned in a first plane, and where the head further comprises a ferrite pole positioned in a second plane coplanar with the first plane; where the first plane is positioned above the second plane; where the first plane is positioned below the second plane; where the head further comprises an amplifier configured to amplify the first measurement measured by the first sensor; where the head further comprises an analog-to-digital circuit (ADC) configured to digitize the amplified first measurement, and where the ADC is further configured to transmit the digitized amplified first measurement to the first end of the cable; where the first sensor is configured to measure a rate of change of the magnetic field generated by the water meter along the first axis, and where the second sensor is configured to measure a rate of change of the magnetic field generated by the water meter along the second axis; where the head comprises a protective enclosure that protects the first sensor, the second sensor, and the third sensor from an environment exterior to the head; where a top of the head comprises a first depression for coupling the device with a pipe using a mounting component; where the mounting component is a plastic tie; where the magnetic field sensor further comprises a temperature sensor configured to measure a current temperature; and where the head further comprises a microcontroller configured to adjust the first measurement measured by the first sensor based on the measured current temperature.

Another aspect of the disclosure provides a magnetic field sensor comprising a head, a cable, and a transceiver. The head comprises a multi-axis sensor, where the multi-axis sensor is configured to measure a change in a magnetic field generated by a fluid meter along a first axis, along a second axis that is different from the first axis, and along a third axis that is different from the first axis and the second axis, and where the head is positioned a first distance from the fluid meter. The cable comprises a first end and a second end, where the first end of the cable is coupled with the head, where the cable is configured to receive a first measurement measured by the multi-axis sensor, and where the cable is further configured to transport the first measurement to the second end of the cable. The transceiver is coupled to the second end of the cable, where the transceiver is configured to associate with a network and transmit the first measurement received from the second end of the cable to a remote server via the network.

The magnetic field sensor of the preceding paragraph can have any sub-combination of the following features: where the multi-axis sensor is further configured to measure a magnitude of the magnetic field generated by the fluid meter and an orientation of the magnetic field generated by the fluid meter; and where the fluid meter comprises one of a liquid meter used to measures a rate of flow of a liquid through a fixed location or a gas meter used to measure a rate of flow of a gas through the fixed location.

BRIEF DESCRIPTION OF THE DRAWINGS

FIG. 6A illustrates a top view perspective of a magnetic field sensor that measures a change in a magnetic field as caused by the rotation of the magnet in the fluid meter of FIG. 5.

FIG. 6B illustrates a position of the multi-axis sensors relative to each other in the head of FIG. 6A.

FIG. 7D illustrates a top perspective view of the head and the cable of the magnetic field sensor of FIG. 6A.

FIG. 7E illustrates a bottom perspective view of the head and the cable of the magnetic field sensor of FIG. 6A.

DETAILED DESCRIPTION OF SPECIFIC EMBODIMENTS

Overview

Figure 1:
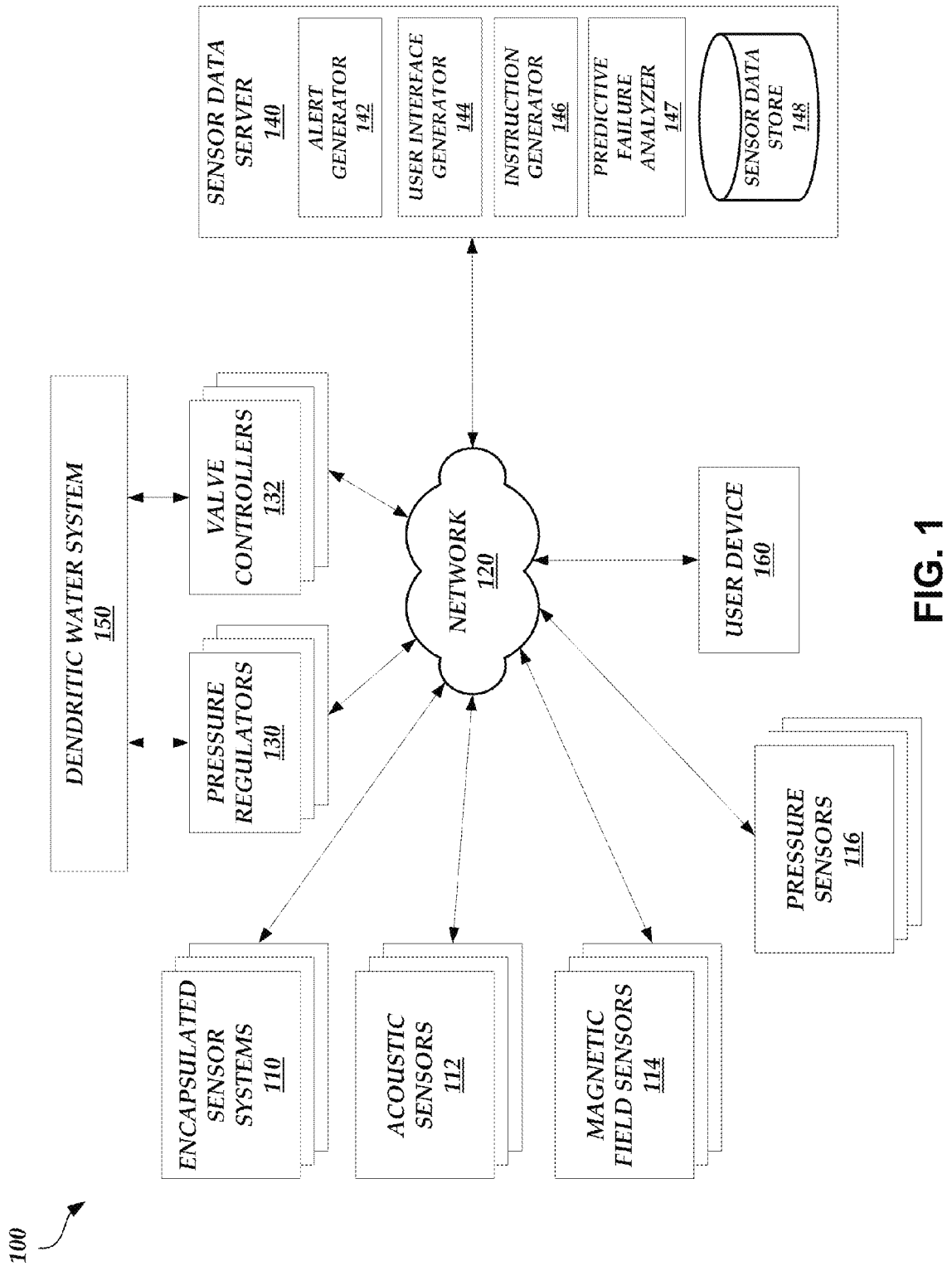
FIG. 1 illustrates a block diagram showing the various components of a sensor system for dendritic water systems.

As described above, the sampling and transmitting of sensor data by sensor systems deployed in dendritic fluid systems can be limited by the physical environment, the available bandwidth, and/or the cost of deploying such sensor systems. For example, fluids are generally highly absorbent of radio frequency energy used for the wireless transmission of information and can therefore disrupt transmissions. Thus, it may be important to optimize the transmission of sensor data and/or the sensitivity of the individual sensors to ensure that the sensor systems can be widely used.

In addition, dendritic fluid systems generally include a single point sensor to measure the movement of fluid into or out of the dendritic fluid system. In some cases, there are two sensors providing two points of measurement. The sensors take discrete physical measurements of the movement of some fluid passed a meter based on the movement of physical parts in the meter (e.g., a magnet) or based on the movement of light or sound waves through the meter. Typically, if one more than one sensor is installed, the sensors are read manually and sequentially. There can be limits to the type of data these sensors can measure and many such sensors require homogenous materials for precise and accurate measurements across all sensors.

Furthermore, designers often make difficult choices when selecting sensors to include in a sensor system, such as one that is deployed within a dendritic fluid system. Generally, designers consider sensor cost, sensor type, sensor placement, sensor availability, available bandwidth, technical expertise, and/or other restrictions when making these selections. In some cases, designers also consider potential maintenance given that some sensor systems require frequent maintenance, which can be problematic if maintenance is costly and/or there are few skilled maintenance workers available to conduct the periodic maintenance. In some cases, such as with decorative water feature systems (e.g., fountains, waterfalls, etc.), designers may consider aesthetics or potential harm to human or animal swimmers when selecting sensors to deploy.

Ideally, a sensor system is low cost, includes high resolution sensors, and includes sensors that can take measurements over a wide range of values. However, compromises are often made given the design choices described above. For example, many high resolution sensors have a high time resolution (e.g., the ability to take measurements at a high frequency) and/or high sensitivity to changes (e.g., the ability to detect small changes in measurements). High resolution sensors that have a high sensitivity to change, however, often can only take measurements over a small range of values. Conversely, low resolution sensors often are not sensitive to small changes in measurements, but can take measurements over a wide range of values. High resolution sensors are also generally more expensive than low resolution sensors.

These factors are especially important for designers when selecting sensors to deploy in a dendritic fluid system. Thus, it can be advantageous to simplify and make more efficient the deployment of sensor systems within dendritic fluid systems. Modifications to sensor design, improvements to sensor sampling techniques, and/or improvements can facilitate the simplification and efficiency in deployment. In fact, such modifications and improvements can improve the performance of the sensor system without an increase in costs and/or result in a same level of performance at a lower cost.

Accordingly, described herein is an improved sensor system that monitors and controls a dendritic fluid system. A dendritic fluid system can include artificial components (e.g., pipes, valves, etc.) and/or natural components (e.g., rivers, arteries, veins, etc.) that carry fluid from a source to a destination through a series of paths. For example, a dendritic fluid system can be a human vascular system, a fluidic distribution system within a chemical analysis apparatus, pipes in a refinery, a municipal water distribution system, an irrigation system, a swimming pool, a lake, a water reservoir, and/or the like. In the example of the municipal water distribution system, the municipal water distribution system can include pipes, valves, and/or other components that carry water from a main pipe (e.g., outside a physical structure) to bathtubs, sinks, refrigerators, toilets, washing machines, sprinklers, pools, and/or any other appliances or systems that use water within or outside a physical structure.

The sensor system can include magnetic field sensors, acoustic sensors, encapsulated sensor systems, pressure regulators, and valve controllers to monitor and control the dendritic fluid system. For example, magnetic field sensors, acoustic sensors, and/or pressure regulators can be used to measure the flow of fluid within a dendritic fluid subsystem and/or to detect potential leaks. The encapsulated sensor systems and/or valve controllers can be used to detect fluid levels in a contained system (e.g., a pool) and control valves to adjust the fluid levels in the contained system to a desired level. The sensor system is described in greater detail below with respect to FIGS. 1-36.

While the sensor system is described below in reference to a specific type of dendritic fluid system, namely a dendritic water system, and leaks that occur in dendritic fluid systems, this is merely for illustrative purposes and is not meant to be limiting. The sensor system described herein can be used to monitor and/or control a dendritic fluid system that handles any fluid (e.g., liquid, gas, plasma, plastic solids, etc.). Furthermore, the techniques described herein can apply to process control, inventory control, heating ventilation and air conditioning (HVAC) systems, fuels, chemicals, liquids, solids, and/or any materials that are transported in container systems. This can include the transport of materials by rail, fleet truck, boat, river, ocean, and/or by land or any other quantized or statistically quantized container transport mechanism where the rate of flow can be metered or measured. Product flow through systems, such as rail or fleet, can be treated in the same manner using similar techniques adjusted for system attributes and/or weightings.

Sensor System

FIG. 1 illustrates a block diagram showing the various components of a sensor system 100 for dendritic water systems. As illustrated in FIG. 1, the sensor system 100 may include encapsulated sensor systems 110, acoustic sensors 112, magnetic field sensors 114, pressure sensors 116, pressure regulators 130, valve controllers 132, a sensor data server 140, a dendritic water system 150, and a user device 160.

The dendritic water system 150 can be a water distribution and control system that routes water from a main line to various appliances, fixtures, swimming pools, ponds, fountains, garden features, and/or other components within or exterior to a building. The dendritic water system 150 can include pipes, valves, and/or other components to route the water. One or more acoustic sensors 112, one or more magnetic field sensors 114, and/or one or more pressure sensors 116 can be deployed throughout the dendritic water system 150 to monitor fluid flow and/or to detect leaks.

For example, portions of the dendritic water system 150 may be difficult to monitor for leaks or other losses of the fluid being transported. Pipes, valves, or other components may be hidden behind walls, under slabs, underground, or in remote locations that are otherwise difficult to access. Furthermore, even if the location of a leak can be accessed, some dendritic water systems do not have shutoff valves that completely stop the flow of water. In some cases, leaks can be constant and expensive and the costs can increase with time. In fact, by the time some leaks become visible, significant damage may already have occurred. Thus, appropriate monitoring technology may be beneficial in addressing leaks before the costs soar, especially in situations in which the dendritic water system 150 includes difficult to access regions. Accordingly, the acoustic sensors 112, the magnetic field sensors 114, and/or the pressure sensors 116 are provided to assist with the detection of leaks, even in difficult to access portions of the dendritic water system 150. Furthermore, the pressure regulators 130 and/or the valve controllers 132 can be used to shutoff water flow in problematic areas, as discussed in greater detail below.

In some cases, at least a portion of the dendritic water system 150 includes a contained system, such as a swimming pool or a bathtub. Leaks can occur in these contained systems as well. Thus, the encapsulated sensor system 110 can be deployed near a surface level of the contained system (e.g., a plane in which water interfaces with air or other gasses) to monitor for leaks and/or to cause an increase in the fluid level in the contained system if a leak is detected.

The sensor data server 140 may be a remote server that receives and stores measurements captured by the encapsulated sensor system 110, the acoustic sensors 112, the magnetic field sensors 114, and/or the pressure sensors 116 via a network 120. The sensor data server 140 may also generate and transmit commands to the pressure regulators 130 and/or the valve controllers 132 via the network 120 to control the operation of the dendritic water system 150.

The sensor data server 140 may be implemented as a special-purpose computer system having logical elements. In an embodiment, the logical elements may comprise program instructions recorded on one or more machine-readable storage media. Alternatively, the logical elements may be implemented in hardware, firmware, or a combination thereof. In one embodiment, the sensor data server 140 may be implemented in a Java Virtual Machine (JVM) that is executing in a distributed or non-distributed computer system. In other embodiments, the sensor data server 140 may be implemented as a combination of programming instructions written in any programming language (e.g. C++, Visual Basic, Python, etc.) and hardware components (e.g., memory, CPU time) that have been allocated for executing the program instructions.

The sensor data server 140 may include various modules. For example, the sensor data server 140 may include an alert generator 142, a user interface generator 144, an instruction generator 146, a predictive failure analyzer 147, and a sensor data store 148. In an embodiment, the alert generator 142, the user interface generator 144, the instruction generator 146, and the predictive failure analyzer 147 are each implemented as executable code modules that are stored in the memory of, and executed by the processor(s) of, the sensor data server 140. The alert generator 142, the user interface generator 144, the instruction generator 146, and the predictive failure analyzer 147 may also be implemented partly or wholly in application-specific hardware.

The alert generator 142 may be configured to generate alerts to notify users of leaks, equipment failures, and/or other such issues. For example, the alert generator 142, upon receiving a notification that an alert is to be generated, may generate the alert with the appropriate information. In an embodiment, the alert and/or a notification of the alert is automatically transmitted by the alert generator 142 to the user device 160 to inform a user associated with the alert and/or notification. The alert and/or notification can be transmitted at the time that the alert and/or notification is generated or at some determined time after generation of the alert and/or notification. When received by the user device 160, the alert and/or notification can cause the user device 160 to display the alert and/or notification via the activation of an application on the user device 160 (e.g., a browser, a mobile application, etc.). For example, receipt of the alert and/or notification may automatically activate an application on the user device 160, such as a messaging application (e.g., SMS or MMS messaging application), a standalone application (e.g., a leak detection application), or a browser, for example, and display information included in the alert and/or notification. If the user device 160 is offline when the alert and/or notification is transmitted, the application may be automatically activated when the user device 160 is online such that the alert and/or notification is displayed. As another example, receipt of the alert and/or notification may cause a browser to open and be redirected to a login page generated by the sensor data server 140 so that the entity can log in to the sensor data server 140 and view the alert and/or notification. Alternatively, the alert and/or notification may include a URL of a webpage (or other online information) associated with the alert and/or notification, such that when the user device 160 (e.g., a mobile device) receives the alert, a browser (or other application) is automatically activated and the URL included in the alert and/or notification is accessed via the Internet.

The user interface generator 144 can be configured to generate user interface data that causes a device, such as the user device 160, to display a user interface. The user interface can be populated with information generated by the alert generator 142 and/or the predictive failure analyzer 147. In addition, the user interface generator 144 can generate graphs of sensor data or processed sensor data stored in the sensor data store 148 and include such graphs in the user interface data. The user interface data can be transmitted to the user device 160 via the network 120 for display.

The instruction generator 146 can be configured to generate instructions for controlling the pressure regulators 130 and/or the valve controllers 132. For example, the instruction generator 146 can generate an instruction in response to the results of an analysis performed by the alert generator 142 and/or the predictive failure analyzer 147 indicating that the operation of a pressure regulator 130 or valve controller 132 should be adjusted. The instruction generator 146 can transmit the instruction to the pressure regulators 130 and/or the valve controllers 132 via the network 120.

The predictive failure analyzer 147 can be configured to identify the failure or malfunction or predict the failure or malfunction of appliances, fixtures, swimming pools, ponds, fountains, garden features, and/or other components coupled with the dendritic water system 150. Upon identifying or predicting the failure or malfunction of such components, the predictive failure analyzer 147 can instruct the alert generator 142 to generate an alert for notifying the user via the user device 160 of the failure or malfunction.

In some embodiments, the predictive failure analyzer 147 generates an instruction to shut off a valve. For example, the predictive failure analyzer 147 can generate an instruction to shut off a valve if the valve corresponds to a location in which a leak is predicted to occur in the future or is identified as occurring in the present. Thus, the predictive failure analyzer 147 may help avert major damage to the location at which the leak is present or may be present. The instruction can be transmitted to the appropriate valve controller 132 via the network 120.

In some embodiments, the predictive failure analyzer 147 generates an instruction to adjust the water pressure. For example, the predictive failure analyzer 147 may store a list of water pressure values that, if reached, can cause damage to portions of the dendritic water system 150. If the acoustic sensors 112 and/or the pressure sensors 116 indicate that such a water pressure level has been reached, the predictive failure analyzer 147 can transmit an instruction to the pressure regulator 130 to reduce the water pressure. In further embodiments, if the transmitted instruction does not result in the reduction of the water pressure (e.g., because the pressure regulator 130 unknowingly failed), the predictive failure analyzer 147 can instruct the alert generator 142 to generate an alert for display in the user device 160 such that the user is notified that a potential pressure regulator 130 failure has occurred and to inspect the premises.

As an example, the predictive failure analyzer 147 can predict the failure of a valve using trend analysis. For example, the predictive failure analyzer 147 can analyze a difference between a time that a signal is transmitted to a valve to shut off and a time that fluid stops passing through the valve. The time data can be provided by various sensors, such as the acoustic sensors 112, the magnetic field sensors 114, and/or the pressure sensors 116. Over time, this difference can be tracked and the predictive failure analyzer 147 can use trend analysis techniques to determine when the valve will fail (e.g., the valve may be considered to have failed if the difference in time is greater than a threshold value). For example, as a valve ages, portions of the valve may become out of tolerance or obstructed or damaged by debris or micro-fine particles. Typically, a valve should shut off within a few seconds of a time that a signal is sent to shut off the valve and the valve should shut off abruptly once the shutoff procedure begins. The flow of fluid through a valve may induce pressure variations that create standing waves. The standing waves can be measured by, for example, an acoustic sensor 112 or a pressure sensor 116. A magnitude and/or phase of a standing wave may correspond to a particular valve with a particular fluid pressure and a particular rate of fluid flow. If the predictive failure analyzer 147 identifies a change in the standing wave, this may indicate a change in the hydrodynamic shutoff function of the valve. In particular, age of the valve or obstructions identified above can cause the hydrodynamic shutoff function of the valve to change. The predictive failure analyzer 147 can track these changes in the hydrodynamic shutoff function and use trend analysis to determine when the change will exceed acceptable levels. In some embodiments, the predictive failure analyzer 147 uses data acquired from sensors associated with different valves to predict the failure of a single valve (e.g., the predictive failure analyzer 147 can use data from valves in close proximity to the single valve).

The sensor data store 148 can store sensor data measured by the encapsulated sensor systems 110, the acoustic sensors 112, the magnetic field sensors 114, and/or the pressure sensors 116. The data stored may include the physical measurements, a time that the measurements are taken, and/or a sensor identifier identifying the individual sensor from which the data originates. The sensor data store 148 can also store the results of any analyses performed by the alert generator 142, the instruction generator 146, and/or the predictive failure analyzer 147. While the sensor data store 148 is illustrated as being stored in the sensor data server 140, this is not meant to be limiting. The sensor data store 148 can be external to the sensor data server 140.

In an embodiment, the magnetic field sensors 114 are configured to measure the intensity (e.g., magnitude) and orientation of a change in magnetic fields caused by the rotation of a magnet in a fluid meter, such as a water meter, at a specific time instant. The magnetic field sensors 114 can measure the magnitude and orientation along three axes or dimensions. For example, the magnetic field sensors 114 can each include one or more multi-axis sensors that each measure magnetic field change magnitude and orientation along one axis. The magnetic field sensors 114 can also include a transceiver coupled to the multi-axis sensors for transmitting the information measured by each of the multi-axis sensors and the time of the measurement to the sensor data server 140 via the network 120. The structure of the magnetic field sensors 114 is described in greater detail below with respect to FIGS. 6A-9.

The pressure regulators 130 can adjust and/or control water pressure in the dendritic water system 150. For example, a building with a 2" main water supply line can be metered outside of the building. The main water supply line then can be regulated by a first pressure regulator 130. The main water supply line can then enter the building through the basement under the street level and be metered once again by a second pressure regulator 130. The second pressure regulator 130 can regulate the water pressure to a lower pressure for distribution throughout the building. Several more pressure regulators 130 can be located throughout the building given the fact that the top floors of the building may not receive as much water pressure as the lower floors due to the weight of the water column.

In an embodiment, a pressure regulator 130 includes one or more pressure flow and acoustical sensors. In other embodiments, an acoustic sensor 112 and/or a pressure sensor 116 is coupled with an exterior of the pressure regulator 130 and/or a location near the exterior of the pressure regulator 130. The pressure regulator 130 can include a motorized control (e.g., a screw mechanism) that automatically adjusts the water pressure (e.g., between 0 PSI and line pressure) based on commands received from, for example, the sensor data server 140 via the network 120. For example, when the motorized control is in a fully extended position, the flow of water may be stopped (e.g., 0 PSI), and when the motorized control is in a fully depressed position, the flow of water may continue at line pressure. The pressure flow and acoustic sensor(s) in the pressure regulators 130, the external acoustic sensor 112, and/or the external pressure sensor 116 can measure initial pressure waves and/or reflected waves and resonances within the dendritic water system 150 at a specific time instant. Such information can be transmitted to the sensor data store 148 via the network 120 for storage.

In some embodiments, the pressure regulators 130 include a relay switch and a microcontroller unit that executes a set of instructions for detecting leaks. For example, the pressure regulators 130 can include memory that stores the instructions and data indicating expected pressure differentials. A first expected pressure differential may be a stimulus response function represented by a sequence of pressure measurements taken as a pressure regulator 130 reduces pressure to 0 PSI and a second expected pressure differential may be a stimulus response function represented by a sequence of pressure measurements taken as a pressure regulator 130 increases pressure from 0 PSI to normal operation. The first and second pressure differentials can be based on historical pressure measurements as the pressure regulator 130 is modulated (e.g., adjusted from 0 PSI to normal operation and vice-versa). The instructions, when executed by the microcontroller, may cause the microcontroller to compare a currently measured pressure differential (e.g., a stimulus response function represented as a sequence of pressure measurements taken as the pressure regulator 130 adjusts the pressure) with the stored first or second pressure differential. If the currently measured pressure differential is calculated when the pressure regulator 130 is adjusted to 0 PSI and the measured pressure differential varies from the stored first pressure differential by a threshold amount (e.g., an absolute value of each stimulus response function differs by a threshold amount, a Fourier transform of each response function is taken and the modulus of each Fourier transform differs by a threshold amount, etc.), then the microcontroller may determine that there is a leak. Likewise, if the currently measured pressure differential is calculated when the pressure regulator 130 is adjusted to normal operation and the measured pressure differential varies from the stored second pressure differential by a threshold amount (e.g., an absolute value of each stimulus response function differs by a threshold amount, a Fourier transform of each response function is taken and the modulus of each Fourier transform differs by a threshold amount, etc.), then the microcontroller may determine that there is a leak. If the executed instructions indicate that a leak is detected, a close signal may be transmitted by the microcontroller to the relay switch. The relay switch may allow current to flow to the motorized control in a manner that causes the motorized control to adjust into the fully extended position, thereby shutting off the water flow.

In one example, a single pressure regulator 130 can be installed at the output of a water meter at a location where the dendritic water system 150 enters a large multi-use building. This pressure regulator 130 can be enclosed with a brass housing and include a pressure sensor and a flow sensor. The pressure regulator 130 can include a motorized control to control pressure from 0 PSI to line pressure, as described above. The pressure regulator 130 may also include an energy scavenging system that charges and recharges a super capacitor and/or a battery. For example, the flow of water may induce cavitation or vibrations and this turbulent energy can be transferred to storage. Other energy scavenging systems can alternatively be included in the pressure regulator 130.

The valve controllers 132 can be configured actuate valves. For example, the valves can control water flow, chemical substance dispersion (e.g., chlorine, salt, etc.), water pressure, and/or the like. The valve controllers 132 may include light emitting diodes (LEDs) that indicate a status of operation. For example, an LED ma indicate when a valve controlled by the valve controller 132 is active.

In addition, the acoustic sensors 112 can detect vibrations within the dendritic water system 150 caused by the flow of fluid (e.g., vibrations within apertures of a pressure regulator 130). For example, the acoustic sensor 112 can be located on a pressure regulator 130 at a first location and can detect vibrations at the first location at a specific time instant and transmit the vibration and time information to the sensor data server 140. The intensity of the vibrations may be correlated with a rate of fluid flow through the pressure regulator 130. If the intensity of the vibrations indicates that the rate of fluid flow is greater than a threshold value (or less than another threshold value), the instruction generator 146 can generate an instruction to reduce (or increase) the pressure and transmit the instruction to the appropriate pressure regulator 130 (e.g., the pressure regulator 130 to which the acoustic sensor 112 is attached). The pressure regulator 130 can then use the motorized control to perform the appropriate adjustment.

Similarly, the detected vibrations can indicate that a leak is present. For example, the signature of the vibration may indicate a location of the leak and/or the type of leak. The predictive failure analyzer 147 can compare the signature of the vibration with known signatures to identify the leak location and/or leak type. The leak location and/or leak type can be displayed to the user via the user device 160. In addition, based on the identified leak location and/or leak type, the predictive failure analyzer 147 can generate information for display to the user via the user device 160 that indicates a part corresponding to the leak and/or can generate a service order for submission by the user to order a new part corresponding to the leak.

In an embodiment, the pressure level measurements captured by the pressure sensors 116 can indicate the presence of a leak. For example, water pressure may drop if a leak is present. The ratio of a pressure drop over elapsed time as measured by a pressure sensor 116 can indicate the rate of the leak or water flow into and out of the dendritic water system 150. The predictive failure analyzer 147 can use the pressure fluctuation over time data to derive additional data, such as leak location, leak position relative to earth elevation, whether the leak is in a horizontal section or vertical section of a pipe, and/or the like. Information such as the pipe composition and/or the pipe diameter can also be determined by the predictive failure analyzer 147 using the pressure fluctuation over time data. The predictive failure analyzer 147 can also perform an analysis of the pressure fluctuation over time data (e.g., a Fourier analysis) to generate the characteristic response function of the portion of the dendritic water system 150 corresponding to the location of the pressure sensor 116, including a location and magnitude of the leak or other transport dynamics of that portion of the dendritic water system 150.

The pressure regulators 130 and/or the valve controllers 132 can include an energy storage device for providing operational power. For example, the energy storage device can be a battery, a dynamo, and/or another modulated energy capture device. The energy storage device can provide power to the motorized control of the pressure regulators 130 and/or the valve controllers 132.

Thus, the sensor data server 140 can receive fluid flow data from the magnetic field sensors 114 and fluid pressure data from the acoustic sensors 112, the pressure sensors 116, and/or the pressure regulators 130 themselves.

The encapsulated sensor system 110 can be configured to measure a level of a liquid-gas interface in a contained system within the dendritic water system 150. For example, the encapsulated sensor system 110 can be positioned on the wall of a swimming pool at the water line, where a portion of the encapsulated sensor system 110 is above the water line and a portion of the encapsulated sensor system 110 is below the water line. As described in greater detail below with respect to FIGS. 12-30, the encapsulated sensor system 110 can include sensors that detect a current water line in the containment system. If the detected water line drops below a threshold level, the encapsulated sensor system 110 can transmit a signal to a valve controller 132 via the network to instruct the valve controller 132 to open (e.g., actuate) a valve (e.g., turn the valve solenoid circuit on) to allow more water to enter the containment system. Alternatively, the encapsulated sensor system 110 can transmit an indication of a level of the water line to the sensor data server 140. The sensor data server 140 can analyze the indicated level and determine whether to then instruct the valve controller 132 to open a valve to allow more water to enter the containment system via the network 120 (and transmit such an instruction if the determination is made to open the valve). The signal instructing the valve controller 132 to actuate the valve may specify a time period for which the valve should be actuated. The time period may be set regardless of the level of the water line. In further embodiments, the encapsulated sensor system 110 can measure a temperature of the water and/or the air and provide these measurements to the sensor data server 140.

The encapsulated sensor systems 110, the acoustic sensors 112, the magnetic field sensors 114, and/or the pressure sensors 116 may include one or more batteries for powering the devices, a temperature sensor for temperature calibration, and/or may incorporate a randomized temporal pattern technique for sensing based on compressive sensing techniques.

The user device 160 can include a wide variety of computing devices, including personal computing devices, terminal computing devices, laptop computing devices, tablet computing devices, electronic reader devices, mobile devices (e.g., mobile phones, media players, handheld gaming devices, etc.), wearable devices with network access and program execution capabilities (e.g., "smart watches" or "smart eyewear"), wireless devices, set-top boxes, gaming consoles, entertainment systems, televisions with network access and program execution capabilities (e.g., "smart TVs"), and various other electronic devices and appliances. The user device 160 may execute a browser application or another application (e.g., a leak detection application that allows the user to monitor and/or control valve and water meter data) to communicate with the sensor data server 140. The user device 160 may prompt a user to enter a username and/or password before access to the data provided by the sensor data server 140 is granted. Different users may have different permissions such that some users (e.g., property owners) are allowed to, for example, override various setpoint shutoffs, run special tests, turn on or off hoses, faucets, and/or the like, while other users (e.g., service providers) are not.

In an embodiment, the network 120 includes any communications network, such as the Internet. The network 120 may be a wired network (e.g., RS-232, Ethernet, etc.), a wireless network (e.g., a Bluetooth network, an IEEE 802.11 protocol network, a cellular network, etc.), or a combination of the two. For example, network 120 may be a local area network (LAN) and/or a wireless area network (WAN).

In other embodiments, not shown, the sensor system 100 or any of the individual sensors 110, 112, 114, and/or 116 can include energy scavenging systems (e.g., MEMS sensors, photovoltaic cells, gyroscopes for detecting motion, etc.), energy storage systems, moisture sensors, mass sensors, surface level sensors, mold growth sensors, humidity sensors, fluid clarity sensors (e.g., water clarity sensors), temperature sensors, and/or other sensors to aid in the measurement of fluid flow rate in the dendritic water system 150. For example, temperature sensors can be multiplexed in concert or separate from the water valve modulations such that an amount of energy use in each subsystem of the dendritic water system 150 is known. As an example, if it is known that chilled water is flowing into a subsystem and the temperature sensor measures a temperature drop of that water volume, then the amount of energy left in the subsystem and/or dendritic water system 150 may be known. This information may be useful in managing cooling costs in dendritic water systems 150. In addition, energy losses can be detected early and mitigated such that operational costs can be distributed to individual users in a more equitable fashion. As another example, temperature sensors and moisture sensors can be used in conjunction with an internal clock to estimate when conditions may be conducive to mold growth. This information can be relayed to the sensor data server 140 for notifying a user via the user device 160.

In other embodiments, not shown, the sensor system 100 can include one or more relay devices. In some cases, one of more of the sensors 110, 112, 114, and/or 116 may be out of range of the network 120. Thus, relay devices that are configured to communicate with the network 120 can be deployed throughout the dendritic water system 150 such that the out of range sensors can communicate with a relay device and the relay device can forward received messages to the sensor data server 140 via the network 120. Similarly, the relay devices can receive messages from the sensor data server 140 to forward to otherwise out of range sensors.

Generally, to receive better sensor measurements, a large number of encapsulated sensor systems 110, acoustic sensors 112, magnetic field sensors 114, and/or pressure sensors 116 can be deployed in the sensor system 100. However, using the techniques described herein, a fewer number of encapsulated sensor systems 110, acoustic sensors 112, magnetic field sensors 114, and/or pressure sensors 116 can be deployed while still achieving these better sensor measurements.

For example, a structure may include 10 appliances or fixtures that use water. Normally, to identify water use by each of the appliances or fixtures, the structure would need to be populated with 10 sensors, one for each appliance or fixture. However, the techniques described herein can be used such that the water usage of each of the 10 appliances or fixtures can be determined using fewer than 10 sensors.

As another example, a sensor, such as the magnetic field sensor 114, may need to achieve a signal to noise ratio (SNR) of 100 to 1 in a certain application. To achieve this SNR, the magnetic field sensor 114 may be constructed of fine grade of sensor material that has less noise than other comparable materials when a measurement is taken. A second sensor material may be available that is cheaper than the fine grade of sensor material, but the second sensor material may introduce more noise when a measurement is taken. In this case, the second sensor material may result in an SNR of 5 to 1. Using the techniques described herein, the sensor performance of a sensor constructed with the second sensor material can be increased (e.g., by 14 to 1) if all other parts remain the same. Thus, a less expensive sensor can be used to achieve a desired SNR.

As another example, the sensors 110, 112, 114, and/or 116 can be installed without any modification to the dendritic water system 150. For example, no pipes need to be cut, added, or otherwise modified in order to deploy the sensors 110, 112, 114, and/or 116. Thus, installation costs are significantly reduced as compared to other methods that may require modifications to the dendritic water system 150.

Accordingly, the cost advantages provided by the techniques described herein can be additive in that fewer sensors can be deployed to achieve the desired measurements and the sensors that are deployed can be constructed of materials that are cheaper than other materials normally used to achieve a desired SNR.

Sensor Sampling Using Hadamard Techniques

Often, water meters used to measure water volume for billing purposes only measure the bulk flow of water into a dendritic water system. The dendritic water system, though, may include a number of subsystems (e.g., different apartments in an apartment building). Each of these subsystems may be isolated individually by shutoff valves. Thus, in typical tests of a dendritic water system, all valves are shut off and then are each valve is turned on one at a time to test for water flow.

For example, a single meter may be present on the main water supply line that feeds a building. This meter may not be capable of determining a volume of less than 100 gallons. If this meter was monitored for leak detection and all valves were shut off, 100 gallons may pass through the meter before a leak could be identified and an action taken to mitigate damages due to water spillage and/or loss. Instead, it may be desirable to detect the leak after a smaller quantity of water has passed through the meter (e.g., only 10 gallons), where detection of the leak causes an automatic valve shut off procedure in the subsystem to limit damages. The automatic shut off of a valve in a particular subsystem (and not other subsystems in which a leak is not present) may be important for several reasons. Fire prevention subsystems (e.g., sprinkler systems) may rely on the availability of water and could be at risk of being ineffective if the entire dendritic water system is shut off to address a leak in a particular subsystem. Also, constantly turning on and off a valve causes the refilling of pipes with water, which can cause expedited wear and tear on the pipes and other infrastructure because of the high pressure and force exerted by the water on the pipes as it reenters the subsystem. Thus, it may be beneficial to be able to keep as many subsystems operational as possible while searching for a leak.

Accordingly, a technique for sampling sensors is described herein that can reduce the waste described above when attempting to detect leaks. In particular, the actual sensors themselves may not be as important as how and in what combination measurements are taken from the sensors.

For example, in an embodiment, a building water supply system is monitored and controlled by a single water meter and valve combination. As described above, if the building can be monitored such that leak events are limited to a small volume of water, a great deal of damage can be averted. Financial and physical losses can be decreased, as well as critical systems maintained in a more efficient manner. Insurance costs and/or the total cost of maintenance can also be decreased, thereby having a direct effect on common area maintenance charges of large, highly subdivided spaces in buildings and multi-structure complexes.

The building can include 111 floors and the resolution of the single water meter can be 100 gallons (e.g., the single water meter cannot detect a quantity of water less than 100 gallons). If a building operator needed to measure the amount of water flow into the building, the building operator could time how long it takes to move the water meter by 100 gallons. Dividing the 100 gallon increment by the time would provide a flow rate of water supply into the building. To determine if, for example, there is a leak on floor 23, floor 87, or floor 107, a typical operation would be to shut off the valves on all the floors but 23, 87, and 107 and monitor the water meter. If the water meter, after some time, indicates that 100 gallons passed through the water meter, then this would indicate that there is a leak on one of the three floors. However, in the process of detecting the leak, 100 gallons of water are wasted.

Instead, groups or subsets of subsystems can be sampled using the Hadamard sampling technique to reduce this waste. By sampling in groups or subsets of subsystems using the Hadamard sampling technique, it may be possible to achieve an improvement in the precision of the measurement such that 100 gallons would not need to pass through the water meter before a leak is detected (e.g., only 10 gallons would need to pass through the water meter before a leak is detected even though the water meter has a resolution of 100 gallons). The signal to noise (SNR) of the measurements may also improve. Alternatively, a coarser water meter (e.g., one that measures a minimum of 200 gallons and that presumably is cheaper than a 100 gallon water meter) could be used in conjunction with the Hadamard sampling technique to achieve the same level of performance as with a finer water meter (e.g., one that measures a minimum of 100 gallons).

The Hadamard sampling technique may identify which valves should be on and which valves should be off during any given measurement. Turning certain valves on and certain valves off during measurements can improve the sensitivity of the measurements. In addition, a measurement can be taken at a valve before the valve is shut off and another measurement can then be taken after the valve is shut off. Taking two measurements may improve the SNR by as much as 2×.

An added advantage of using the Hadamard sampling technique may be realized if pressure sensors, such as the pressure sensors 116, are used to speed the data collection process. Conventional methods of taking measurements involve first shutting the entire dendritic water system down. Assuming there are N dendritic water subsystems (which means that N measurements are normally taken), the dendritic water subsystems remain off for all but one measurement of the N measurements. Thus, if there are 100 dendritic water subsystems, each valve remains off for 99% of the time.

If, in the 111-story building, valves are installed on floors 23, 87, and 107, then the building has 4 subsystems (e.g., floor 23, floor, 87, floor 107, and the rest of the floors). In conventional methods, valves supplying floors 23, 87, and 107 could be shut off and the rate of flow measured via the water meter. Then, the valve supplying the other floors could be shut off, the valve for floor 23 could be turned on, and the flow rate could be measured to detect whether the flow rate increased. The valve for floor 23 could then be turned off and the valve for floor 87 could be turned on and the flow rate could be measured again to detect whether the flow rate increased. Similarly, the valve for floor 87 could then be turned off and the valve for floor 107 could be turned on and the flow rate could be measured again to detect whether the flow rate increased. During each test, 100 gallons of water would have to pass through the water meter before the flow rate could be determined. Using addition and/or subtraction, the flow rate for each subsystem could then be determined with 100 gallon resolution.

However, applying a pseudorandom sequence of shutting off and turning on valves and using pressure sensors 116 to take measurements can result in as much as a 2× improvement in the SNR. In an embodiment, the pseudorandom sequence is derived from a mathematical model, such as a Fourier transform (e.g., a Hadamard transform or a Walsh-Hadamard transform). A Hadamard encodement, which correlates with the pseudorandom sequence, is described in greater detail in U.S. Patent Application No. 2004/0218172, which is hereby incorporated by reference herein in its entirety (the Hadamard encodement is described with respect to optics, but can apply to the sequencing of fluid sensors as well).

For example, measurements from the pressure sensors 116 can be used to weight measurements from the water meter by providing added data within the noise floor of the measurement, thereby providing a statistical increase in the SNR. As described above, pressure change over time can indicate possible leaks and can be used to supplement water meter measurement data.

The leak rate can be smaller than the resolution of the water meter and still be detected. The mathematics of this have been well established in Harwit et al., "Hadamard Transform Optics," Academic Press Inc., 1979; DeVerse, "Multiplexed Hyperspectral Imaging and Spectrometry Using Spatial Light Modulators," Kansas State University, 1999; and DeVerse, "Realization of the Hadamard Multiplex Advantage Using a Programmable Optical Mask in a Dispersive Flat-Field Near-Infrared Spectrometer," Kansas State University, 2000, which are hereby incorporated herein by reference in their entireties. In the disclosures provided therein, a single photonic flow sensor was used to measure the flux of light impinging upon an array of light valves. In this manner, the micro-mirror array was acting as an array of valves allowing or not allowing light to pass through the system and onto the single flow measurement device. The analogy holds as the dendritic water system described herein is a confinement of the fluid so there is no difference than if the total flux through the system is measured.

As an example, a single water meter can measure the sum of the quantity of water fed into three individual subsystems. Each subsystem may have a valve that can be controlled to eliminate the flow into that subsystem for a given measurement. Each subsystem valve can be turned on and off in sequence, and the number of measurements taken can be equal to the number of subsystems with valves (e.g., 3 in this example). If the water meter reads in 1 gallon increments, the measurement is limited by this 1 gallon resolution. Use of a Hadamard encodement technique can improve the SNR by the square root of the number of sub-systems with valves divided in half. The Hadamard encodement technique is a weighting scheme that involves measuring the dendritic water system in groups. For example, instead of turning off valves for 2 of the 3 subsystems, only a valve for 1 of the 3 subsystems would be turned off at a time. Thus, additional subsystems may remain functional as the leak detection takes place, thereby limiting the amount of time that water flow is diverted or stopped in a given subsystem. In fact, the number of subsystems that remain off during the leak detection for any given measurement goes from N−1 (e.g., all but 1 subsystem valve is off) to ((N/2)−1) (e.g., less than half of the subsystem valves are off).

When the valve of a subsystem is to be turned off, a pressure sensor 116 associated with the valve can take a measurement of the water pressure before the valve is turned off and after the valve is turned off. The reduction in water pressure between the on and off state may be related to the relative reduction of the volume of water in the subsystem. In addition, the sensor data server 140, for example, may store information indicating a known reservoir of water in the subsystem when the measurements are to be taken. This known reservoir of water may partially empty during the off state of the valve, and thus the quantity of water in the reservoir can be taken into account to adjust the measured water pressure.

Figure 2:
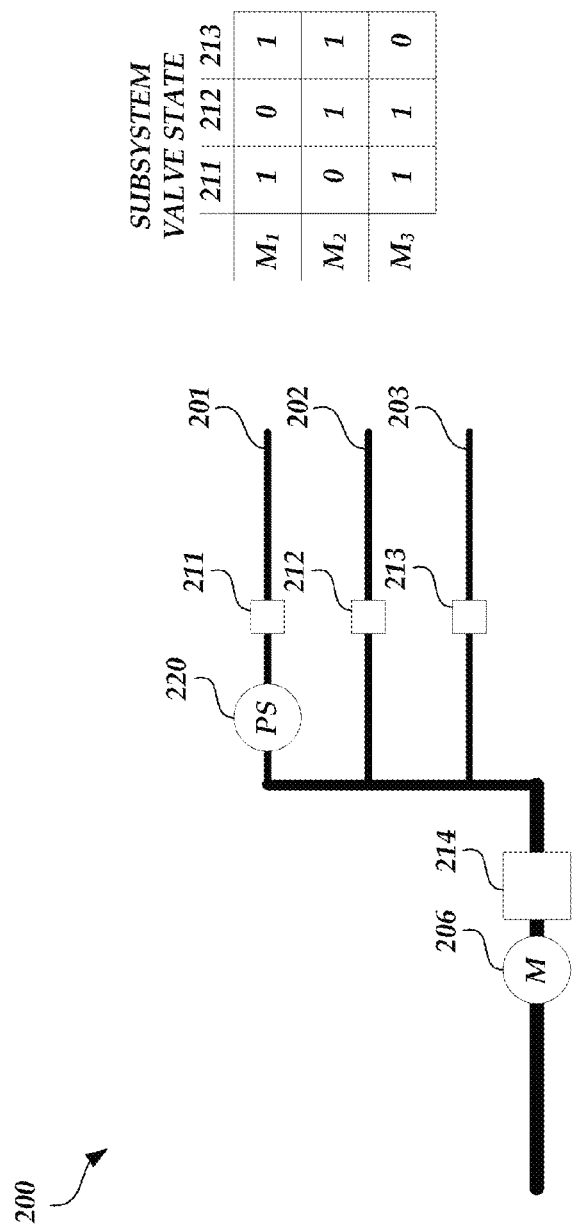
FIG. 2 illustrates an exemplary dendritic water system in which various subsystems of the dendritic water system are measured using a Hadamard sampling technique.

FIG. 2 illustrates an exemplary dendritic water system 200 in which various subsystems of the dendritic water system 200 are measured using a Hadamard sampling technique. As illustrated in FIG. 2, the dendritic water system 200 includes 3 subsystems: subsystems 201, 202, and 203. The subsystem 201 includes a valve 211, the subsystem 202 includes a valve 212, and the subsystem 203 includes a valve 213, where each of the valves 211-213 can stop water flow into the respective subsystem.

Furthermore, the dendritic water system 200 may include a water meter 206 that monitors water flow into each of the subsystems 201-203 and a valve 214 located adjacent to the water meter 206. In an embodiment, the valve 214 can modulate total water flow into the subsystems 201, 202, and 203.

In an embodiment, the valves 211-213 can be modulated according to a pseudorandom sequence derived from the Hadamard transform. Measurements can be taken by a pressure sensor 220 and/or the water meter 206 (e.g., via a magnetic field sensor 114 coupled with the water meter 206). For example, a first measurement (e.g., $M_1$) can be taken when valves 211 and 213 are on and valve 212 is off. A second measurement (e.g., $M_2$) can be taken when valve 211 is off and valves 212 and 213 are on. A third measurement (e.g., $M_3$) can be taken when valves 211 and 212 are on and valve 213 is off.

The sensor data server 140 (e.g., the instruction generator 146) may transmit signals to the valves 211-213 to implement the pseudorandom sequence described above. Furthermore, the sensor data server 140 may transmit messages to the water meter 206 and/or the pressure sensor 220 to take measurements and transmit such measurements to the sensor data server 140 or may transmit messages to the water meter 206 and/or the pressure sensor 220 to request current measurements.

Once the measurements are received by the sensor data server 140, the sensor data server 140 (e.g., the predictive failure analyzer 147) may apply a Hadamard transform to the 3 measurements. Applying the Hadamard transform results in three values, where each value represents the individual water flow rate of one of the valves 211-213 (and thus of one of the subsystems 201-203). While each value resulting from the application of the Hadamard transform is equivalent to a water flow rate that could be determined by shutting off all but one of the valves 211-213 and measuring the water flow rate of the open valve, the techniques described herein provide the benefit of allowing more than 50% of the valves to remain open (and thereby allowing critical subsystems to stay operational and/or reducing the wear and tear on pipes and other infrastructure that occurs from the refilling of water in a subsystem). Once the water flow rate for each of the subsystems 201-203 are determined, then the predictive failure analyzer 147 can compare the water flow rates with historical water flow rates (e.g., previously calculated water flow rates stored in the sensor data store 148). If a water flow rate for a subsystem 201-203 is higher than the historical water flow rate (e.g., an average historical water flow rate) for that subsystem 201-203 by a threshold value and/or the water flow rate is trending upward over time, then the predictive failure analyzer 147 can determine that there may be a leak in the subsystem 201-203.

The water meter 206 may supply water flow rate measurements for the dendritic water system 200 as a whole, and thus the sensor data server 140 can use the water flow rate measurements for the dendritic water system 200 as a whole and the individual water flow rate measurements for each of the subsystems 201-203 to identify possible leaks between the valve 214 and the valves 211-213. For example, if the predictive failure analyzer 147 detects no leaks in subsystems 201-203, but the water meter 206 shows some water flow when the valve 214 is shut off, then the predictive failure analyzer 147 can determine that a leak is present between valve 214 and the valves 211-213.

The sensor data server 140 can automatically modulate the valves 211-213 in this manner in regular or irregular intervals to monitor for leaks. Alternatively or in addition, a user can request a leak detection check by, for example, initiating a test via an application running on the user device 160.

While FIG. 2 depicts 3 subsystems 201-203, this is not meant to be limiting. The techniques described in conjunction with FIG. 2 can apply to any number of subsystems. For example, the number of measurements taken may equal the number of subsystems. Furthermore, during each measurement, more than 50% of the valves in the subsystems may remain on.

In further embodiments, not shown, the dendritic water system 200 includes a water waste system, such that the dendritic water system 200 includes inflow (e.g., water passing into the dendritic water system 200 through water meter 206) and outflow (e.g., water exiting the dendritic water system 200). Sensors, such as pressure sensors 116 can be positioned along the inflow path and the outflow path and modulated according to the pseudorandom sequence described above. Thus, leaks can also be identified in both inflow and outflow paths in the dendritic water system 200.

Figure 3:
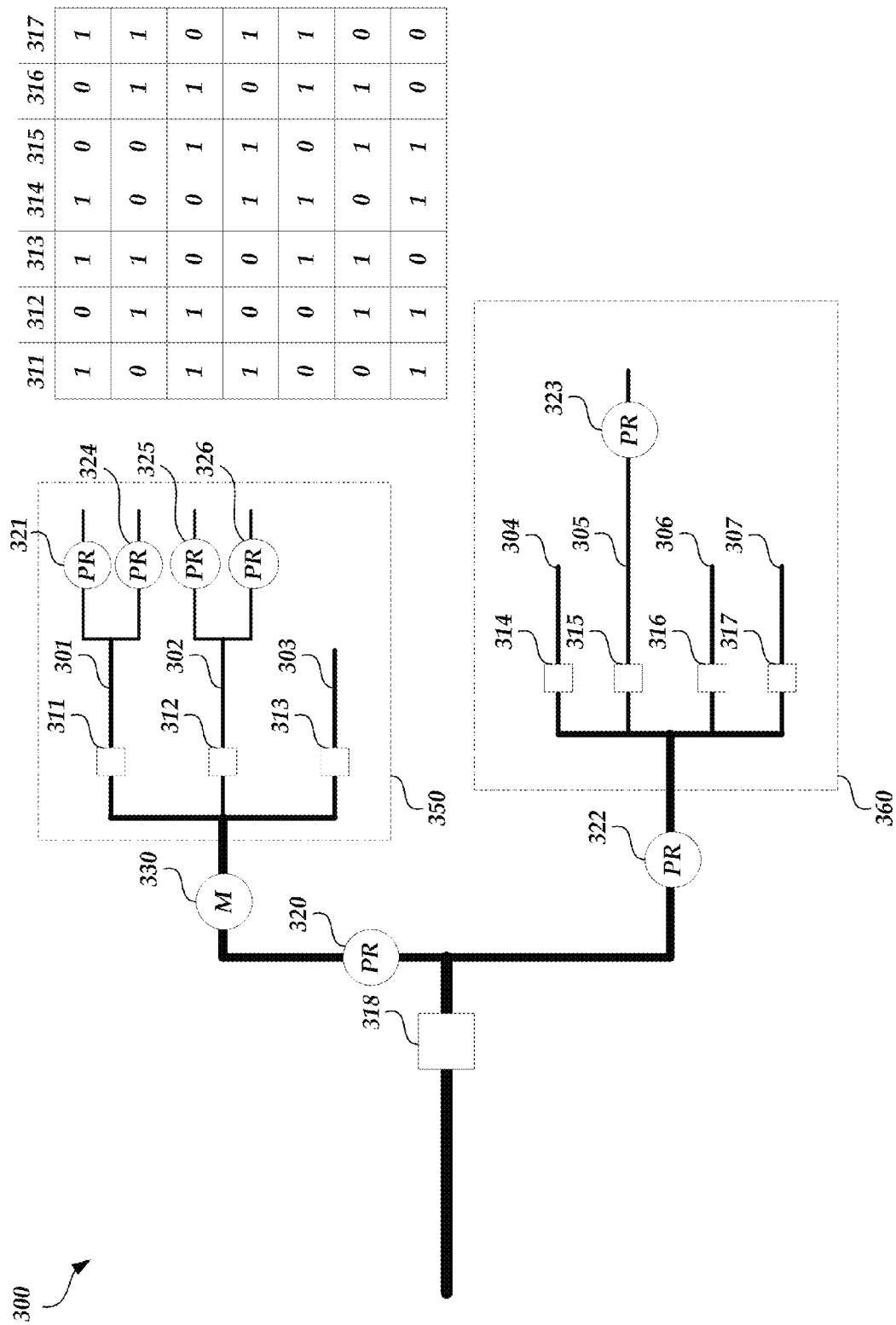
FIG. 3 illustrates another exemplary dendritic water system in which various subsystems of the dendritic water system are measured using a Hadamard sampling technique.

FIG. 3 illustrates another exemplary dendritic water system 300 in which various subsystems of the dendritic water system 300 are measured using a Hadamard sampling technique. As illustrated in FIG. 3, the dendritic water system 300 includes 7 subsystems: subsystems 301, 302, 303, 304, 305, 306, and 307. The subsystem 301 includes a valve 311, the subsystem 302 includes a valve 312, the subsystem 303 includes a valve 313, the subsystem 304 includes a valve 314, the subsystem 305 includes a valve 315, the subsystem 306 includes a valve 316, and the subsystem 307 includes a valve 317, where each of the valves 311-317 can stop water flow into the respective subsystem.

As an example, the subsystems 301-303 may each be located on different floors of a building 350 and the subsystems 304-307 may beach be located on different floors of a building 360. A valve 318 may control the flow of water into the buildings 350 and 360.

The dendritic water system 300 may further include pressure regulators 320-326 and a water meter 330. The pressure regulators 320-326 can modulate the pressure of the water flowing into the various subsystems 301-307 at different frequencies. For example, the pressure regulator 320 can modulate the flow of water into the building 350 at a first frequency (e.g., the water pressure rises and falls periodically at the first frequency), the pressure regulator 321 can modulate the flow of water into a first subsystem of the subsystem 301 at a second frequency, the pressure regulator 322 can modulate the flow of water into the building 360 at a third frequency, the pressure regulator 323 can modulate the flow of water into the subsystem 305 at a fourth frequency, the pressure regulator 324 can modulate the flow of water into a second subsystem of the subsystem 301 at a fifth frequency, the pressure regulator 325 can modulate the flow of water into a first subsystem of the subsystem 302 at a sixth frequency, and the pressure regulator 326 can modulate the flow of water into a second subsystem of the subsystem 302 at a seventh frequency. Furthermore, the valves 311-317 can be modulated from a closed position (or a partially closed position) to an open position (or a partially opened position) to control the flow of water into the respective subsystems 301-307.

As an example, the pseudorandom sequence (e.g., the Hadamard encodement) for modulating the valves 311-317 can be as follows: (1) valves 311, 313, 314, and 317 are on and valves 312, 315, and 316 are off; (2) valves 312, 313, 316, and 317 are on and valves 311, 314, and 315 are off; (3) valves 311, 312, 315, and 316 are on and valves 313, 314, and 317 are off; (4) valves 311, 314, 315, and 317 are on and valves 312, 313, and 316 are off; (5) valves 313, 314, 316, and 317 are on and valves 311, 312, and 315 are off; (6) valves 312, 313, 315, and 316 are on and valves 311, 314, and 317 are off; and (7) valves 311, 312, 314, and 315 are on and valves 313, 316, and 317 are off.

During each of these sequences, the water meter 330 can, via a coupled magnetic field sensor 114, measure the water flow. In addition, the pressure regulators 320-326 can modulate the water pressure at the respective frequencies during each of these sequences. Thus, when a measurement is taken at a first time when the valves 311-317 are modulated according to the first sequence, the pressure regulators 320-326 can each be modulated in a first state. When a measurement is taken at a second time when the valves 311-317 are modulated according to the first sequence, the pressure regulators 320-326 can each be modulated in a different state (e.g., because the frequency of taking a measurement when the valves 311-317 are modulated according to the first sequence may not match the frequency of modulation of the pressure regulators 320-326). Furthermore, the sensor data server 140 instructs the valves 311-317 to modulate, instructs the pressure regulators 320-326 to modulate at a given frequency, and instructs the magnetic field sensor 114 to take measurements, and therefore the sensor data server 140 knows a state of each valve 311-317 and of each pressure regulator 320-326 during any given measurement. The water meter 330 (or the magnetic field sensor 114 coupled thereto) can be configured to take measurements periodically such that, for each sequence, a plurality of measurements are taken at different time instances.

The sensor data server 140 (e.g., the predictive failure analyzer 147), for a given sequence, can take the measurements provided by the magnetic field sensor 114 over a period of time, the state of each of the valves 311-317 during each measurement, and the frequency information for each of the pressure regulators 320-326 during each measurement, and apply a Fourier transform to the measurements for the given sequence. The sensor data server 140 can then calculate a modulus of the Fourier transform and perform an inverse Fourier transform on the modulus to generate a value for the given sequence. The sensor data server 140 can then repeat this process for each of the other sequences to generate a value for the respective sequence. The sensor data server 140 can then apply a Hadamard transform to each of the generated values to determine a water flow rate in each of the subsystems 301-307 and identify any potential leaks in a manner as described above. Alternatively, the sensor data server 140 can apply the Hadamard transform before applying the Fourier transform.

In further embodiments, the sensor data server 140 can alter the analysis of the measurements from the water meter 330 based on expected water flow patterns over time. In some cases, dendritic water systems exhibit reoccurring patterns of water flow that can allow for the grouping of measurements. For example, a dendritic water system can include a group of low-rise apartments. Over time, the sensor data server 140 may identify a water use pattern with a first apartment (e.g., no water is consumed in the first apartment). The sensor data server 140 may make this determination based on measurements taken from a water meter. The sensor data server 140 may alternatively or in addition make this determination based on occupancy data.

Figure 4:
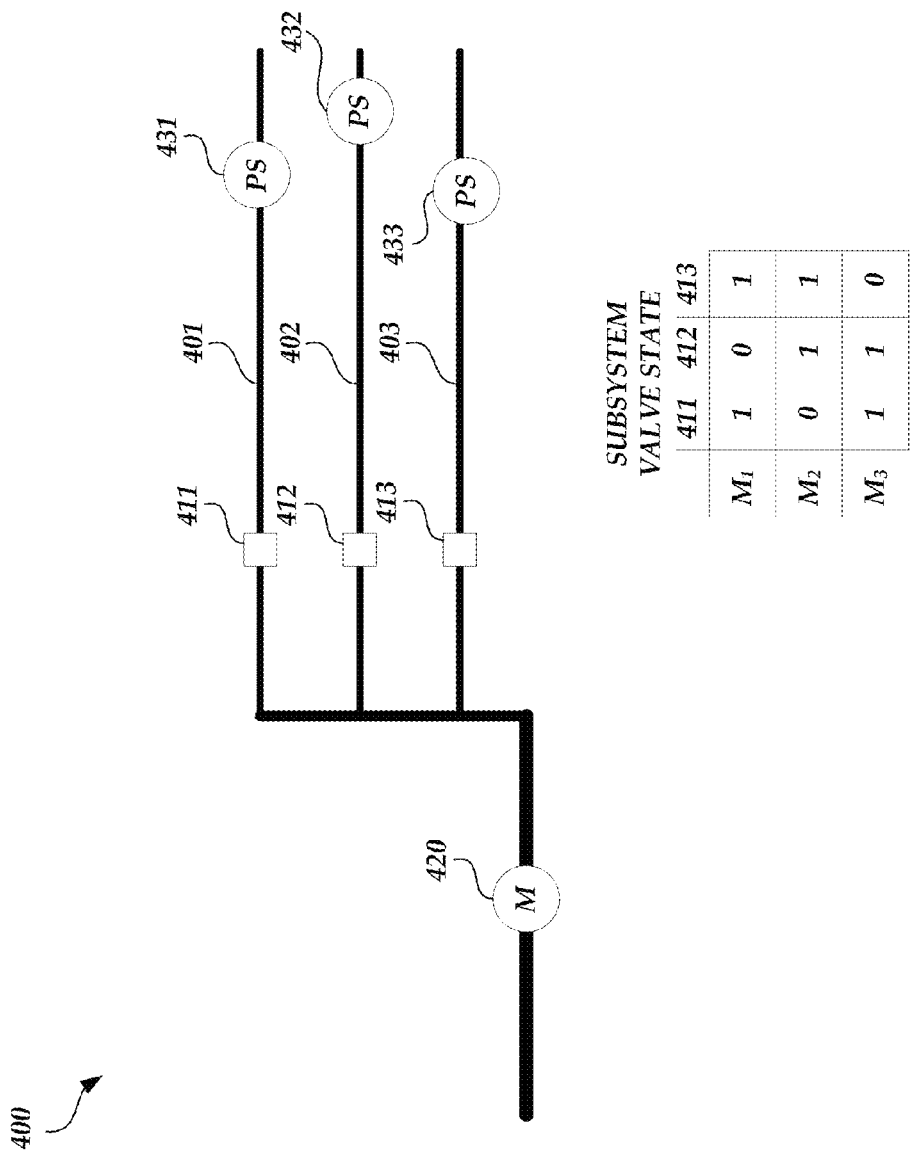
FIG. 4 illustrates another exemplary dendritic water system in which various subsystems of the dendritic water system are measured using a Hadamard sampling technique.

FIG. 4 illustrates another exemplary dendritic water system 400 in which various subsystems of the dendritic water system 400 are measured using a Hadamard sampling technique. As illustrated in FIG. 4, the dendritic water system 400 includes 4 subsystems: subsystems 401, 402, and 403. The subsystem 401 includes a valve 411 and a pressure sensor 431, the subsystem 402 includes a valve 412 and a pressure sensor 432, and the subsystem 403 includes a valve 413 and a pressure sensor 433. Each of the valves 411-413 can stop water flow into the respective subsystem and each of the pressure sensors 431-433 can detect the water pressure level. Furthermore, the dendritic water system 400 may include a water meter 420 that monitors water flow into each of the subsystems 401-403.

In an embodiment, the valves 411-413 can be modulated according to a pseudorandom sequence derived from the Hadamard transform, such as a pseudorandom sequence similar to the pseudorandom sequence depicted in FIG. 2. For example, a first measurement (e.g., $M_1$) can be taken when valves 411 and 413 are on and valve 412 is off. A second measurement (e.g., $M_2$) can be taken when valve 411 is off and valves 412 and 413 are on. A third measurement (e.g., $M_3$) can be taken when valves 411 and 412 are on and valve 213 is off.

The pressure sensor 431-433 associated with a shut off valve 411-413 may take two measurements: one measurement before the respective valve 411-413 is shut off and one measurement after the respective valve 411-413 is shut off.

For example, in the first measurement, the pressure sensor 432 may measure the water pressure in subsystem 402 before the valve 412 is shut off and take another measurement of the water pressure in subsystem 402 after the valve 412 is shut off. The sensor data server 140 (e.g., the predictive failure analyzer 147) may calculate the difference between the two measurements and divide the difference by the time elapsed between the two measurements to determine a water pressure reduction rate.

The pressure sensors 431-433 associated with valves 411-413 that are on may take a measurement. The sensor data server 140 may then sum the measurements taken by the pressure sensors 431-433 associated with valves 411-413 that are on with the water pressure reduction rate. For example, in the first measurement, the pressure sensor 431 may measure the water pressure in subsystem 401 and the pressure sensor 433 may measure the water pressure in subsystem 403. The sensor data server 140 may calculate a sum of the measurement by the pressure sensor 431, the measurement by the pressure sensor 433, and the water pressure reduction rate associated with the pressure sensor 432. The sensor data server 140 can then apply a Hadamard transform to the sum associated with each of the sequences to identify potential leaks in a manner as described above.

As described above, the sensor data server 140 (e.g., the instruction generator 146) may transmit signals to the valves 411-413 to implement the pseudorandom sequence. Furthermore, the sensor data server 140 may transmit messages to the pressure sensors 431-433 to take measurements and transmit such measurements to the sensor data server 140 or may transmit messages to the pressure sensors 431-433 to request current measurements.

The sensor data server 140 can automatically modulate the valves 411-413 in this manner in regular or irregular intervals to monitor for leaks. Alternatively or in addition, a user can request a leak detection check by, for example, initiating a test via an application running on the user device 160.

While FIG. 4 depicts 3 subsystems 401-403, this is not meant to be limiting. The techniques described in conjunction with FIG. 4 can apply to any number of subsystems.

Magnetic Field Sensor

Figure 5:
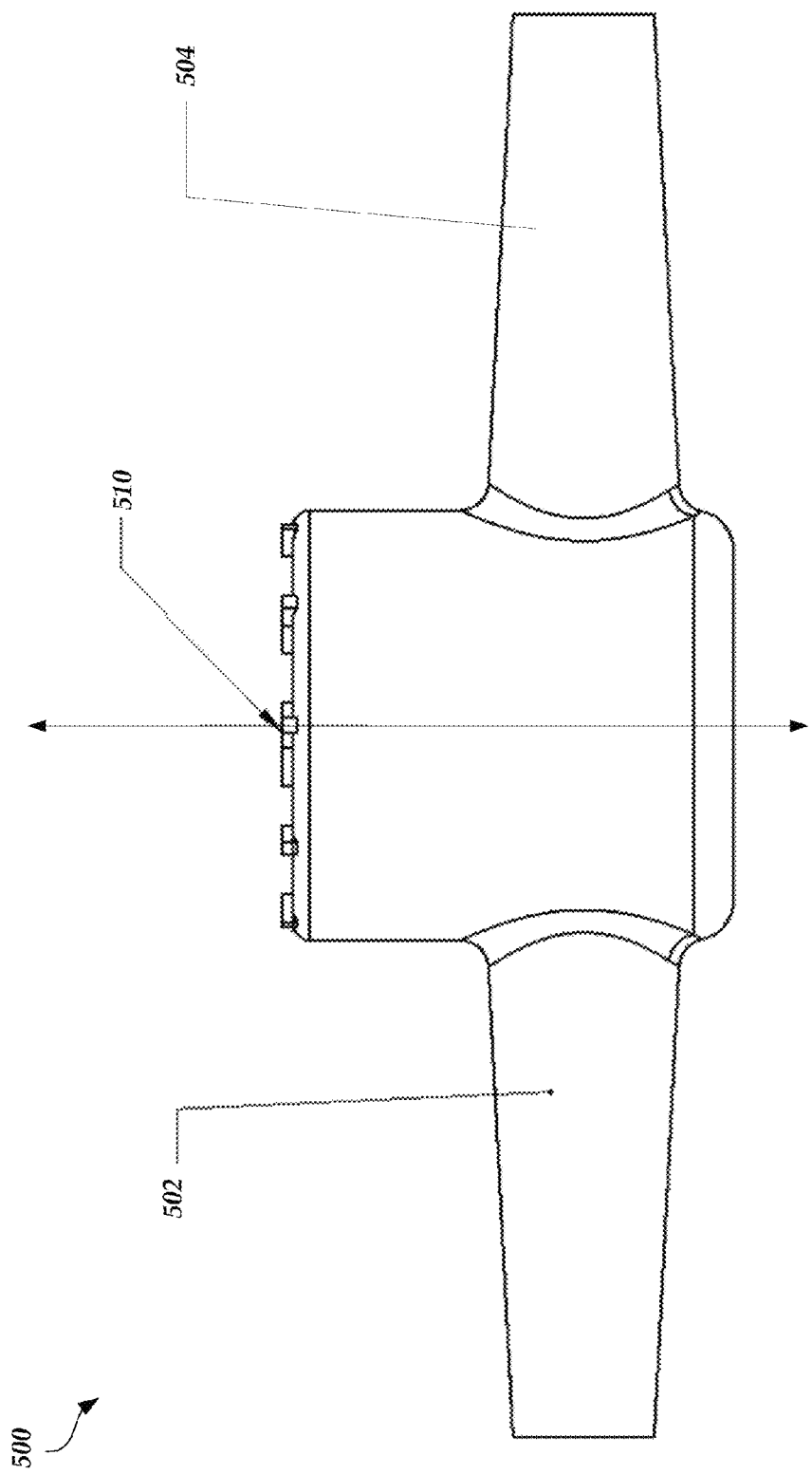
FIG. 5 illustrates a fluid meter.

FIG. 5 illustrates a fluid meter 500. In an embodiment, the fluid meter 500 couples between a first pipe 502 and a second pipe 504 in a dendritic fluid system. The fluid meter 500 is an enclosed and/or sealed structure that includes a magnet (e.g., ferrite) that rotates as fluids flow through the fluid meter 500. The magnet may rotate vertically or horizontally about an axis 510 that vertically passes through a top surface and a bottom surface of the fluid meter 500 and that is perpendicular to a direction of the fluid flow. For example, the magnet can be positioned vertically such that the magnet is in a plane that is generally transverse to the direction of the fluid flow. As another example, the magnet can be positioned horizontally such that the magnet is co-planar with the direction of the fluid flow.

FIG. 6A illustrates a top view perspective of a magnetic field sensor 600 that measures a change in a magnetic field as caused by the rotation of the magnet in the fluid meter 500. As illustrated in FIG. 6A, the magnetic field sensor 600 is not in contact with the fluid meter 500 and is instead positioned a distance 610 from the fluid meter 500. In an embodiment, the magnetic field sensor 600 does not have to be positioned at a particular location relative to the fluid meter 500. For example, the magnetic field sensor 600 does not have to be positioned at a certain height above the bottom surface of the fluid meter 500, at a certain height below the top surface of the fluid meter 500, at a certain distance from a left surface of the fluid meter 500, at a certain distance from a right surface of the fluid meter 500, at a certain distance from a back surface of the fluid meter 500, or at a certain distance from a front surface of the fluid meter 500. Rather, the magnetic field sensor 600 can be positioned anywhere a distance 610 from the fluid meter 500 (e.g., anywhere in a plane that extends generally transverse to the axis 510). This is in contrast to conventional fluid meter sensors, which typically must be placed atop the location of the magnet on the exterior of the fluid meter.

The magnetic field sensor 600 can measure a perturbation of the magnetic field generated by the magnet in the fluid meter 500 in three dimensions as the magnet rotates. In normal operation, the magnet rotates along the axis 510 such that the magnetic field changes in only two dimensions (e.g., at each height of the fluid meter 500, the magnetic field remains constant during rotation). The magnetic field sensor 600 can measure these changes, which are eventually used to determine the rate of flow of fluid through the pipes 502 and 504. For example, a complete rotation of the magnet can be correlated with a certain volume of fluid. A time it takes for the magnet to rotate completely can indicate how long it takes for the certain volume of fluid to pass through the pipes 502 and 504 and thereby the rate of fluid flow. The rate of fluid flow can be used to identify potential leaks, as described herein.

However, the magnets and/or other components of the fluid meter 500 can become faulty or fail as time passes. For example, the rotating magnet may be configured to cause a change in the magnetic field along only two axes (e.g., because the magnet is positioned horizontally and co-planar with the direction of the fluid flow such that a center of the magnet is fixed to the axis 510). However, if the magnet becomes loose such that while the magnet rotates about the axis 510, the magnet also begins to oscillate vertically or horizontally between angles that deviate from the axis 510 (e.g., the magnet begins to wobble up and down or side to side as the magnet rotates), this can indicate a possible malfunction. Because the magnetic field sensor 600 can measure a perturbation of the magnetic field generated by the magnet in three dimensions, the magnetic field sensor 600 can measure these unexpected changes in the third dimension. Thus, the data measured by the magnetic field sensor 600 can also be used to detect failures or malfunctions.

Conventional fluid meter sensors measure the oscillation of the magnet inside the fluid meter between a north and south orientation (e.g., a change in polarity in the magnet), and so a very high or very low water flow may be undetectable by these conventional fluid meter sensors (e.g., because the rate of oscillation of the magnet is faster than the sampling speed or because the magnet does not fully oscillate from north to south and back to north because of the low water flow). In contrast, the magnetic field sensor 600 detects a change in the orientation of the magnetic field, and the orientation of the magnetic field changes even with a very high water flow or a very low water flow. Thus, a very high water flow or a very low water flow can still be detected due to the change in the orientation of the magnetic field.

The magnetic field sensor 600 can include a head 602 and a cable 604 coupled with the head 602. The head 602 can include one or more multi-axis sensors to detect changes to the magnetic field in three dimensions that are enclosed within a protective enclosure. For example, the protective enclosure can protect the multi-axis sensors from hazardous weather conditions, such as rain, wind, snow, and/or the like.

A multi-axis sensor can measure a magnitude of the magnetic field and an orientation of the magnetic field in three axes (e.g., three dimensions). When multiple measurements are analyzed, the speed of the change in the magnetic field and the direction of the change in the magnetic field can be determined.

FIG. 6B illustrates a position of the multi-axis sensors 651-653 relative to each other in the head 602. In an embodiment, the multi-axis sensors 651-653 are a resistive Wheatstone bridge network of hall-effect sensors, where the hall-effect sensors are rotated in different orientations (e.g., orthogonally to each other) such that each sensor measures magnetic fields in a different axis. For example, first sensor 651 is oriented in a first direction (e.g., an x-axis), second sensor 652 is oriented in a second direction (e.g., a y-axis), and third sensor 653 is oriented in a third direction (e.g., a z-axis).

The head 602 can also include a focused ferrite pole or an array of ferrite poles that can be used to concentrate and/or focus the magnetic lines of force produced by the magnet in the fluid meter 500, thereby extending the distance the magnetic field sensor 600 can be positioned from the fluid meter 500. For example, a ferrite pole can be positioned above the plane of the printed circuit board (PCB) in the head 602 and another ferrite pole can be positioned below the plane of the PCB in the head 602. In addition, a ferrite pole can be positioned on and/or below the multi-axis sensors.

In further embodiments, the multi-axis sensors are a pair of perm-alloy Wheatstone bridge resistive elements amplified in two phases. An analog signal generated by the resistive elements may be more effective when the plane of the circuit including the multi-axis sensors is in the plane of the rotation of the magnetic field. The change in the magnetic field can be detected as an analog signal that is relative to the absolute rotational position of the magnetic field. The head 602 may include an amplifier to amplify the analog signal and/or an analog-to-digital circuit (ADC) to digitize the amplified analog signal for transmission via the network 120.

As described herein, the magnetic field sensor 600, along with other magnetic field sensors in the sensor system 100, can be sampled according to Hadamard techniques. The SNR improvements achieved by using the Hadamard sampling techniques may allow for the magnetic field sensor 600 to be placed a further distance 510 away from the fluid meter 500 while still being able to measure the magnetic field generated by the magnet by an amount sufficient to measure the fluid flow.

Figure 7A:
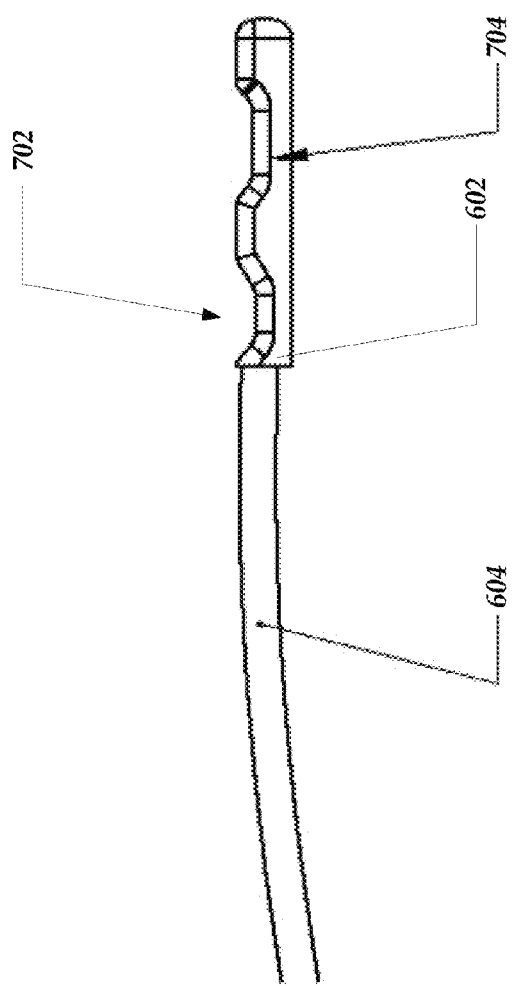
FIG. 7A illustrates a side perspective view of the head and the cable of the magnetic field sensor of FIG. 6A.
Figure 7B:
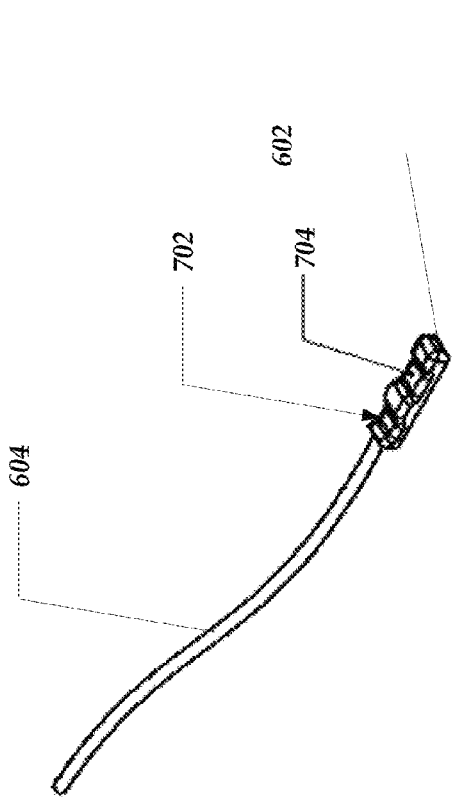
FIGS. 7B-7C further illustrate other side perspective views of the head and the cable of the magnetic field sensor of FIG. 6A.
Figure 7C:
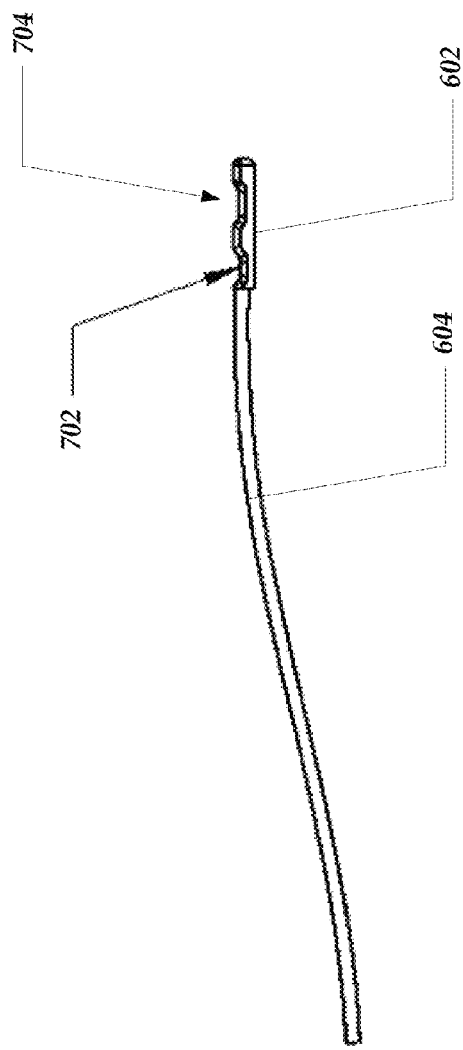

FIG. 7A illustrates a side perspective view of the head 602 and the cable 604 of the magnetic field sensor 600. FIGS. 7B-7C further illustrate other side perspective views of the head 602 and the cable 604 of the magnetic field sensor 600. FIG. 7D illustrates a top perspective view of the head 602 and the cable 604 of the magnetic field sensor 600 and FIG. 7E illustrates a bottom perspective view of the head 602 and the cable 604 of the magnetic field sensor 600. As illustrated in FIGS. 7A-7E, a top portion of the head 602 can include one or more depressions 702 and 704. These depressions 702 and 704 may allow for the mounting or removable attachment of the magnetic field sensor 600 to a physical component (e.g., a pipe, a wall, etc.) using, for example, standard plastic mounting strips or ties, bungie cords, and/or the like. The bottom portion of the head 602 may be flat or nearly flat or shaped to mate with another physical component (e.g., a pipe, a wall, etc.).

The cable 604 can be a data cable used to transport data measured by the multi-axis sensors in the head 602 to a transceiver and/or storage device. For example, one end of the cable 604 can include a wireless transceiver such that the data measured by the multi-axis sensors can be transmitted wirelessly to the sensor data server 140 for storage and/or analysis. The wireless transceiver can associate with the network 120 before transmissions occur. In an embodiment, the cable 604 is a thin shielded cable that includes a plurality of wires (e.g., 4).

Figure 8:
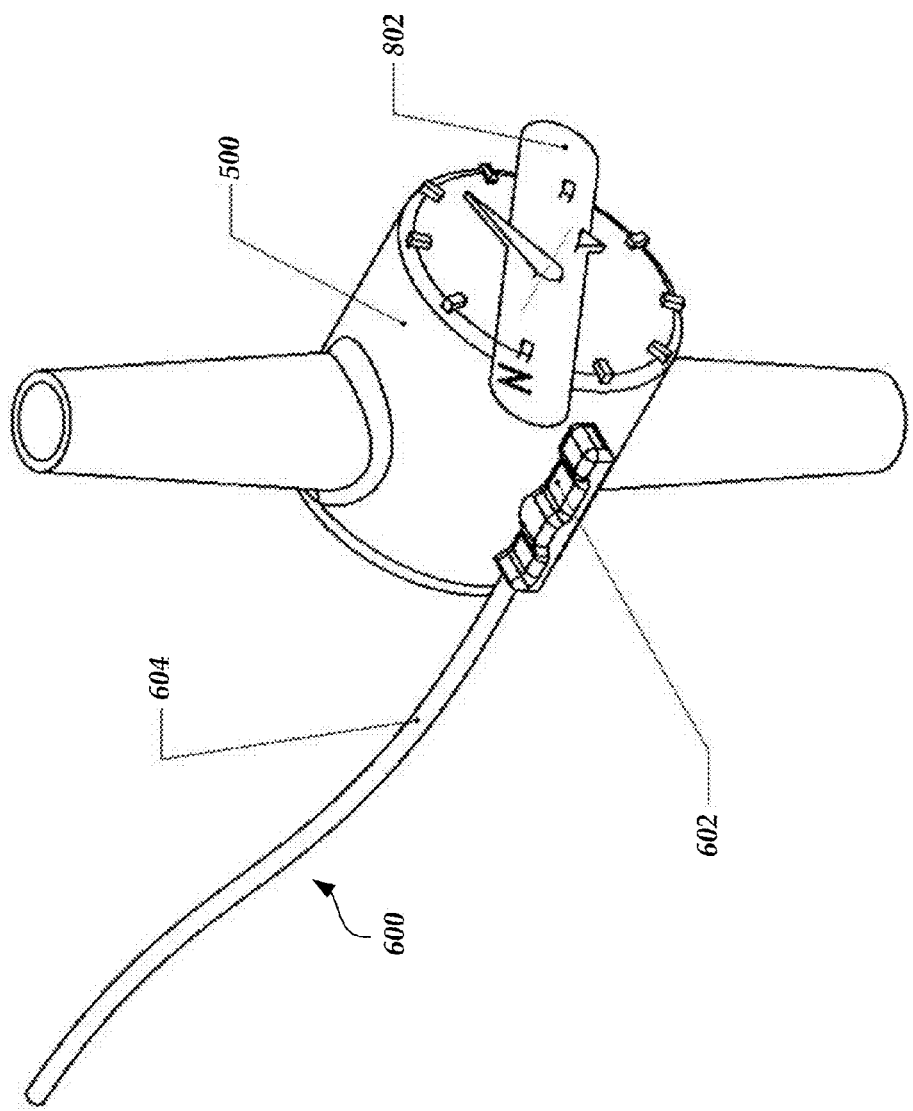
FIG. 8 illustrates a side perspective view of the magnetic field sensor of FIG. 6A and the fluid meter of FIG. 5.

FIG. 8 illustrates a side perspective view of the magnetic field sensor 600 and the fluid meter 500. As illustrated in FIG. 8, magnetic field lines 802 generated by the magnet inside the fluid meter 500 are oriented toward the magnetic field sensor 600.

Figure 9:
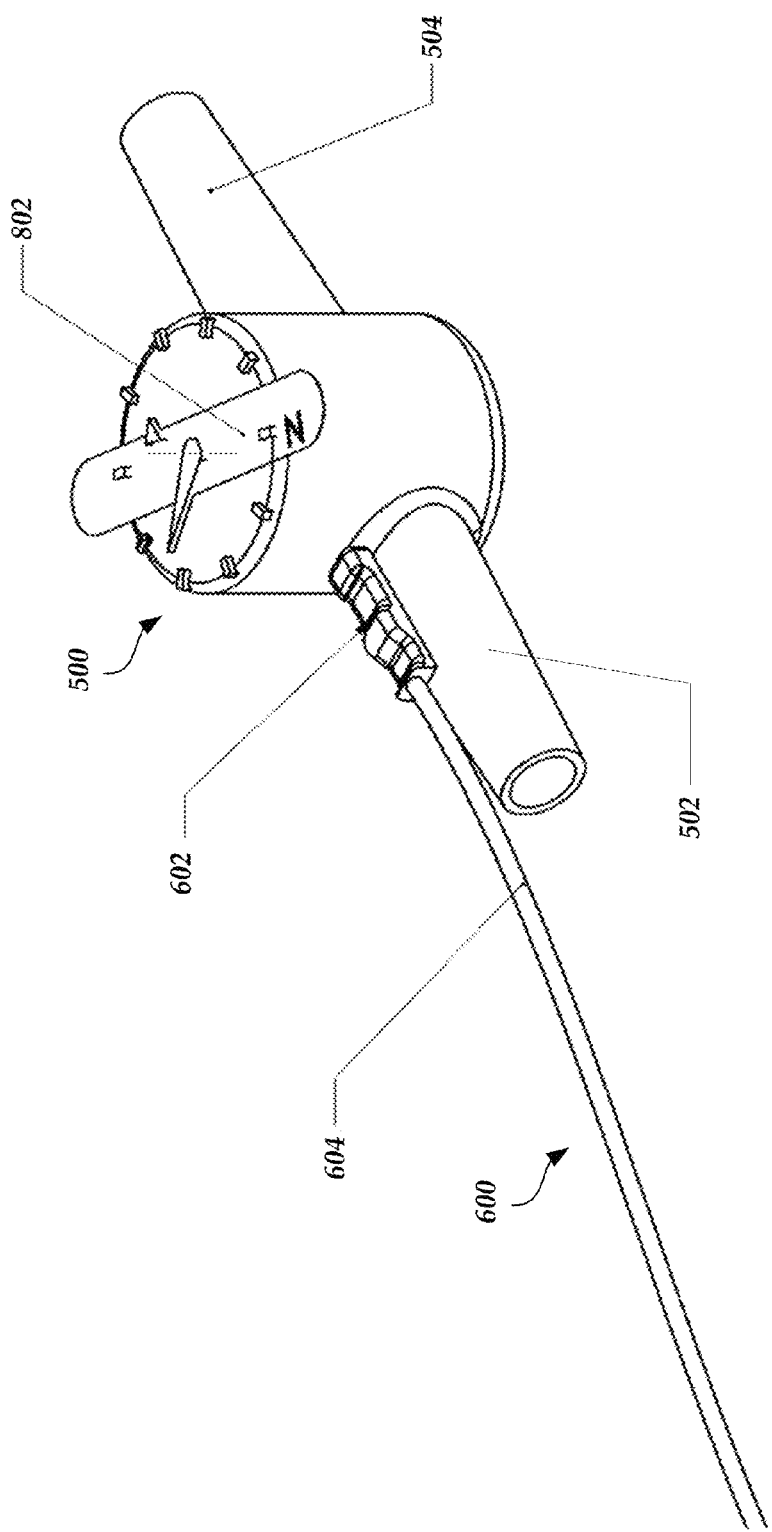
FIG. 9 illustrates another side perspective view of the magnetic field sensor of FIG. 6A and the fluid meter of FIG. 5.

FIG. 9 illustrates another side perspective view of the magnetic field sensor 600 and the fluid meter 500. As illustrated in FIG. 9, the magnetic field sensor 600 is positioned above and in parallel with a top surface of the pipe 502, with the head 602 positioned such that an end of the head 602 opposite the cable 604 is the distance 510 from the fluid meter 500. FIG. 9 is an illustrative example of a position of the magnetic field sensor 600 relative to the fluid meter 500 and is not meant to be limiting. For example, the head 602 can be positioned such that a left or right surface of the head 602 is the distance 510 from the fluid meter 500. The ability to mount the magnetic field sensor 600 in any orientation as described herein can decrease installation costs.

In an embodiment, the magnetic field sensor 600 operates in a sleep state and an active state. For example, the magnetic field sensor 600 may enter a sleep state for a first time period (e.g., 1 minute) and then transition into an active state for a second time period. During the active state, a two-stage amplifier and a switch circuit may be powered. The switch circuit may power an analog system (e.g., the multi-axis sensors) that provides a relative voltage on two outputs that is indicative of the near-field orientation of the magnetic lines of force generated by the magnet in the fluid meter 500.

The magnetic field sensor 600 may repeat the measurement periodically (e.g., every 33 ms) and the data can be processed (e.g., by the magnetic field sensor 600 or by the sensor data server 140) to calculate the rotational speed of the change in the angle of the magnetic lines of force in the near-field and/or the absolute position and field strength of the magnetic lines of force. For example, magnetic field sensor 600 can convert each analog signal (e.g., each analog signal is generated by a sensor that measures a different axis, such that there are three analog signals) into a digital value using the ADC and store the digital values in a buffer and repeat this process for two periodic measurements. The magnetic field sensor 600 (e.g., a microcontroller of the magnetic field sensor 600) can then calculate the slope of the first periodic measurement and the second periodic measurement (and possibly perform an operation to ensure that the slope is not a negative value). The calculated slope may correspond to a change in speed and/or orientation of the magnetic field generated by the magnet in the fluid meter 500.

The magnetic field sensor 600 may also measure temperature to compensate for any measurement errors introduced by variations in temperature (e.g., the microcontroller of the magnetic field sensor 600 or the sensor data server 140 can perform the compensation). The data measured by the magnetic field sensor 600 can be used to detect dendritic water system 150 use patterns. Over time, these patterns can be related to and/or be indicative of dendritic water system 150 use patterns and/or performance patterns. Based on the identified use and/or performance patterns, the magnetic field sensor 600 can adjust the sampling frequency. For example, instead of sampling periodically, the magnetic field sensor 600 may increase the frequency of measurements at certain times of the day (e.g., when the dendritic water system 150 is in use) and decrease the frequency of measurements at other times of the day (e.g., when the dendritic water system 150 is not in use).

In further embodiments, a plurality of magnetic field sensors 600 can be placed near the fluid meter 500 to detect a direction of the fluid flow. For example, a first magnetic field sensor 600 can be placed in the plane of rotation of the magnet in the fluid meter 500. A second magnetic field sensor 600 can be placed outside of the plane of rotation of the magnet in the fluid meter 500. The sensor data server 140 can process the measurements from the two magnetic field sensors 600 to derive the fluid flow direction.

As measurements are collected from the magnetic field sensor 600 by the sensor data server 140, the sensor data server 140 (e.g., the predictive failure analyzer 147) can analyze the data to determine whether water is flowing through the fluid meter 500 that the magnetic field sensor 600 is monitoring and how long the water has been flowing. For example, if consecutive measurements indicate that the magnetic field generated by the magnet in the fluid meter 500 is continuously changing (e.g., along the axes that indicate a north-to-south oscillation of the magnet, such as the axes that are co-planar with a plane extending generally transverse from the axis 510), then the predictive failure analyzer 147 may determine that water is flowing through the fluid meter 500 for a time period corresponding to the consecutive measurements. Conversely, if consecutive measurements indicate that the magnetic field generated by the magnet in the fluid meter 500 is not changing (e.g., along the axes that indicate a north-to-south oscillation of the magnet, such as the axes that are co-planar with a plane extending generally transverse from the axis 510), then the predictive failure analyzer 147 may determine that water is not flowing through the fluid meter 500 for a time period corresponding to the consecutive measurements.

If the predictive failure analyzer 147 determines that water has not flowed for at least a first time period (e.g., 5 minutes) within a second time period (e.g., 1 hour), then the predictive failure analyzer 147 can instruct the user interface generator 144 to generate an icon of a first color (e.g., green) to be displayed in a user interface displayed by the user device 160. The icon of the first color may indicate to a user that the fluid meter 500 is operating properly and/or no leaks are detected. If the predictive failure analyzer 147 determines that water has not stopped flowing for at least a third time period (e.g., 45 minutes) within the second time period, then the predictive failure analyzer 147 can instruct the user interface generator 144 to generate the icon with a second color (e.g. yellow) to be displayed in a user interface displayed by the user device 160. The icon of the second color may indicate to a user that a leak may be present and/or to keep an eye on any fixtures or appliances within the subsystem monitored by the fluid meter 500. If the predictive failure analyzer 147 determines that water has not stopped flowing for at least a fourth time period (e.g., 4 hours), then the predictive failure analyzer 147 can instruct the user interface generator 144 to generate the icon with a third color (e.g. red) to be displayed in a user interface displayed by the user device 160. The icon of the third color may indicate to a user that a leak is likely present and/or to inspect the fixtures or appliances within the subsystem monitored by the fluid meter 500 immediately. In addition, the predictive failure analyzer 147 can instruct the alert generator 142 to generate an alert for notifying a user of a potential or likely leak (e.g., if the determined color is yellow or red).

Alternatively or in addition, the predictive failure analyzer 147 can transmit the time information described above to a network-enabled standalone device (not shown) via the network 120. The network-enabled standalone device can be placed anywhere in a dendritic fluid system and include a display to indicate one of the three colors. For example, the network-enabled standalone device can be located within each subsystem (e.g., such that the number of network-enabled standalone devices matches a number of fluid meters in a system) in a location accessible and/or visible by a user. The predictive failure analyzer 147 can perform the calculations to determine which color to display and transmit this information to the network-enabled standalone device and/or the network-enabled standalone device can receive the raw measurements from the sensor data server 140 and/or the magnetic field sensor 600 and perform the calculations described above to determine the color to display. Thus, the network-enabled standalone device can function as a leak notification device that provides a user with a simple to understand leak status of a subsystem.

Thus, the magnetic field sensor 600 described herein can function without any modification to the fluid meter 500 and/or any interference in the normal operation of the fluid meter 500. In addition, the PCB of the magnetic field sensor 600 can be designed to reduce interference in the measurements by the multi-axis sensors. For example, the ground plane on the PCB of the magnetic field sensor 600 may be positioned away from the multi-axis sensors so as to not affect the multi-axis sensor measurements.

Acoustic Sensor

Figure 10A:
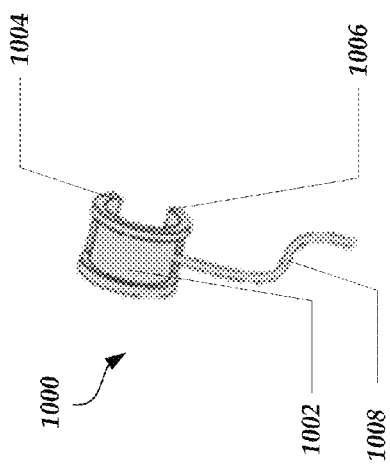
FIGS. 10A-10C illustrate an acoustic sensor configured to detect anomalous events.
Figure 10B:
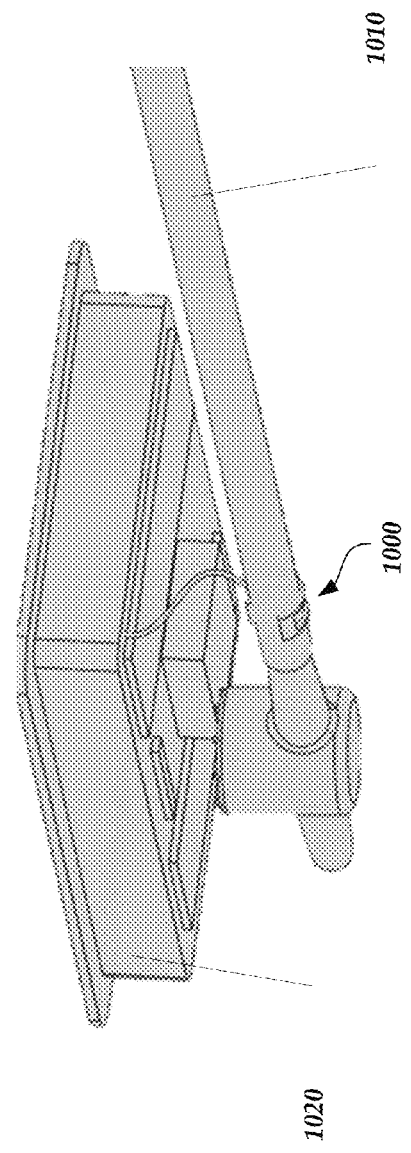
Figure 10C:
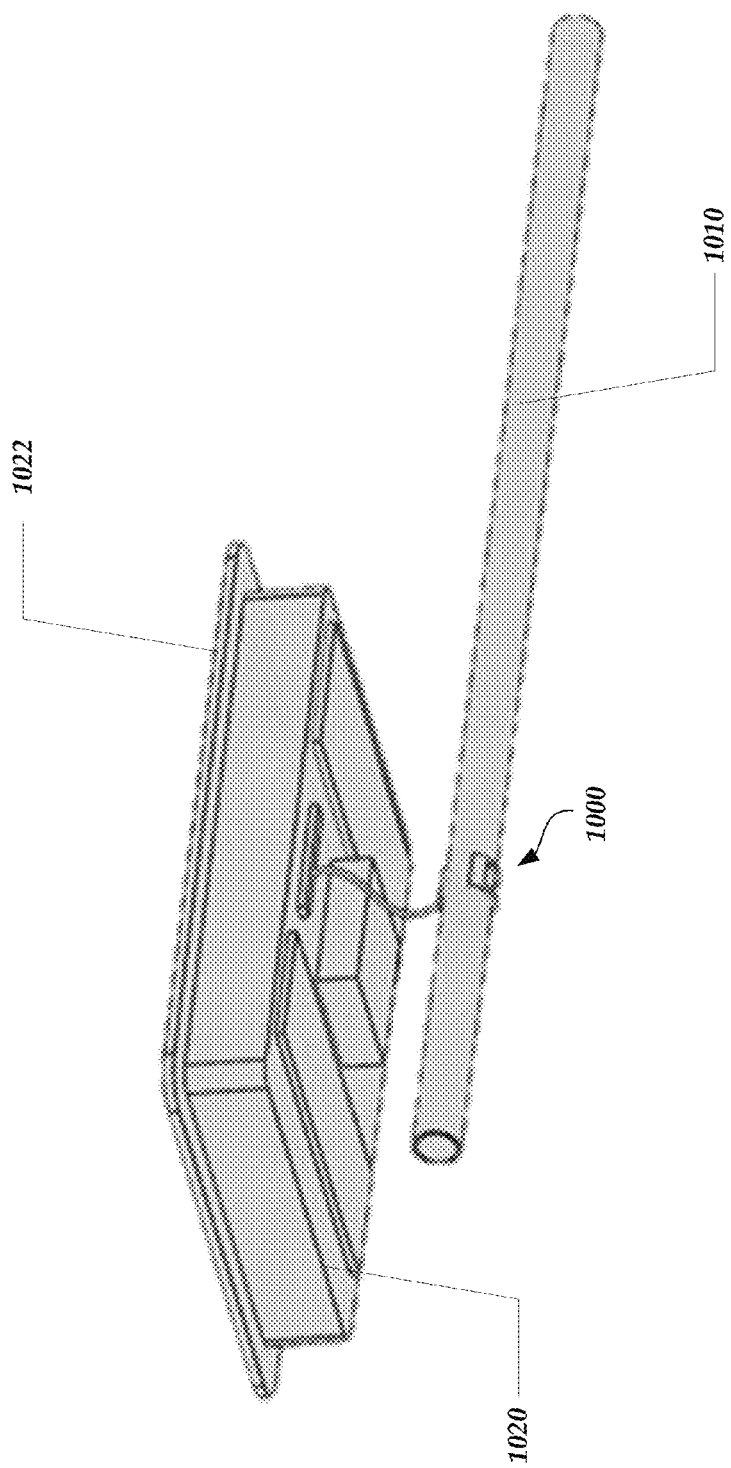

FIGS. 10A-10C illustrate an acoustic sensor 1000 configured to detect anomalous events. As illustrated in FIG. 10A, the acoustic sensor 1000 can include a curved portion 1002 that is cylindrical in shape. However, the curved portion 1002 includes a gap such that a bottom face 1006 of the curved portion 1002 does not couple with a top face 1004 of the curved portion 1002. This gap allows the acoustic sensor 1000 to snap on to a pipe 1010 or other fixture, as illustrated in FIG. 10B.

The acoustic sensor 1000 further includes a cable 1008 that transmits data measured by the acoustic sensor 1000 to a storage device and/or a transceiver (e.g., a wireless transceiver) for transmission to the sensor data server 140. For example, one end of the cable 1008 can couple with an outer face of the curved portion 1002 and another end of the cable 1008 can couple with a radio modem 1020, as illustrated in FIGS. 10B-10C. The cable 1008 can be rigid or flexible.

The radio modem 1020 can include a solar lid 1022, an internal battery, an internal transceiver, and/or an antenna. For example, the solar lid 1022 can include photovoltaic cells to convert light into energy to charge the internal battery. Energy generated by the photovoltaic cells and/or energy stored in the internal battery can be used to operate the internal transceiver. The internal transceiver can transmit data received via the cable 1008 to the sensor data server 140.

In an embodiment, the acoustic sensor 1000 provides acoustic anomaly detection. For example, the acoustic sensor 1000 can measure vibrations and a sequence of measured vibrations (e.g., measured magnitudes over time) can form a signal that corresponds to a signature. The sensor data store 148 may store a set of known signatures that are associated with known issues (e.g., leaks, types of malfunctions, etc.) or known normal operation of the particular equipment. The sensor data server 140 (e.g., predictive failure analyzer 147) can compare the measured signature with the known signatures to determine whether any known issues are occurring. This acoustic anomaly detection provided by the acoustic sensor 1000 can be combined or correlated with the magnetic anomaly detection provided by the magnetic field sensor 600 (e.g., using the magnetic sensors to measure the magnetic field generated by the fluid meter 500 and determine whether any leaks or malfunctions are occurring) to provide redundant and/or enhanced leak detection and/or equipment failure detection capabilities. The combination of magnetic anomaly detection and pipe physics in a correlative 3D temporal matrix can provide insight as to dendritic system dynamics.

Pressure Sensor

Figure 11:
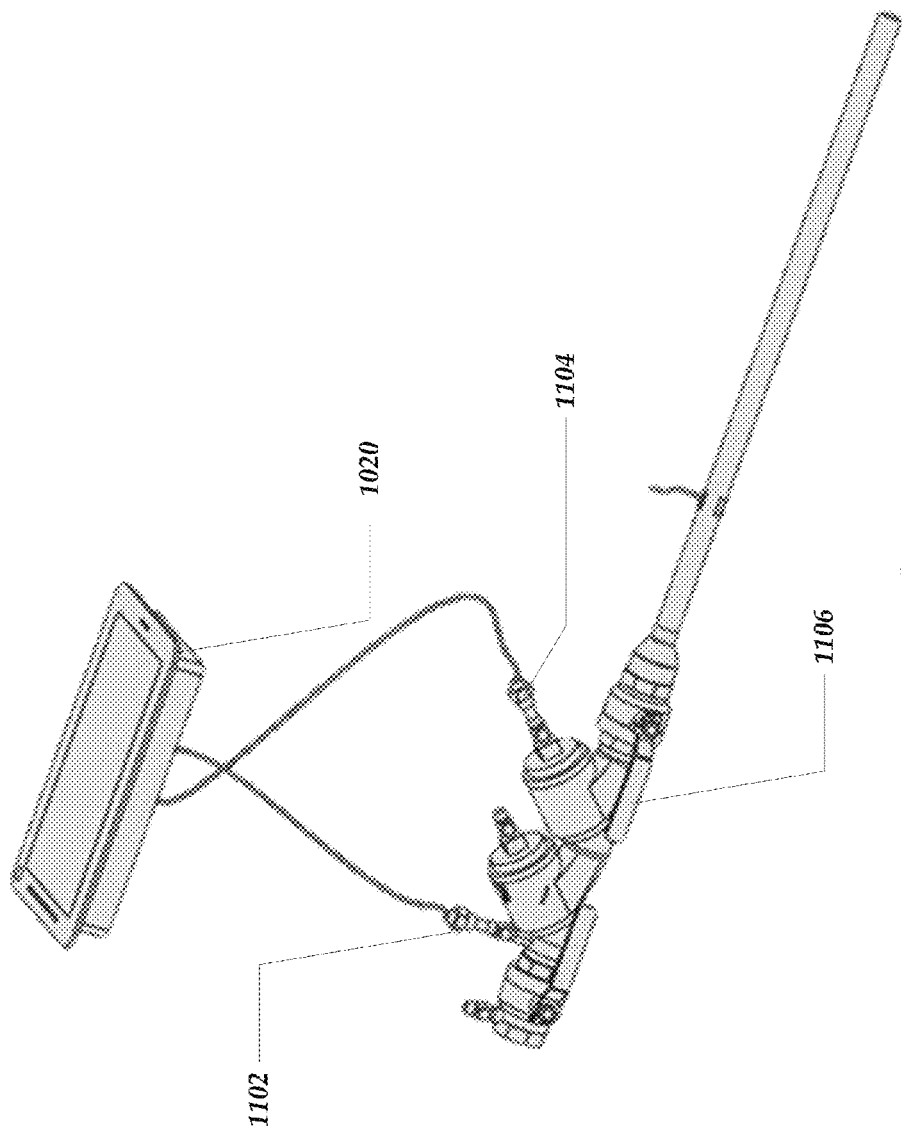
FIG. 11 illustrates a first pressure sensor and a second pressure sensor configured to monitor flow dynamics through a backflow prevention device.

FIG. 11 illustrates a first pressure sensor 1102 and a second pressure sensor 1104 configured to monitor flow dynamics through a backflow prevention device 1106. For example, the pressure sensors 1102 and 1104 can measure fluidic pressure (e.g., water pressure) through the backflow prevention device 1106. The pressure sensors 1102 and 1104, when used in conjunction with other pressure sensors in other portions of the dendritic containment and control system, can be used to detect flow patterns, leaks, component failure (e.g., failure of the backflow prevention device 1106), time for maintenance to be completed, and/or the like as described herein.

In an embodiment, one of both of the pressure sensors 1102 and 1104 are coupled with the radio modem 1020. Thus, measurements taken by the pressure sensors 1102 and 1104 can be transmitted wirelessly to the sensor data server 140 for analysis.

The first pressure sensor 1102 and the second pressure sensor 1104 may be configured to fit onto check valve release ports of the backflow prevention device 1106. The first pressure sensor 1102 and the second pressure sensor 1104 can measure the water pressure differential between the check valves of the backflow prevention device 1106. This water pressure differential may be indicative of the activity, condition, performance and/or function of the dendritic water system and/or the apparatus and appliances attached thereto.

Encapsulated Sensor System

Figure 12:
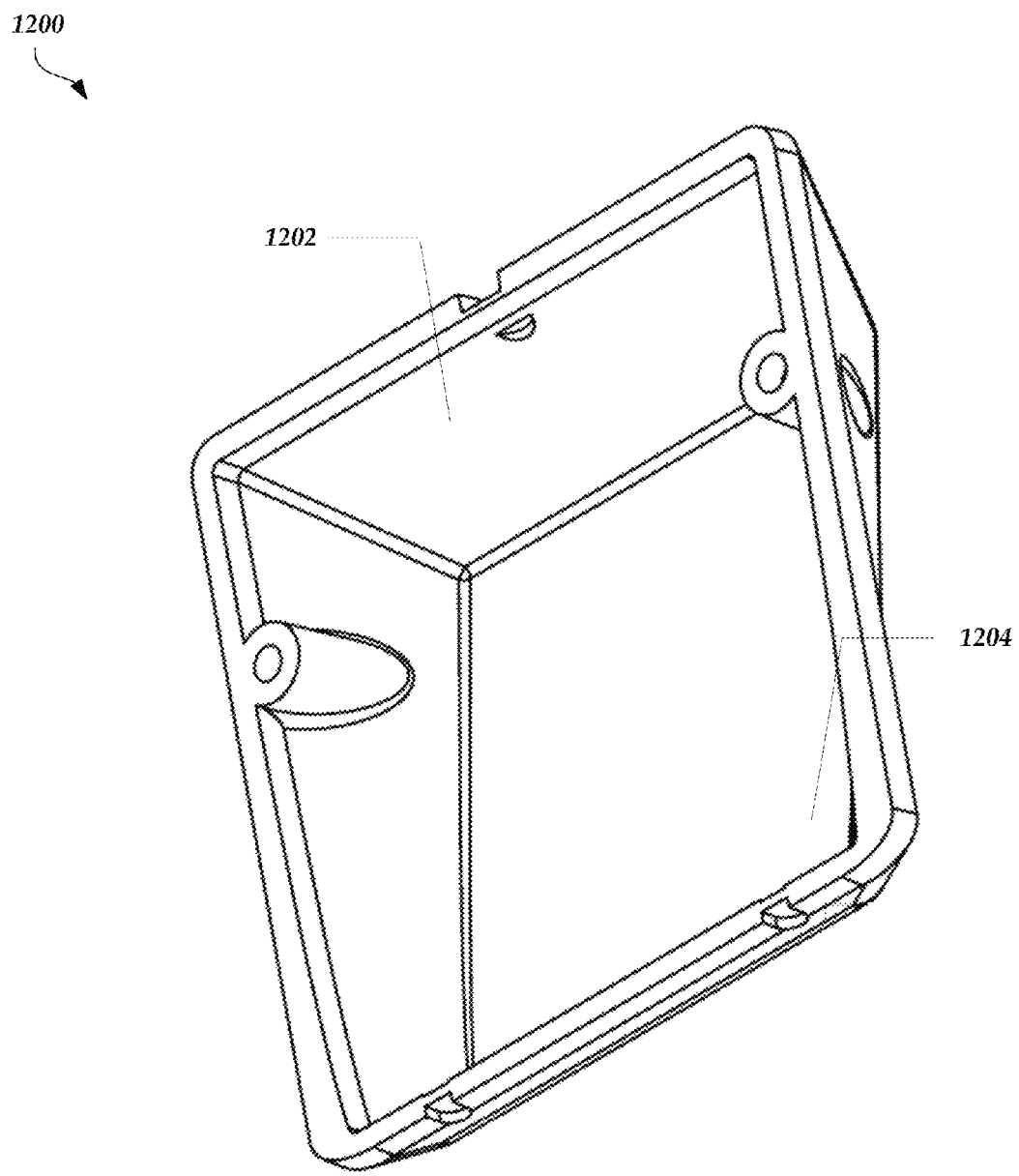
FIG. 12 illustrates a side rear perspective view of an encapsulated sensor system.

FIG. 12 illustrates a side rear perspective view of an encapsulated sensor system 1200. As illustrated in FIG. 12, a sensor back plate of the encapsulated sensor system 1200 is removed to depict an interior cavity of the encapsulated sensor system 1200. A printed circuit board (PCB) that includes sensors and other components can be designed to abut a top interior surface 1202 of the encapsulated sensor system 1200 and a front interior surface 1204 of the encapsulated sensor system 1200, as described in greater detail below.

Figure 13:
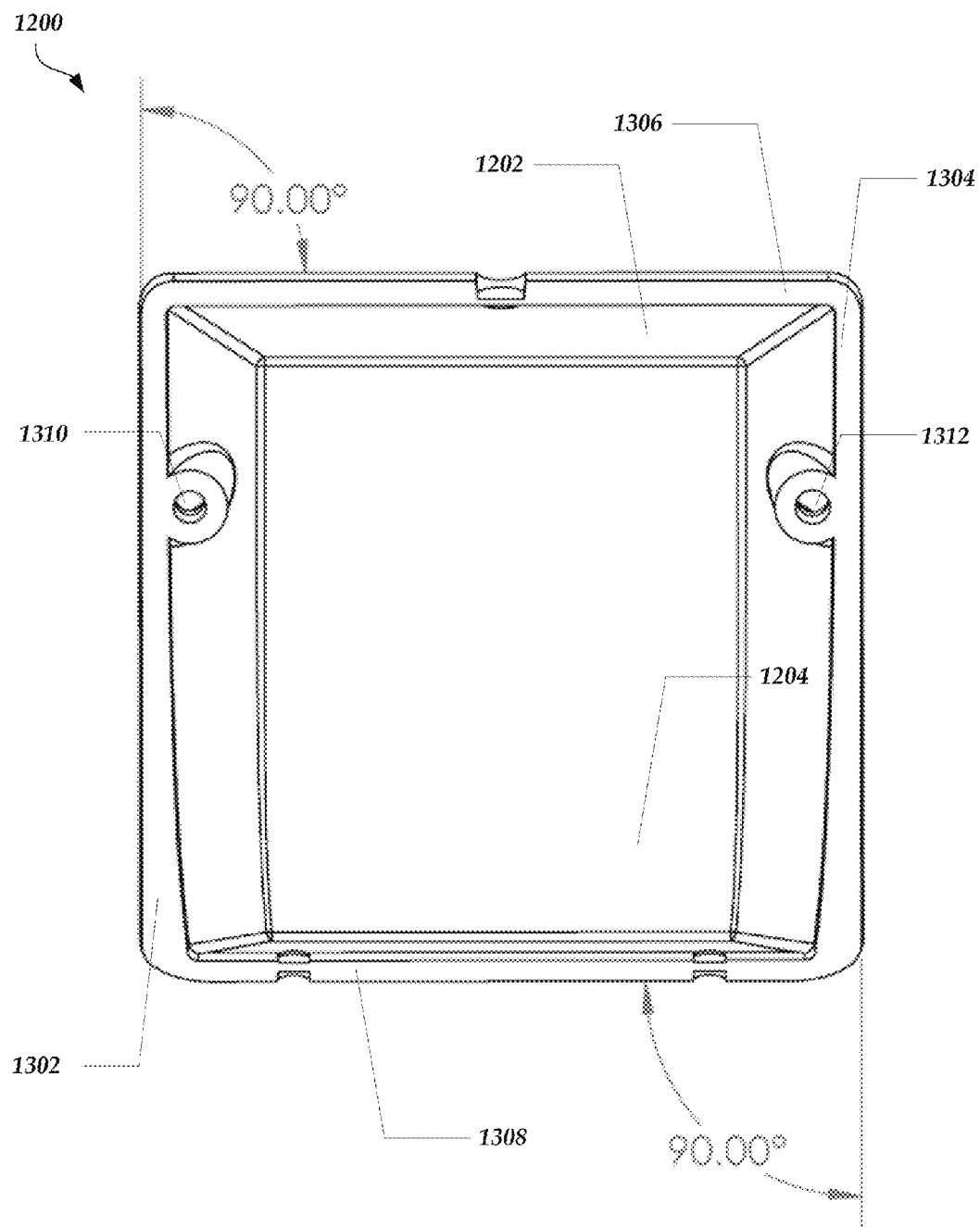
FIG. 13 illustrates a rear perspective view of the encapsulated sensor system of FIG. 12.

FIG. 13 illustrates a rear perspective view of the encapsulated sensor system 1200. As illustrated in FIG. 13, a left rear wall 1302 of the encapsulated sensor system 1200 is perpendicular to a top rear wall 1306 of the encapsulated sensor system 1200 and a bottom rear wall 1308 of the encapsulated sensor system 1200. Likewise, a right rear wall 1304 of the encapsulated sensor system 1200 is perpendicular to the top rear wall 1306 and the bottom rear wall 1308.

The encapsulated sensor system 1200 includes openings 1310 and 1312 to allow for the mounting of the encapsulated sensor system 1200 to a surface (e.g., a pool, a spa, etc.). For example, the openings 1310 and 1312 can accommodate mechanical fasteners (e.g., screws) to mount the encapsulated sensor system 1200 to a surface. If the encapsulated sensor system 1200 is placed in a pool or spa, an adhesive (e.g., two part putty) can be applied to the back plate (e.g., a finished epoxy filler) of the encapsulated sensor system 1200 and the encapsulated sensor system 1200 can be placed against tiles that line the wall of the pool or spa below and above the water line (e.g., a top portion of the encapsulated sensor system 1200 can be above the water line and a bottom portion of the encapsulated sensor system 1200 can be below the water line).

The front interior surface 1204 of the encapsulated sensor system 1200 can be sufficiently large enough to fit a portion of the PCB without large gaps near the edges of the front interior surface 1204. An outer surface of the PCB (e.g., the portion of the PCB that abuts the front interior surface 1204) may include sensors that abut against the front interior surface 1204. The front interior surface 1204 is flat and the outer surface of the PCB is also flat, and thus the outer surface of the PCB is co-planar with the front interior surface 1204. In an embodiment, the PCB is positioned as close to the front interior surface 1204 as possible to increase the proximity of the sensors on the PCB to the environment exterior to the encapsulated sensor system 1200.

The interior cavity of the encapsulated sensor system 1200 can have a large enough volume to include one or more batteries (e.g., a AA battery) used to power the components on the PCB. As described below, the one or more batteries may be coupled with the PCB.

Figure 14:
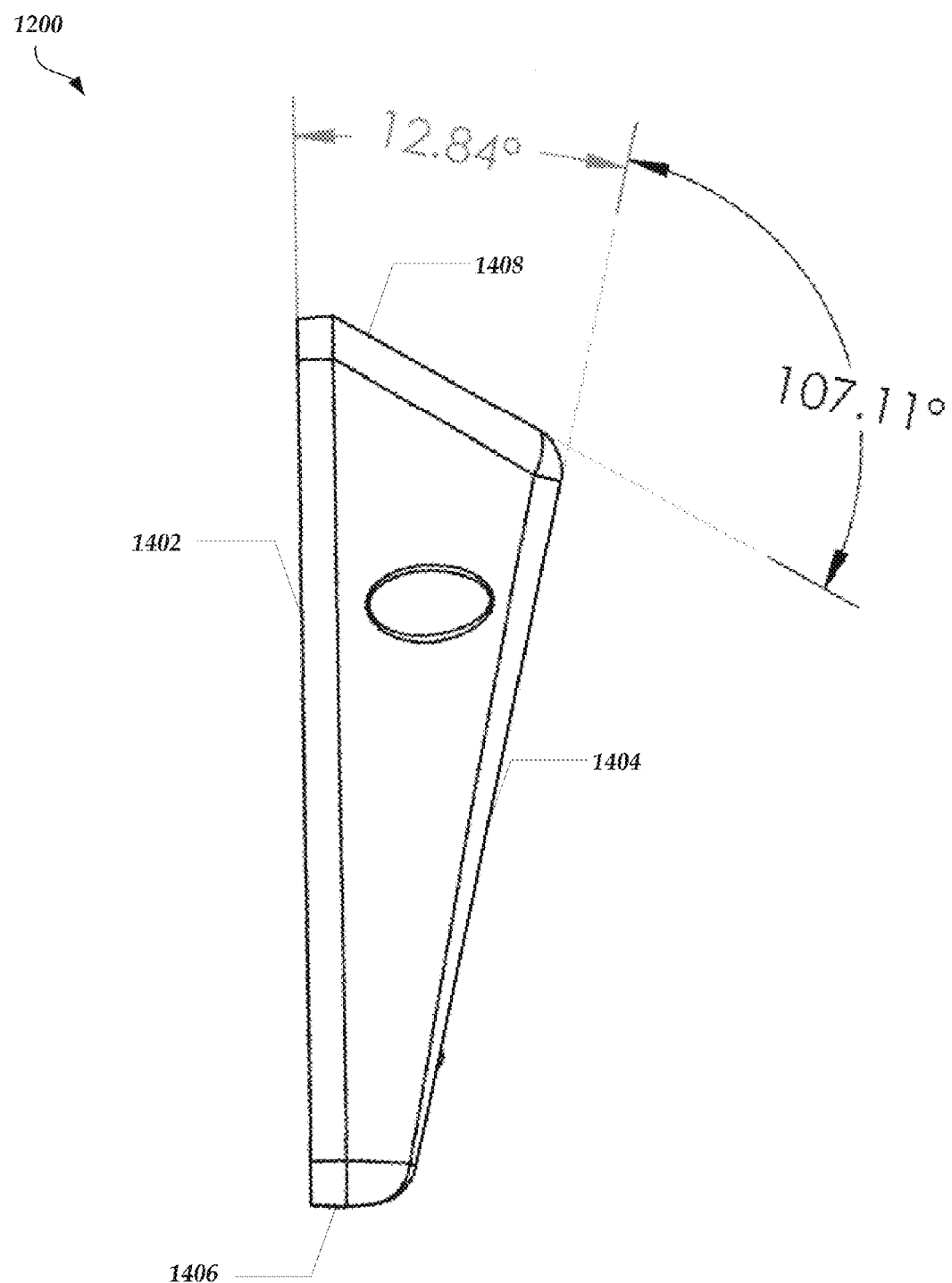
FIG. 14 illustrates a side perspective view of the encapsulated sensor system of FIG. 12.

FIG. 14 illustrates a side perspective view of the encapsulated sensor system 1200. As illustrated in FIG. 14, a rear surface 1402 of the encapsulated sensor system 1200 and a front surface 1404 of the encapsulated sensor system 1200 are not parallel. Rather, the rear surface 1402 of the encapsulated sensor system 1200 extends vertically along a longitudinal axis of the encapsulated sensor system 1200 from a base 1406 of the encapsulated sensor system 1200. On the other hand, the front surface 1404 of the encapsulated sensor system 1200 extends from the base 1406 at an angle relative to the longitudinal axis, such as between about −5 degrees and about −80 degrees (e.g., at least about: −5 degrees, −20 degrees, −35 degrees, −50 degrees, −65 degrees, −80 degrees, values in between, or otherwise).

Furthermore, a top surface 1408 of the encapsulated sensor system 1200 extends from the rear surface 1402 of the encapsulated sensor system 1200 to the front surface 1404 of the encapsulated sensor system 1200 at an angle relative to a latitudinal axis of the encapsulated sensor system 1200, such as between about −20 degrees and about −30 degrees (e.g., at least about: −20 degrees, −22.5 degrees, −25 degrees, −27.5 degrees, −30 degrees, values in between, or otherwise). Thus, the top surface 1408 is downward sloping from the top end of the rear surface 1402 to the top end of the front surface 1404.

Figure 15:
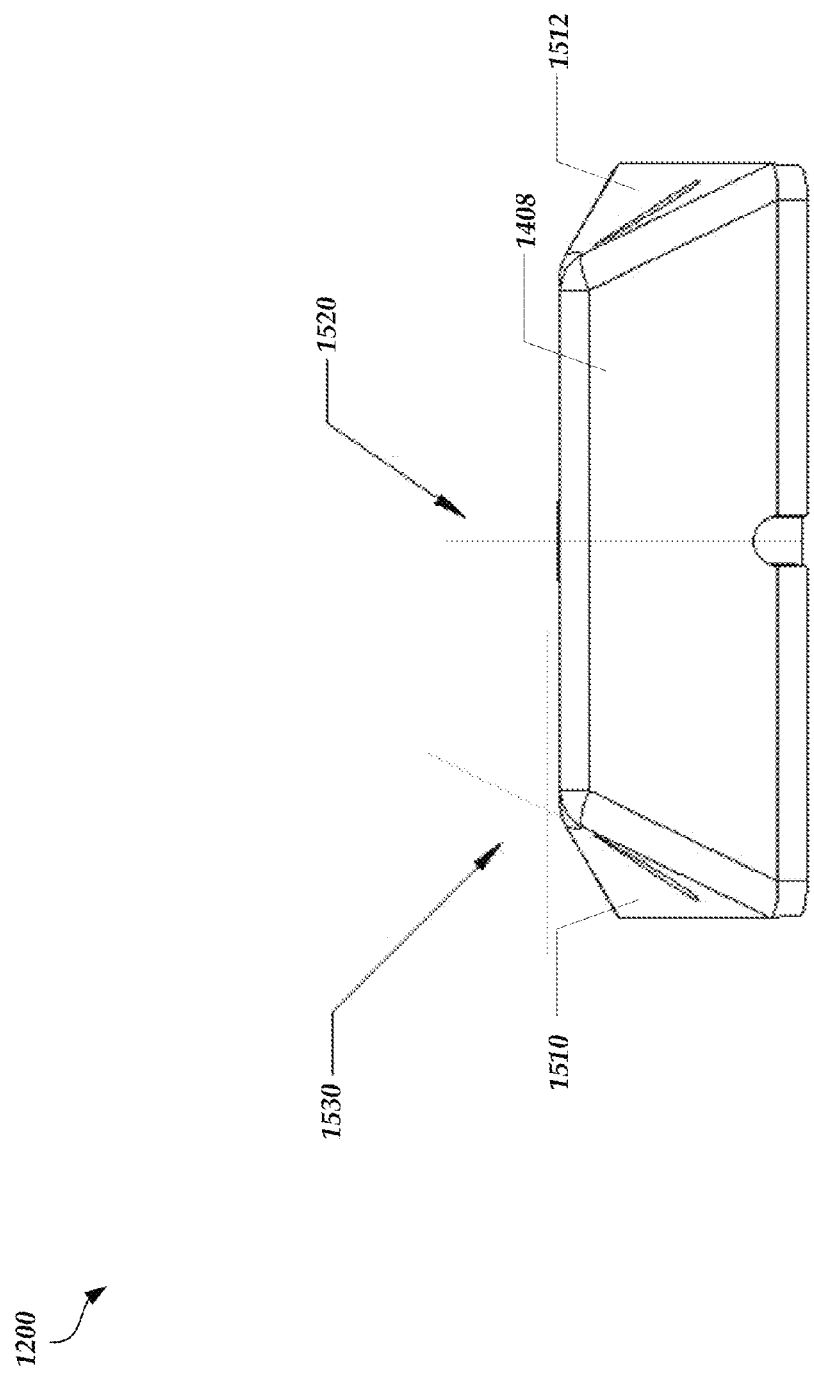
FIG. 15 illustrates a top perspective view of the encapsulated sensor system of FIG. 12.

FIG. 15 illustrates a top perspective view of the encapsulated sensor system 1200. As illustrated in FIG. 15, the top surface 1408 can form a nearly trapezoidal shape, with a left surface 1510 and a right surface 1512 of the encapsulated sensor system 1200 angled toward a center line 1520 of the encapsulated sensor system 1200. For example, an angle 1530 symmetric about the center line 1520 formed by the left surface 1510 and the top surface 1408 can be between 90 and 180 degrees.

The angled left surface 1510, right surface 1512, top surface 1408, and front surface 1404 may provide several benefits. For example, an antenna can be embedded on the PCB and positioned adjacent to an interior portion of the top surface 1408. The top surface 1408 may be angled such that the antenna projects transmissions at an angle sufficient to reach the sensor data server 140 or a relay (or a router) in communication with the sensor data server 140. In some embodiments, the top surface 1408 is angled to optimize the range and/or power of radio transmissions via the antenna, especially if the encapsulated sensor system 1200 is placed in a wet environment. For example, if the encapsulated sensory system 1200 is placed in or near a pool or generally outdoors, water from the pool and/or rain can remain on the top surface 1408 if designed to be parallel to the flat base 1406 of the encapsulated sensor system 1200. The downward sloping angle of the top surface 1408, however, allows the water to slide off the top surface 1408 and onto a region beneath the encapsulated sensor system 1200. Given that water or other liquids can absorb portions of radio transmissions, the automatic removal of liquids from the transmission region of the encapsulated sensor system 1200 can improve transmission performance.

As another example, because the encapsulated sensor system 1200 may be located in proximity to humans or animals (e.g., in a pool), there is a concern that contact from humans or animals could cause the encapsulated sensor system 1200 to become dislodged. However, the angled surfaces of the encapsulated sensor system 1200 may make it difficult for fingers or paws to grasp a surface of the encapsulated sensor system 1200 to peel the encapsulated sensor system 1200 from or otherwise dislodge the encapsulated sensor system 1200 from the surface on which the encapsulated sensor system 1200 is mounted.

As another example, the angled front surface 1404 can allow the encapsulated sensor system 1200 to shed water or other fluids. Typical encapsulated sensor systems may have a top surface and a front surface that meet at a 90 degree angle. Thus, the front surface is oriented vertically, perpendicular to a fluid line. However, having a surface perpendicular to the fluid line may not be ideal for achieving a strong contact between the environment and sensors and shedding fluid from the area of contact. For example, prolonged exposure to fluids can damage the sensors on the PCB. Thus, the fluid shedding feature provided by the angled front surface 1404 can extend the life of the sensors on the PCB. In addition, while prolonged exposure to fluids can affect the performance of the sensors, it may still be important for the front surface 1404 to be properly wetted so that there is sufficient contact between the sensors and the environment to provide for more precise gas-fluid interface measurements by the sensors. The angled front surface 1404, the left surface 1510, and/or the right surface 1512 can aid in the proper wetting of the front surface 1404.

In an embodiment, the front surface 1404, the left surface 1510, and/or the right surface 1512 is transparent or semi-transparent (e.g., 5% opaque, 10% opaque, 15% opaque, 20% opaque, 25% opaque, 30% opaque, etc.) to allow lights (e.g., light emitting diodes (LEDs)) mounted to the PCB positioned in the interior of the encapsulated sensor system 1200 the ability to indicate a status of the encapsulated sensor system 1200 and/or other information during and/or after setup. For example, the lights can indicate any radio performance issues, a power status, a battery status, and/or the like.

Furthermore, the transparent or semi-transparent characteristic of the surfaces 1404, 1510, and/or 1512 can allow the transport of analytical light from an LED photometric system constructed of components on the PCB. For example, the LED photometric system can implement total internal reflection (TIR) spectroscopy techniques to detect the levels of chemical substances in fluid flowing exterior to the encapsulated sensor system. Such chemical substances can include chlorine, salt, and/or the like.

Figure 16:
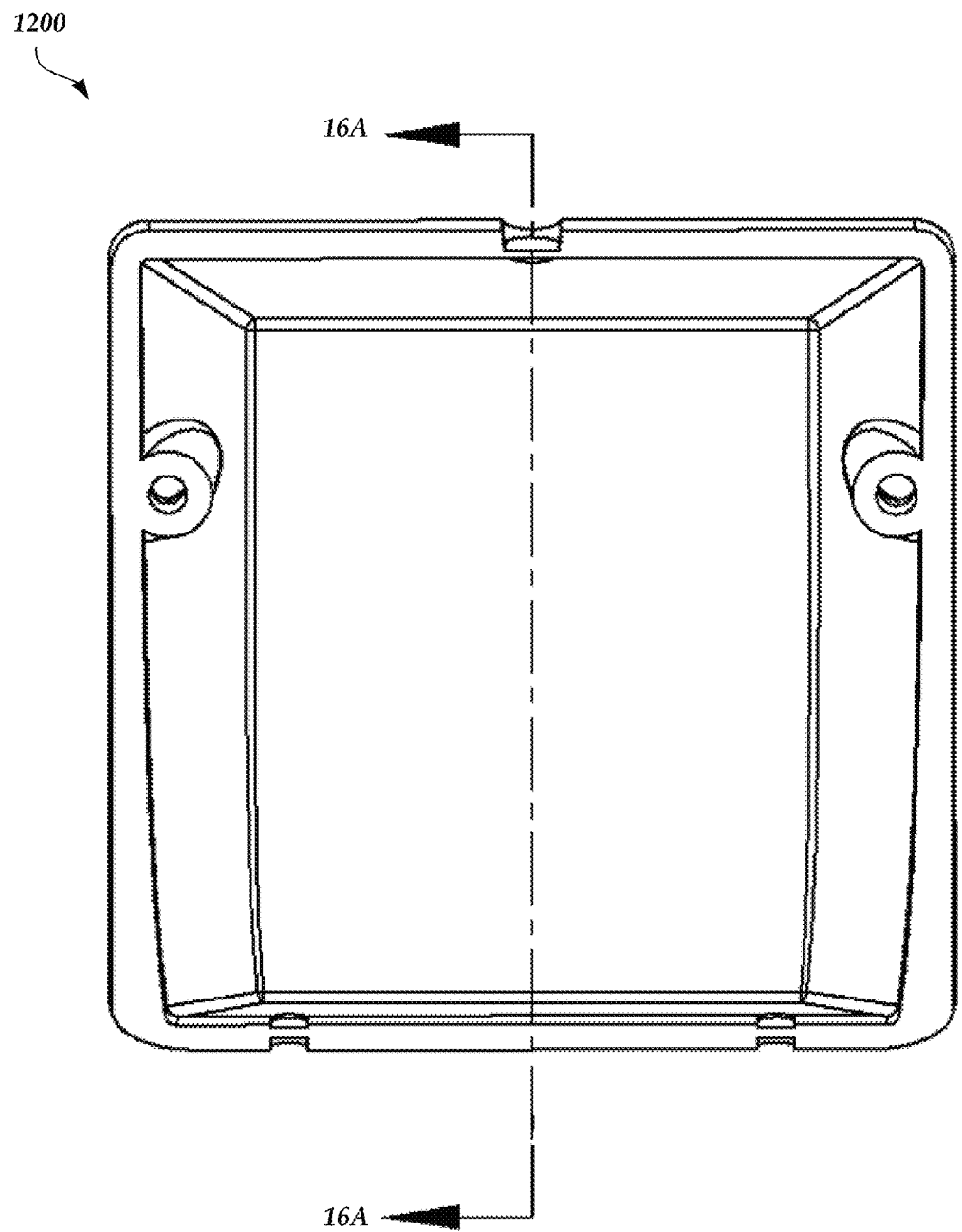
FIG. 16 illustrates another rear perspective view of the encapsulated sensor system of FIG. 12.

FIG. 16 illustrates another rear perspective view of the encapsulated sensor system 1200. As illustrated in FIG. 16, a line 16A-16A is referenced that extends from a base of the encapsulated sensor system 1200 to a top of the encapsulated sensor system 1200 through a central axis of the encapsulated sensor system 1200.

Figure 17:
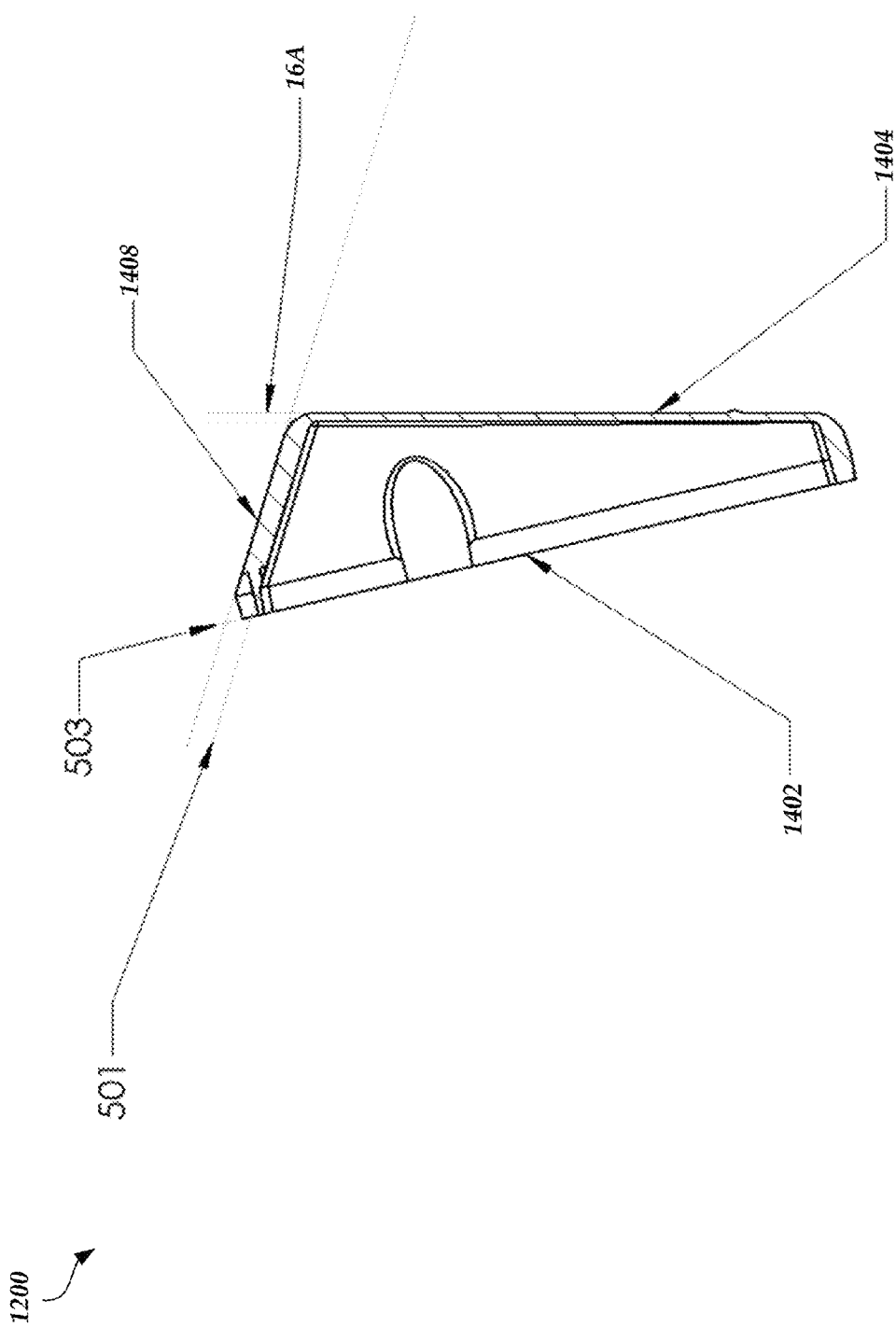
FIG. 17 illustrates a cross-sectional view of the encapsulated sensor system of FIG. 12 shown in FIG. 16 taken along a line.

FIG. 17 illustrates a cross-sectional view of the encapsulated sensor system 1200 shown in FIG. 16 taken along the line 16A-16A. As illustrated in FIG. 17 and described herein, an angle formed between the top surface 1408 and the front surface 1404 is greater than 90 degrees to facilitate the proper orientation of the antenna on the PCB for signal transmission and to shed any fluidic materials when the encapsulated sensor system 1200 is mounted to the wall of a fluidic container (e.g., a pool) at the gas-fluid interface (e.g., at the water line) via the rear surface 1402.

A thickness of the wall along the front surface 1404 (e.g., the width from the interior front surface 1204 to the exterior of the front surface 1404) may be thinner than the walls along the other surfaces 1408, 1510, and 1512. By including a thinner wall along the front surface 1404, the sensors on the PCB that abut the interior front surface 1204 can be positioned closer to the environment exterior to the encapsulated sensor system 1200, thereby allowing for a stronger contact between the environment and the sensors and thus more sensitive measurements to be taken by the sensors.

In an embodiment, the encapsulated sensor system 1200 is backfilled with epoxy or a similar substance to seal the encapsulated sensor system 1200. Use of the epoxy or the similar substance may allow for the thin designed described above by reducing the amount of plastic needed to seal the encapsulated sensor system 1200 and separating the antenna and sensors of the PCB from the environment exterior to the encapsulated sensor system 1200.

Figure 18:
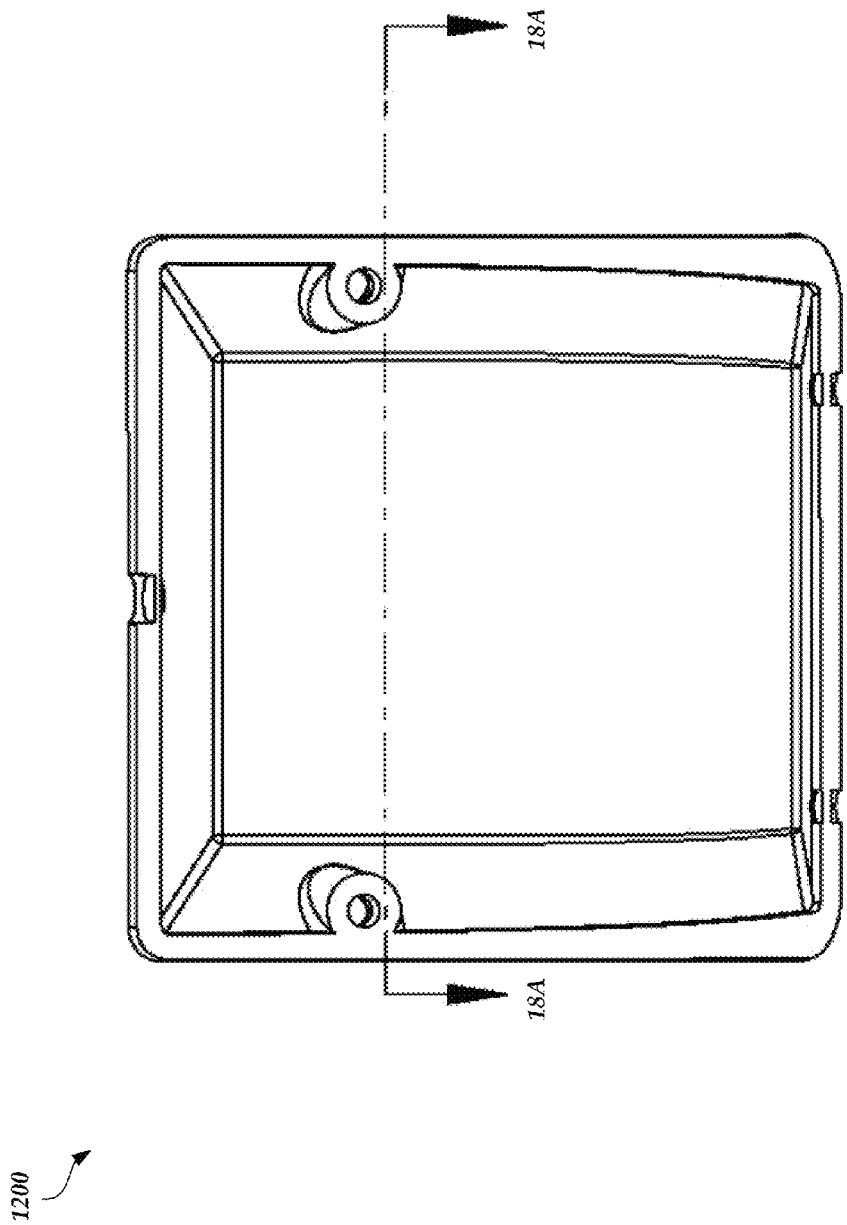
FIG. 18 illustrates another rear perspective view of the encapsulated sensor system of FIG. 12.

FIG. 18 illustrates another rear perspective view of the encapsulated sensor system 1200. As illustrated in FIG. 18, a line 18A-18A is referenced that extends from a left end of the encapsulated sensor system 1200 to a right end of the encapsulated sensor system 1200 through an upper portion of the encapsulated sensor system 1200.

Figure 19:
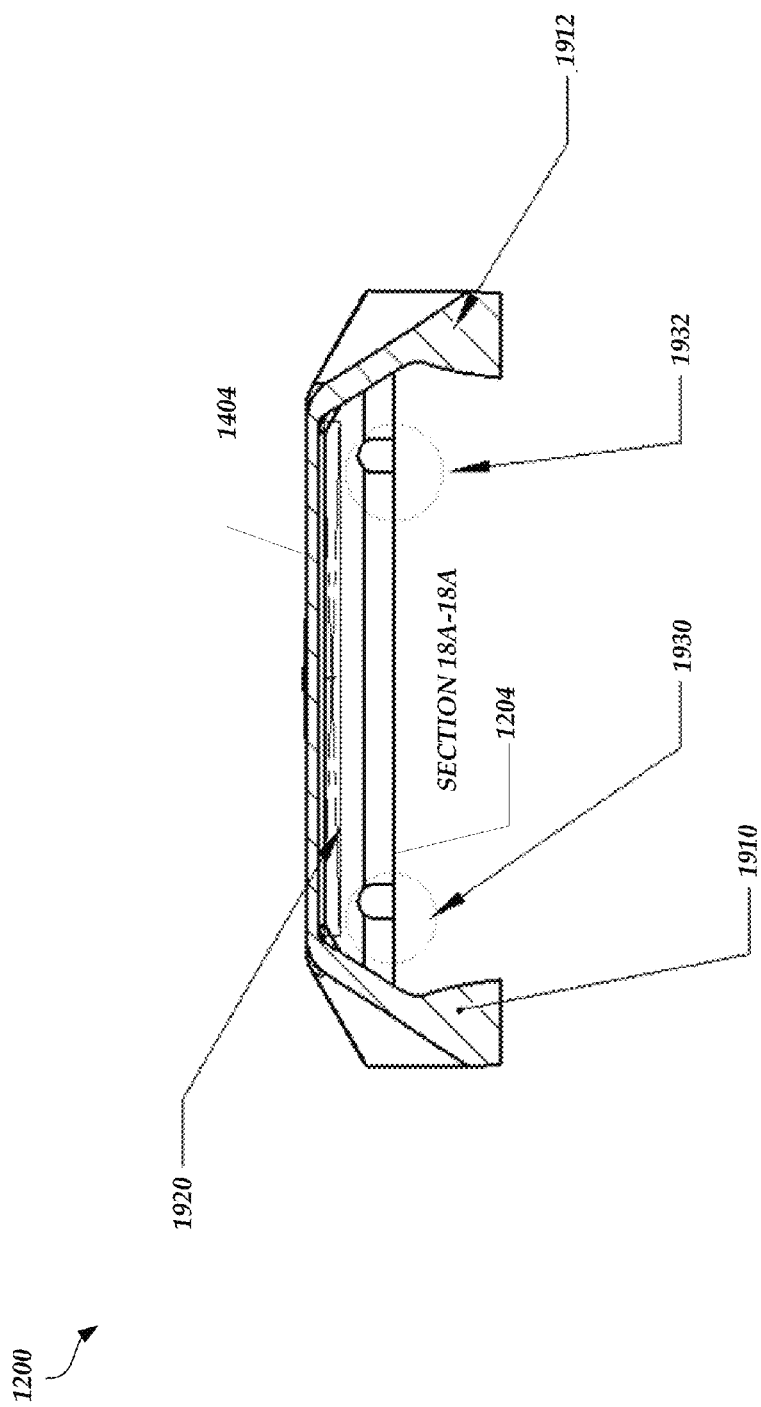
FIG. 19 illustrates a cross-sectional view of the encapsulated sensor system of FIG. 12 shown in FIG. 18 taken along a line.

FIG. 19 illustrates a cross-sectional view of the encapsulated sensor system 1200 shown in FIG. 18 taken along the line 18A-18A. As illustrated in FIG. 19 and as described above, a thickness of the wall along the front surface 1404 (e.g., a width between the interior front surface 1204 and the exterior of the front surface 1404) is thinner than the thickness of the walls along other portions of the encapsulated sensor system 1200, such as the thickness of the walls along the left surface 1510 and the right surface 1512 represented by thickness 1910 and 1912, respectively.

A PCB 1920 is depicted as being positioned adjacent to the interior front surface 1204. Furthermore, holes 1930 and 1932, at the base 1406 of the encapsulated sensor system 1200 are depicted. The holes 1930 and 1932 can be used to secure the encapsulated sensor system 1200 to a surface via mechanical fasteners.

Figure 20:
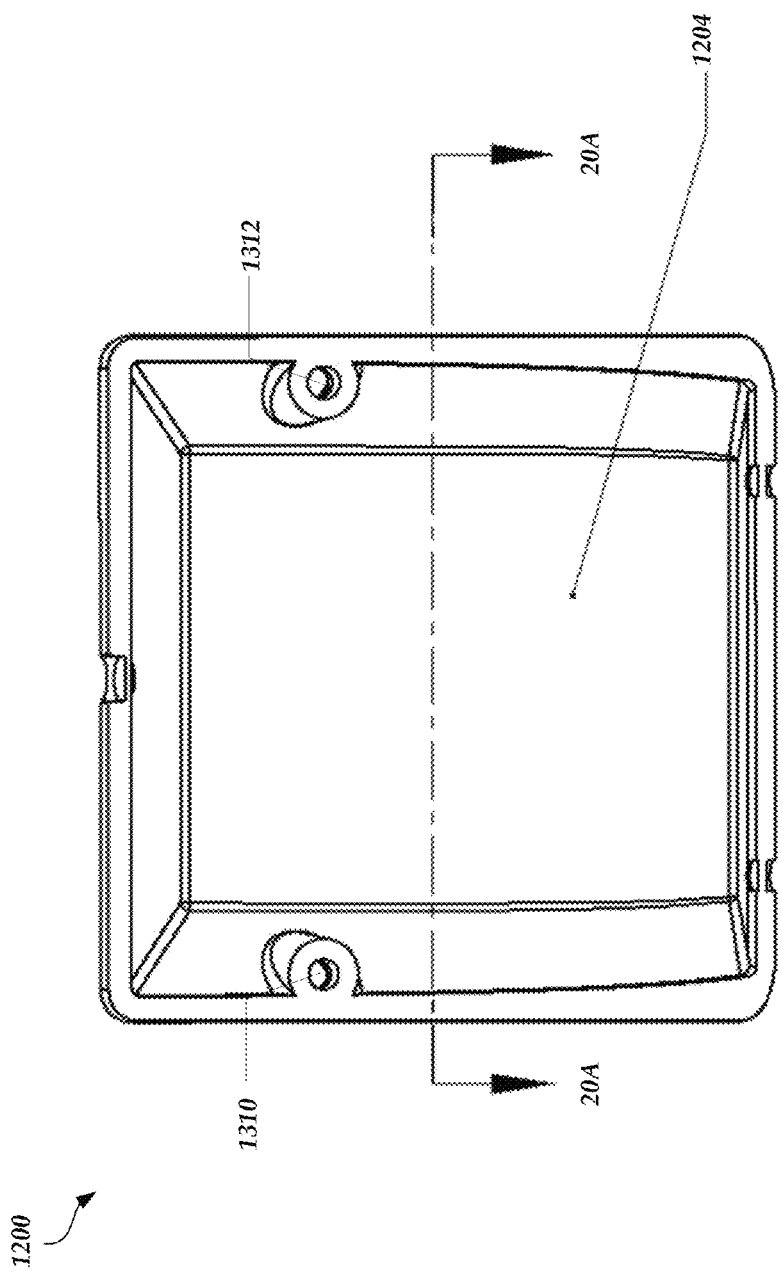
FIG. 20 illustrates another rear perspective view of the encapsulated sensor system of FIG. 12.

FIG. 20 illustrates another rear perspective view of the encapsulated sensor system 1200. As illustrated in FIG. 20, a line 20A-20A is referenced that extends from a left end of the encapsulated sensor system 1200 to a right end of the encapsulated sensor system 1200 through a central portion of the encapsulated sensor system 1200, below the holes 1310 and 1312.

Figure 21:
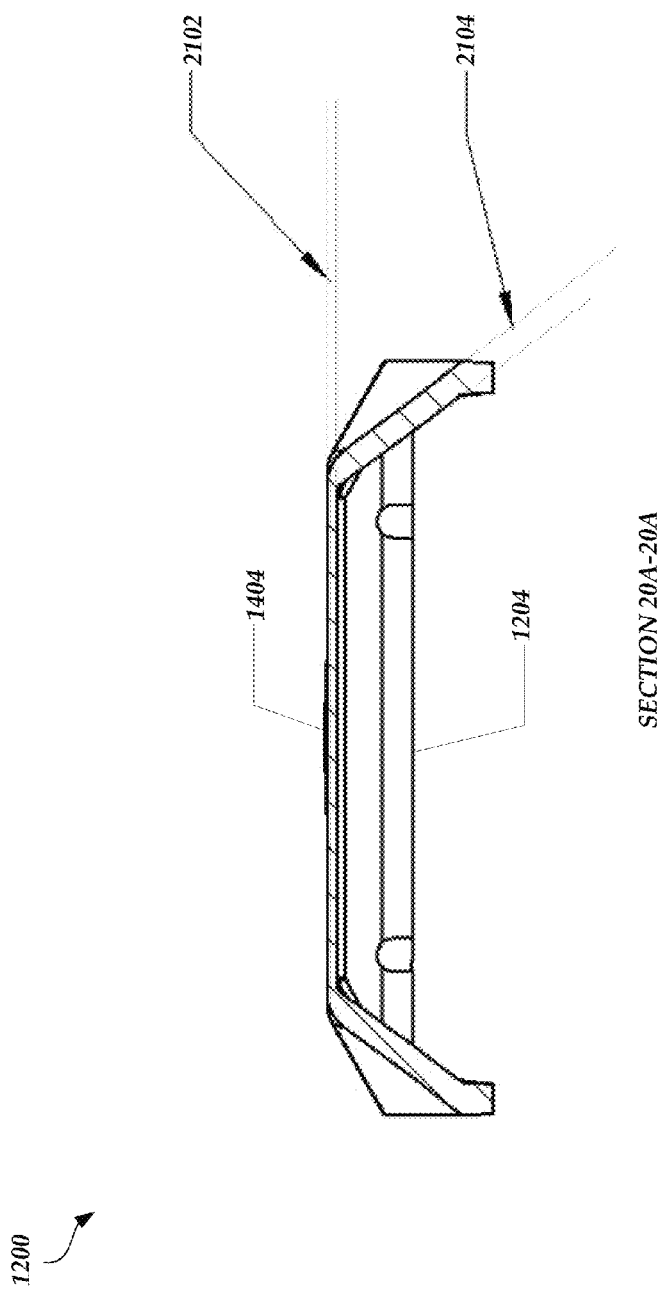
FIG. 21 illustrates a cross-sectional view of the encapsulated sensor system of FIG. 12 shown in FIG. 20 taken along a line.

FIG. 21 illustrates a cross-sectional view of the encapsulated sensor system 1200 shown in FIG. 20 taken along the line 20A-20A. As illustrated in FIG. 21, a thickness 2104 of the walls along the left surface 1510 and/or the right surface 1512 may be thinner in cross-section 20A-20A than in cross section 18A-18A. However, the thickness 2102 of the wall along the front surface 1404 may remain constant or nearly constant. Maintaining a uniform or nearly uniform, relatively thin thickness of the wall along the front surface 1404 may be important to ensure that the dielectric field sensors (e.g., the sensors included on the outer side of the PCB) and/or the LED photometric system can take more sensitive measurements.

Figure 22:
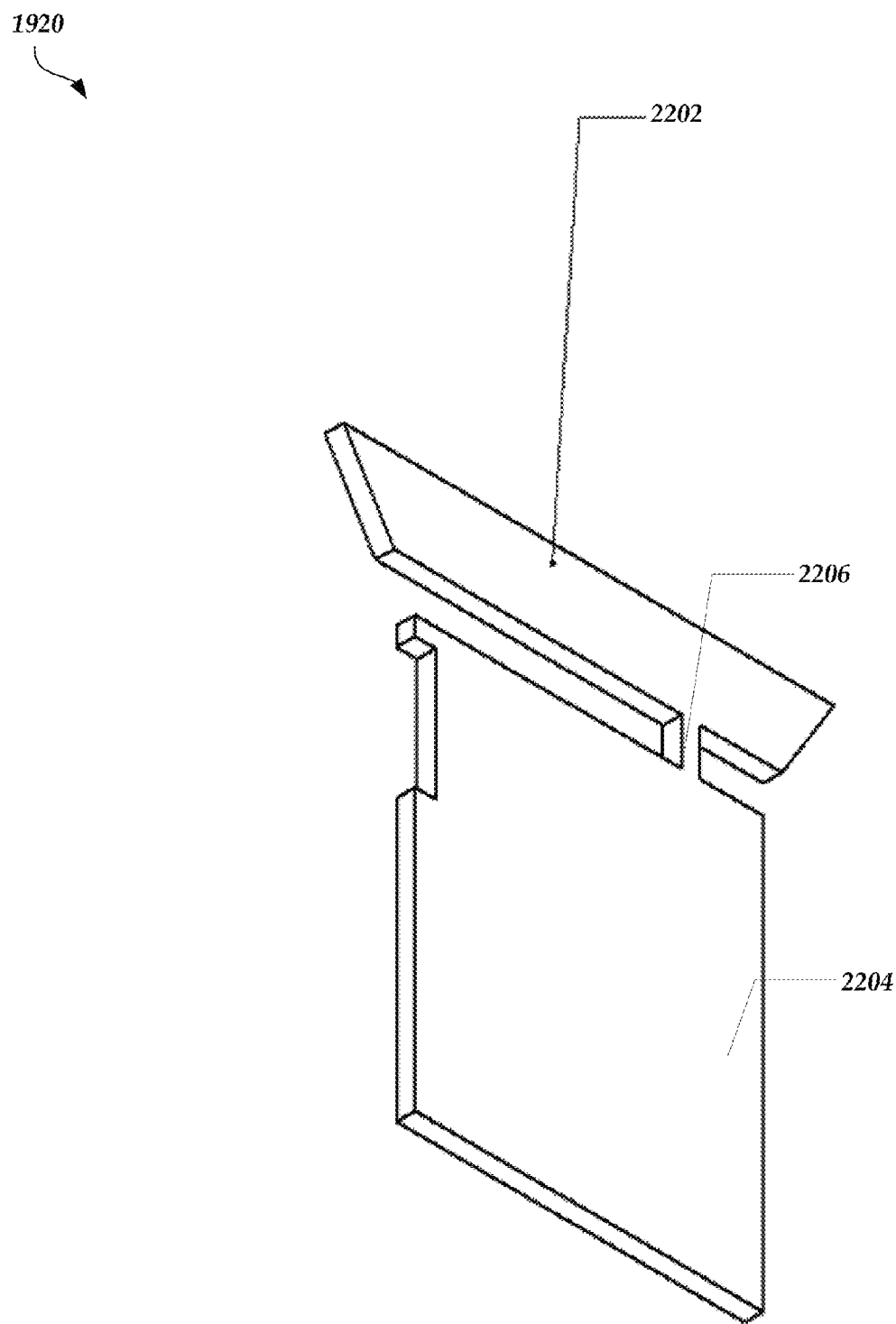
FIG. 22 illustrates the PCB of FIG. 19 that can be embedded within the interior cavity of the encapsulated sensor system of FIG. 12.

FIG. 22 illustrates the PCB 1920 that can be embedded within the interior cavity of the encapsulated sensor system 1200. The PCB 1920 can include an antenna 2202 and a bottom portion 2204 coupled to the antenna 2202 by a support member 2206. In an embodiment, the antenna 2202 is configured to transmit data collected by the sensors of the PCB accordingly to Hadamard sampling techniques.

Figure 23:
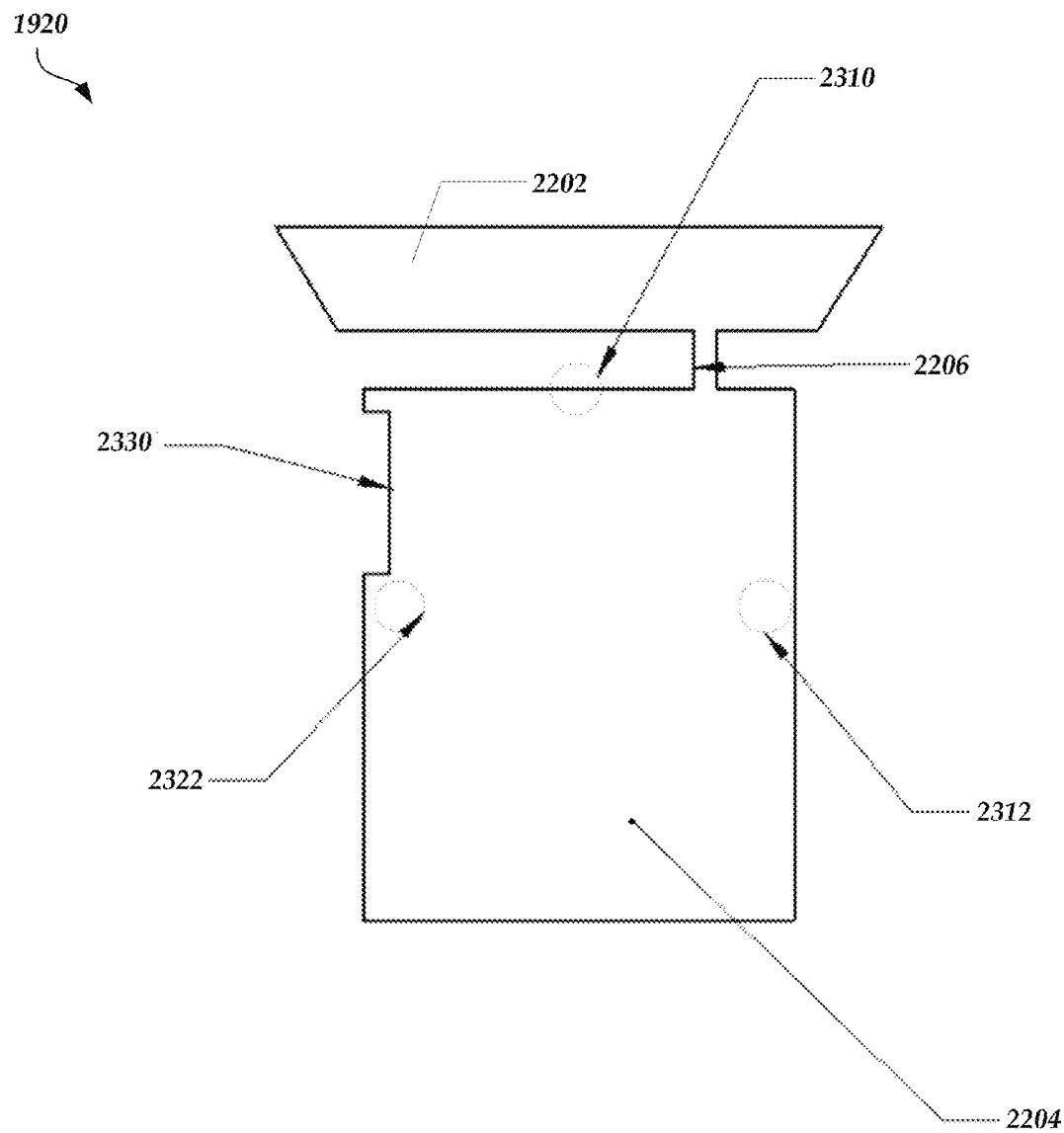
FIG. 23 illustrates a front perspective view of the PCB of FIG. 19 prior to insertion within the interior cavity of the encapsulated sensor system of FIG. 12.

FIG. 23 illustrates a front perspective view of the PCB 1920 prior to insertion within the interior cavity of the encapsulated sensor system 1200. As illustrated in FIG. 23, the PCB 1920 includes LEDs 2310 and 2312 for emitting light that can signal to a user a status of the encapsulated sensor system 1200 and/or for emitting light to take analytical measurements using TIR spectroscopy techniques. The PCB 1920 also includes a photoreceiver 2322 to receive any reflected light waves emitted by LED 2312 (e.g., any light waves emitted by the LED 2312 minus a portion absorbed by the environment and/or refracted by the fluid).

For example, the LED 2312 can emit a light wave in a direction toward the transparent or semi-transparent front surface 1404. If the light wave is entirely reflected (as detected by the photoreceiver 2322) except for a small amount of the electromagnetic energy that is absorbed by the front surface 1404 and/or the adjacent material (e.g., the fluid exterior to the front surface 1404) or a threshold percentage of the light is reflected, then this may indicate that a fluid level exterior to the encapsulated sensor system 1200 is greater than a threshold value (e.g., higher than a latitudinal level of the LED 2312 and the photoreceiver 2322). The threshold value may represent a lowest acceptable fluid level such that any further reduction in the fluid level should result in an automatic increase in the fluid level (e.g., by opening a valve).

In addition, an amount of light reflected to the photoreceiver 2322 (e.g., as a percentage of a total amount of light emitted by the LED 2312, except for a small amount of the electromagnetic energy that may be expected to be absorbed by the fluid exterior to the front surface 1404) can indicate a level of chemical substance in the fluid exterior to the encapsulated sensor system 1200. The LED 2312 can emit light at different wavelengths to be able to detect different chemical substances and/or multiple LEDs 2312 can be mounted to the PCB 1920, where each LED 2312 emits light at a different wavelength and is enabled depending on the chemical substance to analyze. The sensor data server 140 can perform the analysis using data provided by the encapsulated sensor system 1200 and, for example, Beer's Law or other similar techniques. For example, a first angle of refraction may indicate that chlorine in the fluid is at a first level, a second angle of refraction may indicate that chlorine in the fluid is as a second level, and so on.

The bottom portion 2204 of the PCB 1920 may include an indentation or depression 2330. The indentation 2330 may be of the same shape as a magnetic switch such that the magnetic switch mates with the PCB 1920 at the indentation 2330. The magnetic switch can be used to control the features of the encapsulated sensor system 1200 without having a switch protrude from the encapsulated sensor system 1200 and be exposed to the environment exterior to the encapsulated sensor system 1200. For example, the placement of a magnet on the exterior of the encapsulated sensor system 1200 can trigger the magnetic switch, which causes an adjustment in the behavior of the encapsulated sensor system 1200. As an example, the encapsulated sensor system 1200 can be reset if a user places a magnet near the right lower half of the front surface 1404. Placement of the magnet in this location may cause the magnetic switch to disconnect a battery on the PCB 1920. Once the magnet is removed (e.g., the user swipes the magnet away from this location), the magnetic switch causes the battery to reconnect, thereby resetting the encapsulated sensor system 1200. Upon reconnection, the encapsulated sensor system 1200 may attempt to pair or otherwise establish a connection with a relay or a router to transmit measurements via the network 120. Furthermore, a time that a magnet is placed in a certain location and/or an orientation of the magnet can cause the magnetic switch to trigger a particular function.

Figure 24:
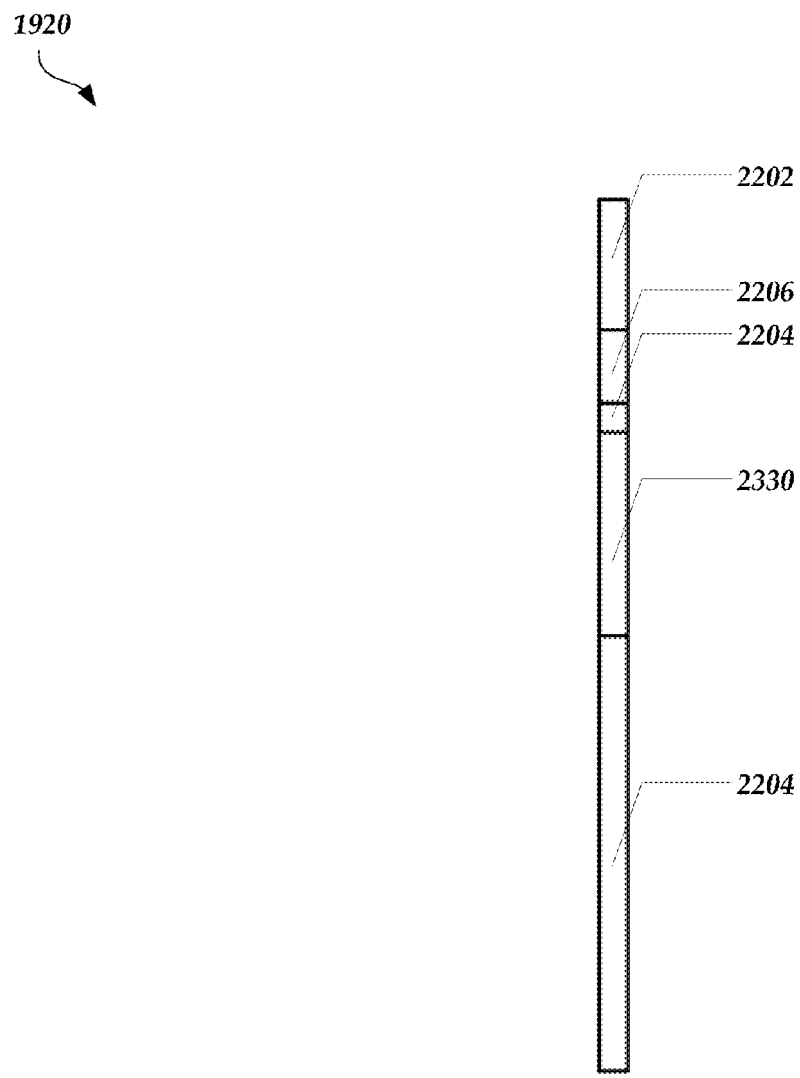
FIG. 24 illustrates a side perspective view of the PCB of FIG. 19 prior to insertion within the interior cavity of the encapsulated sensor system of FIG. 12.

FIG. 24 illustrates a side perspective view of the PCB 1920 prior to insertion within the interior cavity of the encapsulated sensor system 1200. As illustrated in FIG. 24, the PCB 1920 may maintain a uniform or nearly uniform thickness.

Figure 25:
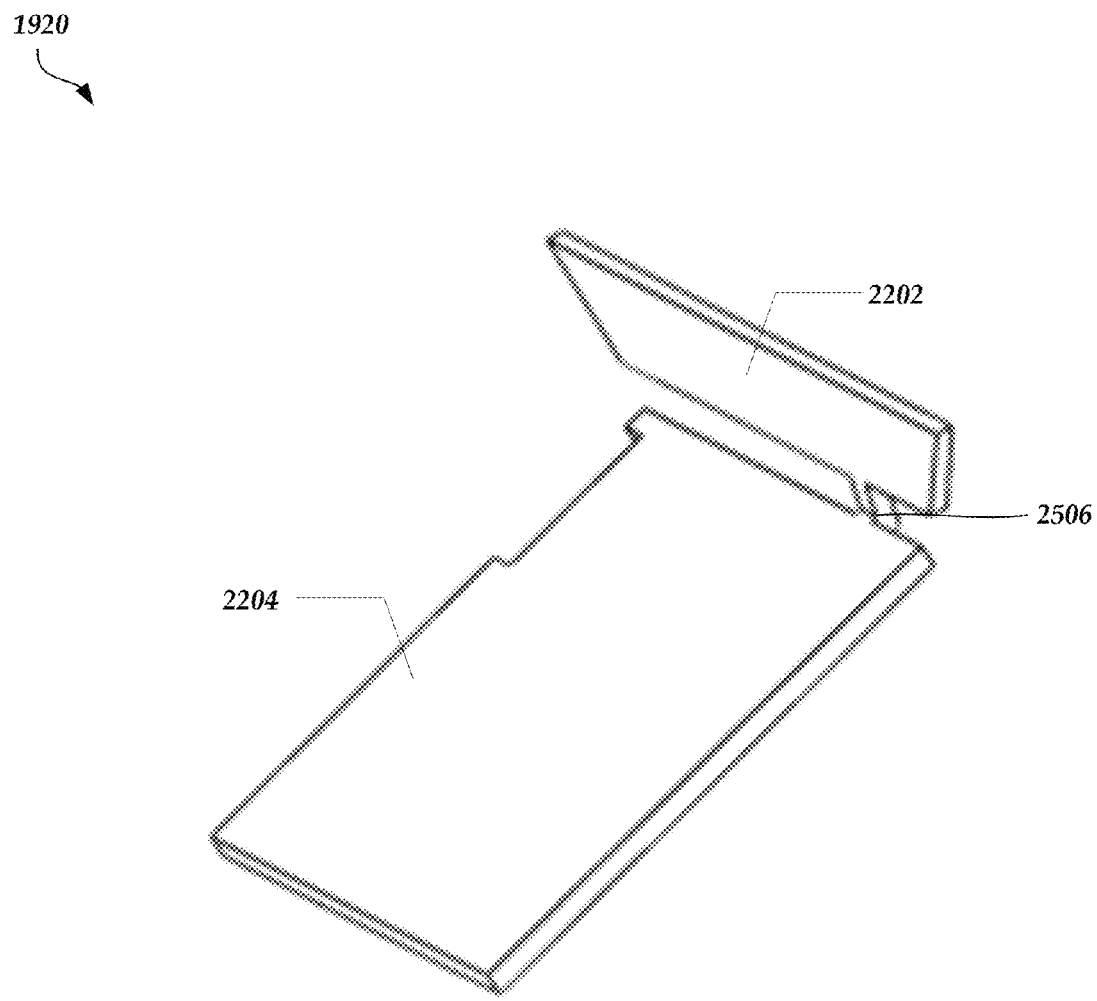
FIG. 25 illustrates a modified version of the PCB of FIG. 19.

FIG. 25 illustrates a modified version of the PCB 1920. As described above, the top and front surfaces 1408 and 1404 of the encapsulated sensor system 1200 are angled in a non-perpendicular fashion. The bottom portion 2204 of the PCB 1920 may be positioned adjacent to the interior front surface 1204 and the antenna 2202 of the PCB 1920 may be positioned adjacent to the interior top surface 1202. However, because the front surface 1404 and the top surface 1408 are not co-planar, the PCB 1920 can be bent at location 2506 to accommodate the shape of the encapsulated sensor system 1200 before insertion into the interior cavity of the encapsulated sensor system 1200, as illustrated in FIG. 25.

Figure 26:
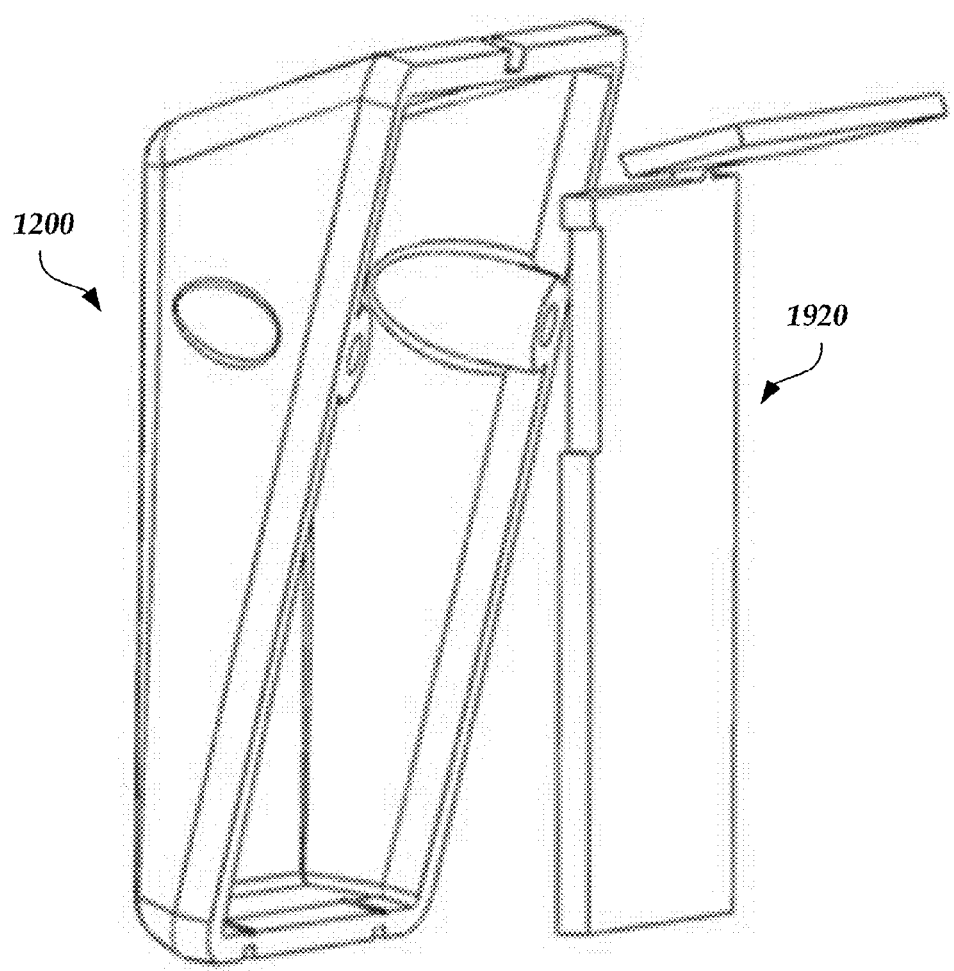
FIG. 26 illustrates a side perspective view of the modified version of the PCB of FIG. 19 and the encapsulated sensor system of FIG. 12.

FIG. 26 illustrates a side perspective view of the modified version of the PCB 1920 and the encapsulated sensor system 1200. As illustrated in FIG. 26, the PCB 1920 can be inserted into the interior cavity of the encapsulated sensor system 1200 before a back plate fully encloses the encapsulated sensor system 1200.

Figure 27:
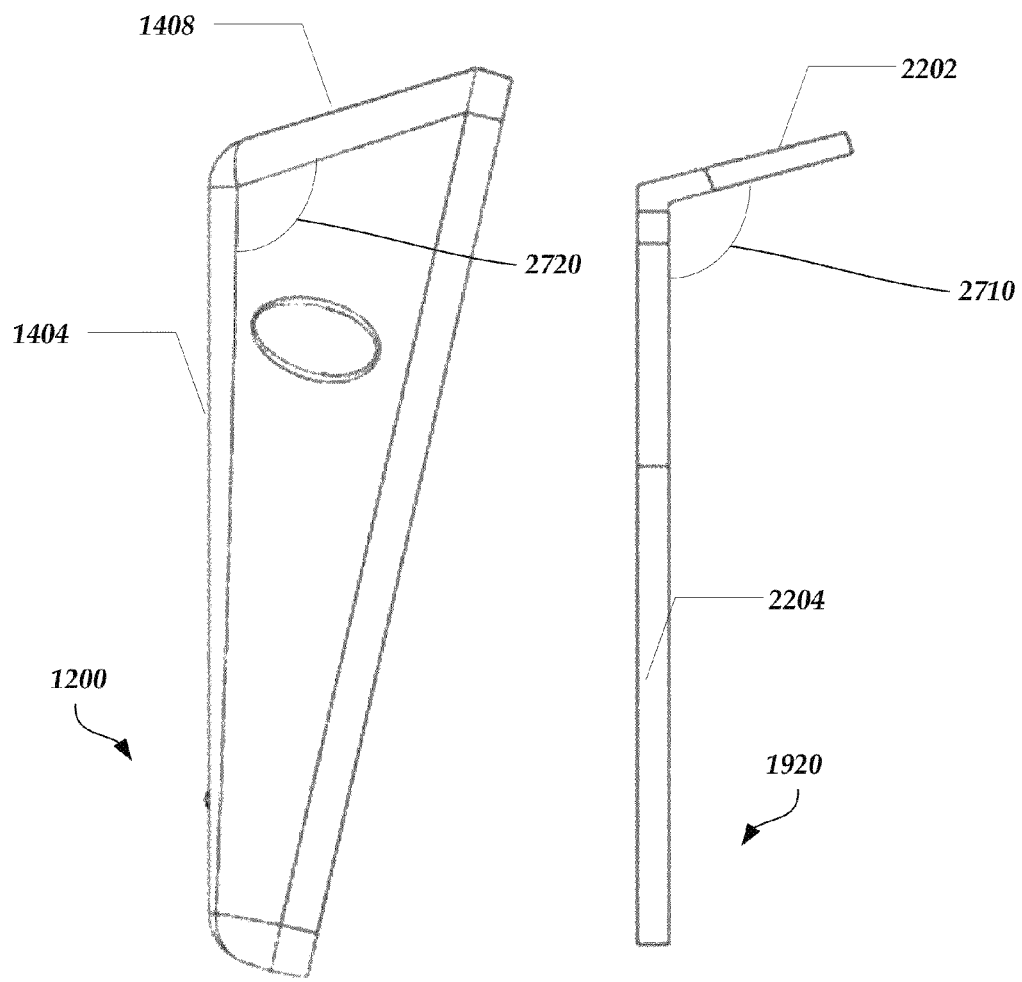
FIG. 27 illustrates another side perspective view of the modified version of the PCB of FIG. 19 and the encapsulated sensor system of FIG. 12.

FIG. 27 illustrates another side perspective view of the modified version of the PCB 1920 and the encapsulated sensor system 1200. As illustrated in FIG. 27, angle 2710 formed by the connection of the antenna 2202 to the bottom portion 2204 of the PCB 1920 is identical or nearly identical to angle 2720 formed by the top surface 1408 and the front surface 1404.

Figure 28:
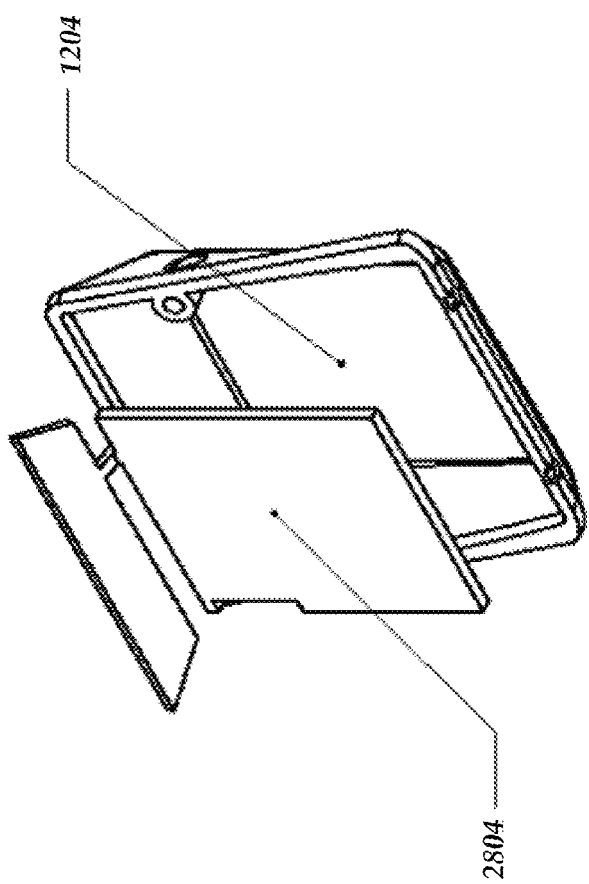
FIG. 28 illustrates a rear perspective view of the modified version of the PCB of FIG. 19 and the encapsulated sensor system of FIG. 12.

FIG. 28 illustrates a rear perspective view of the modified version of the PCB 1920 and the encapsulated sensor system 1200. As illustrated in FIG. 28, a rear surface 2804 of the PCB 1920 is opposite from a surface that abuts the interior front surface 1204 of the encapsulated sensor system 1200. The rear surface 2804 includes integrated circuits and/or other electronic components. The integrated circuits and/or other electronic components can be used to power the PCB 1920 sensors, control and measure the charge on the capacitive sensors (described below), and/or transmit data via the antenna 2202.

Figure 29:
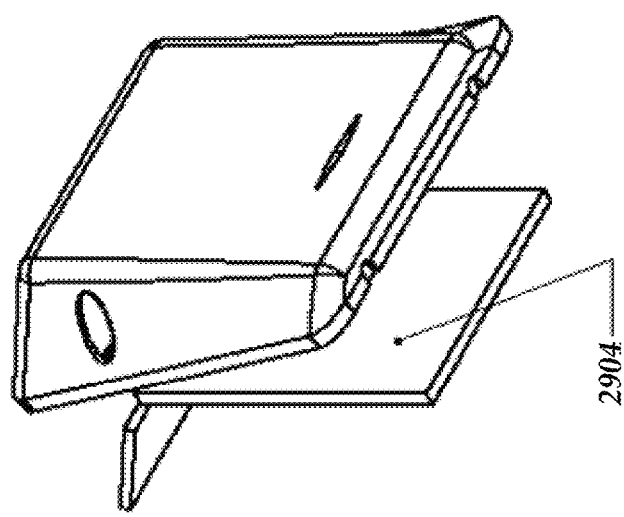
FIG. 29 illustrates a front perspective view of the modified version of the PCB of FIG. 19 and the encapsulated sensor system of FIG. 12.

FIG. 29 illustrates a front perspective view of the modified version of the PCB 1920 and the encapsulated sensor system 1200. As illustrated in FIG. 29, a front surface 2904 of the PCB 1920 abuts against the interior front surface 1204 of the encapsulated sensor system 1200. The front surface 2904 can include LEDs, photometric sensors (e.g., the photoreceiver 2322), and sensors (e.g., capacitive sensor pads) for measuring a fluid level in the environment exterior to the encapsulated sensor system 1200. The sensors may calculate an average fluid level by sampling fluid levels over a period of time (e.g., the fluid in the container may produce periodic waves and the period of time may correspond to the frequency of the waves) and transmit out the calculated average fluid level via the antenna 2202.

For example, the front surface 2904 can include a printed circuit layout of sensor pads. The printed circuit layout can be made of copper and may be a small distance away from the environment exterior to the encapsulated sensor system 1200 (e.g., 2 mm). When a portion of the front surface 1404 of the encapsulated sensor system 1200 co-planar with the sensor pads is at or below the fluid line (e.g., a height at which the fluid, such as water, interfaces with a gas, such as air), the sensor pads sense a dielectric change via a polycarbonate or other plastic material (e.g., the material of the wall of the front surface 1404, which can be 1 mm thick). As described herein, the encapsulated sensor system 1200 can transmit a message to a valve controller 132 instructing the valve controller 132 to open a valve to allow fluid to flow into a container in which the encapsulated sensor system 1200 is located if the fluid level in the container drops below a threshold level. Alternatively, the encapsulated sensor system 1200 can report the fluid level to the sensor data server 140 and the sensor data server 140 can transmit the instruction to the valve controller 132 when appropriate (e.g., the sensor data server 140 may use data measured by the encapsulated sensor system 1200 along with data measured by other sensors 112, 114, 116 to determine whether to instruct the valve controller 132 to actuate the valve). This detection of the dielectric change indicates that the fluid level is above the threshold level. The sensor pads can transmit this detection to other components in the PCB 1920 for transmission via the antenna 2202 (e.g., to the sensor data server 140). On the other hand, if no dielectric change is sensed, this can indicate that the fluid level is below the threshold level and the sensor pads can transmit an indication that no dielectric change is sensed to the other components in the PCB 1920 for transmission via the antenna 2202 (e.g., to the sensor data server 140 and/or the valve controller 132).

As described above, the valve controller 132 may actuate a valve for a set period of time. This set period of time may correlate with a specific volume of water. The sensor data server 140 can track the volume of water added to the container over a period of time.

In an embodiment, the capacitive sensors of the sensor pads are arranged in a pseudorandom manner. For example, the capacitive sensors can be any polygonal shape and do not have to be equidistant apart or the shape height and/or width. The capacitive sensors can also be located parallel with each other such that a top edge of one or more capacitive sensors is aligned or off-center from each other such that a top edge of each capacitive sensor is not aligned. An example layout of the capacitive sensors is provided in FIG. 30B, which is described below. The capacitive sensors can be sampled using a Hadamard sequence (e.g., the sequences illustrated in FIG. 2 with respect to the valves 211-213, in FIG. 3 with respect to valves 311-317, in FIG. 4 with respect to valves 411-413, etc.). For example, the capacitive sensors can be sampled in groups such that greater than 50%, but less than 100% of the capacitive sensors are sampled at each time instance (e.g., if there are 3 capacitive sensors, 2 can be sampled each time instant).

As described above, the bottom portion 2204 of the PCB 1920 is co-planar with the front surface 1404. Thus, the capacitive sensors may be located in an inclined position such that for every unit of level change of the fluid level, there may be a larger displacement along the capacitive sensor perpendicular to the fluid level. Generally, the capacitive sensors are oriented perpendicular to an expected fluid level.

Generally, as the surface area of the capacitive sensor exposed to the fluid decreases (e.g., because the fluid level has decreased), the noise produced by the capacitive sensor may increase. Noise may also be higher the further the distance is between the capacitive sensor and the fluid. Thus, each capacitive sensor may have a threshold length (e.g., as measured from one end of the sensor to the other) and be separated from the fluid by a threshold distance (e.g., represented as the thickness of the wall along the front surface 1404). The threshold length and threshold distance can be selected by using a pseudorandom sequence of orthogonal measurement sets multiplexed to a single electromotive force generator (e.g., a battery). The selected threshold length and threshold distance can provide a $\sqrt{N}/2$ improvement in measurement accuracy and an $N/2$ improvement in the SNR. As an example, the capacitive sensors can have a surface area that ranges from $0.25$ cm$^2$ to $0.75$ cm$^2$.

In some embodiments, the threshold distance can be randomized such that each capacitive sensor is a different distance from the fluid. For example, the wall along the front surface 1404 can have a varied thickness. This may provide a greater dynamic range of measurements by the capacitive sensors over a greater degree of dielectric environments.

In some embodiments, multiplexing can be used to improve the quality of the measurements by the capacitive sensors (e.g., sampling the capacitive sensors using a Hadamard sequence or encodement).

The PCB 1920 may include components to filter the raw measurements taken by the capacitive sensors based on a set of filter criteria. For example, the filtering may create a more conventional signal. The filtering may occur before the transmission of the data via the antenna 2202 to the sensor data server 140. However, in some embodiments, the raw measurements may be transmitted to the sensor data server 140 without any filtering. For example, the raw measurements may be useful in detecting anomalous features.

In an embodiment, the antenna 2202 and the bottom portion 2204 of the PCB 1920 are potted against the interior top surface 1202 and the interior front surface 1204, respectively. For example, the antenna 2202 and the bottom portion 2204 of the PCB 1920 can be potted using an epoxy resin potting material.

Figure 30A:
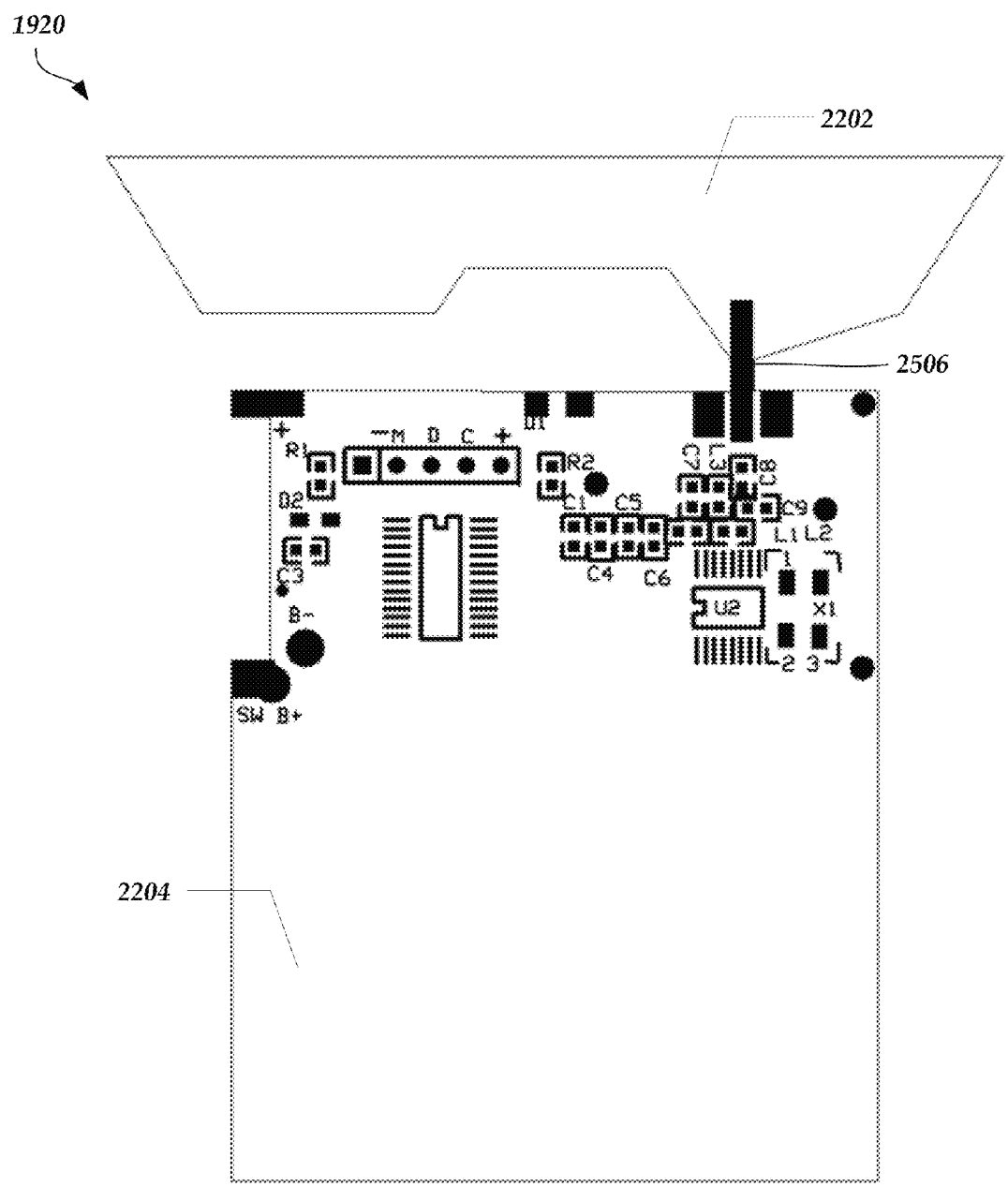
FIG. 30A illustrates a front perspective view of the components of the PCB of FIG. 19.

FIG. 30A illustrates a front perspective view of the components of the PCB 1920. As illustrated in FIG. 30A, the PCB 1920 can include various capacitors, resistors, controllers, inductors, and/or other electrical components. At the location 2506, at which the PCB 1920 bends, the portion connecting the antenna 2202 to the bottom portion 2204 (e.g., the support member 2206) can be strengthened with wire soldered onto the PCB 1920 at the location 2506.

In some embodiments, the antenna 2202 and the bottom portion 2204 of the PCB 1920 are printed separately, where the antenna 2202 or the bottom portion 2204 includes a thin strip of PCB material that extends outward from the main portion of the antenna 2202 or the bottom portion 2204. The wire soldered onto the PCB 1920 at the location 2506 can hold the antenna 2202 and the bottom portion 2204 of the PCB 1920 together and/or allow for the antenna 2202 to bend to the desired angle 2710.

Figure 30B:
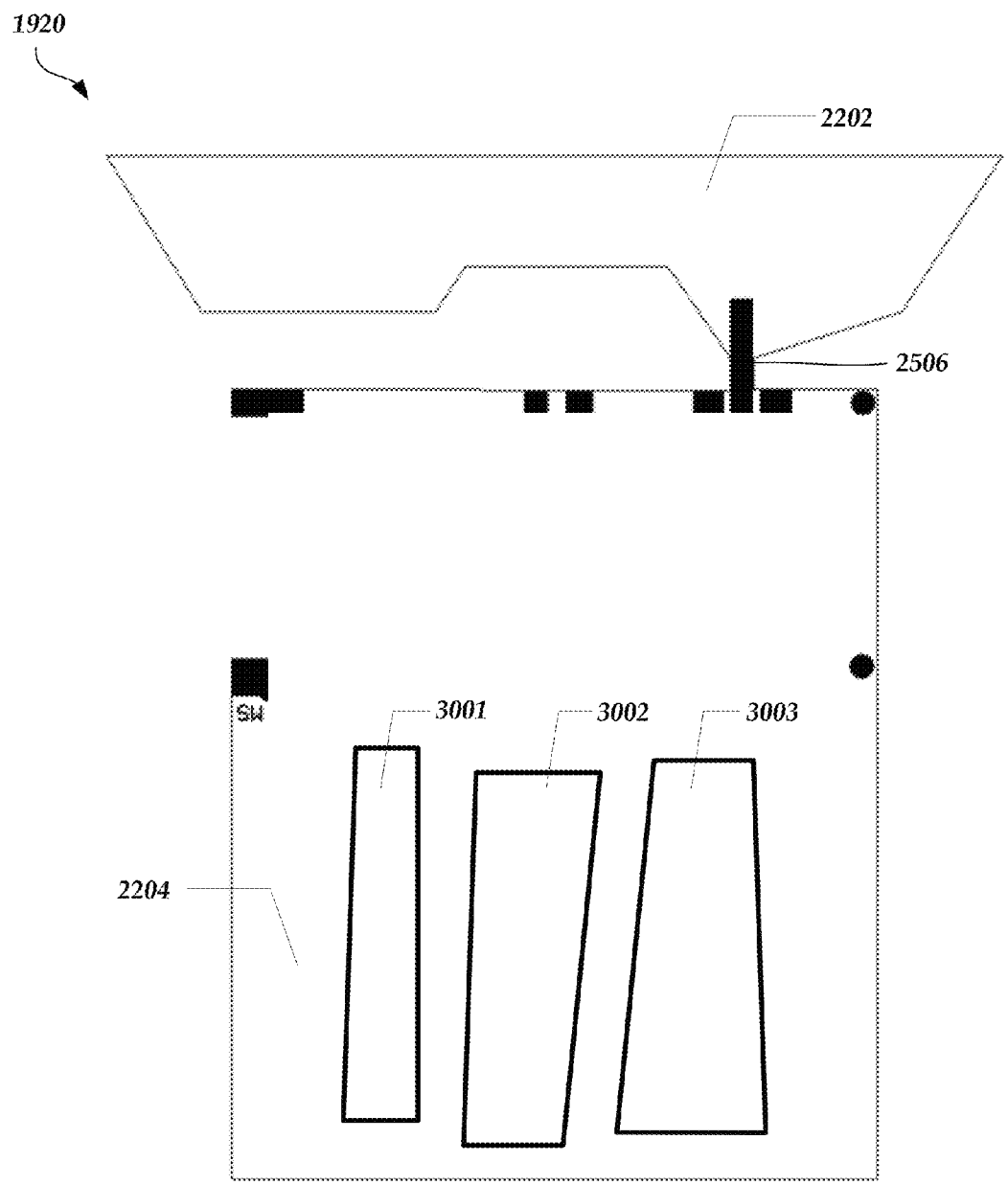
FIG. 30B illustrates a rear perspective view of the components of the PCB of FIG. 19.
Figure 31:
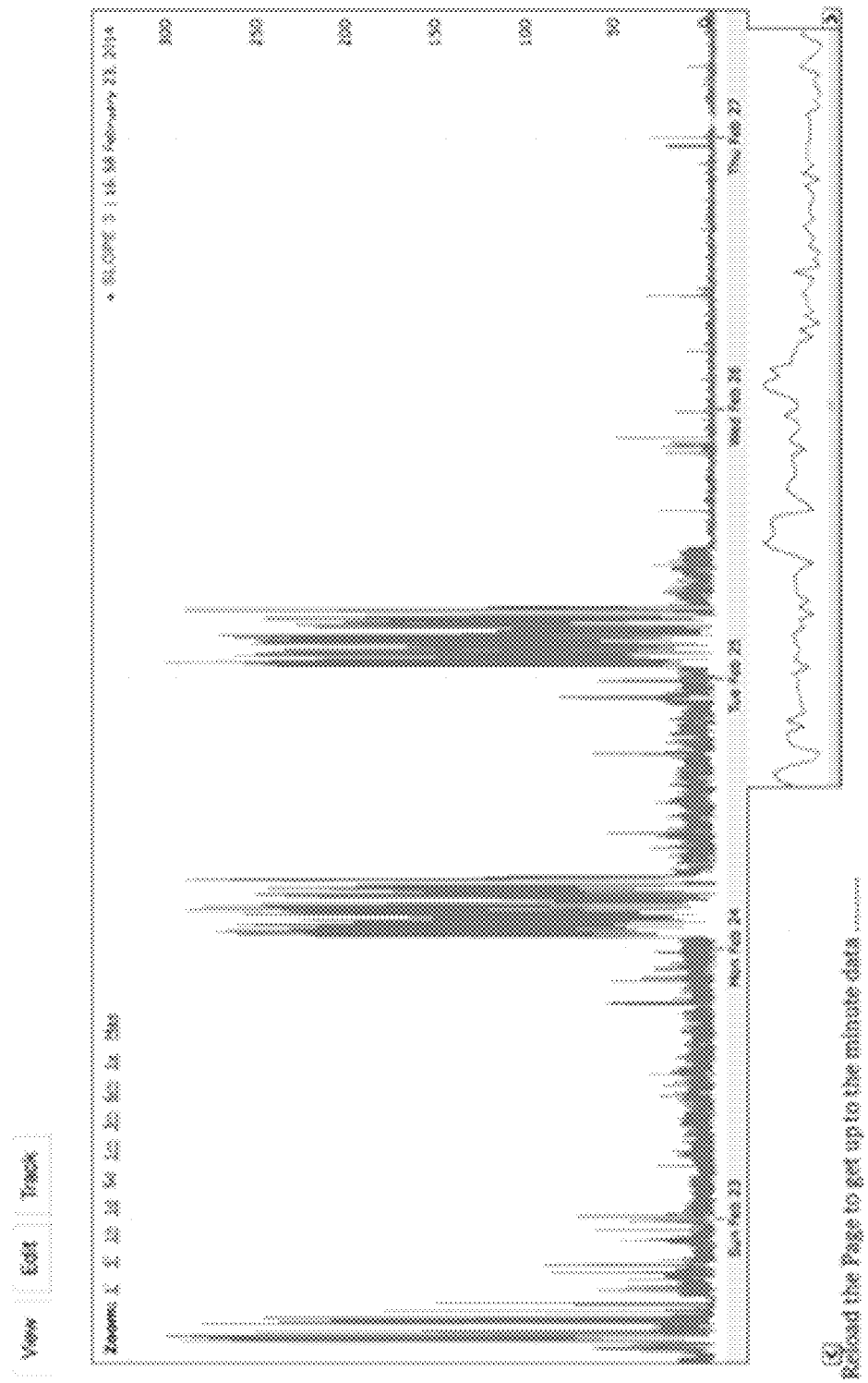
FIGS. 31-36 illustrate various graphs generated by the user interface generator for display in the user device of FIG. 1.
Figure 32:
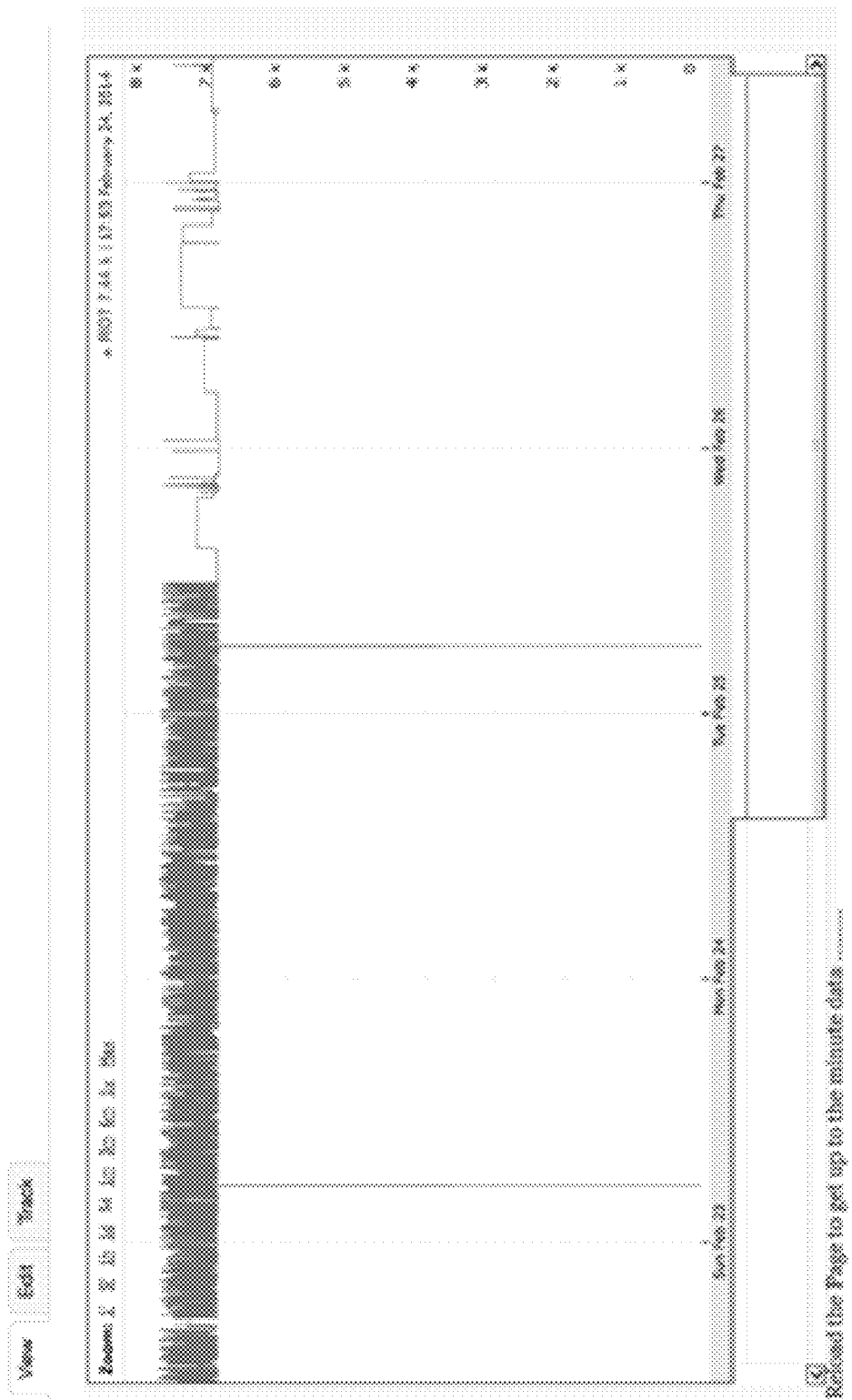

FIG. 30B illustrates a rear perspective view of the components of the PCB 1920. As illustrated in FIG. 30B, the PCB 1920 can include capacitive sensors 3001-3003. While three capacitive sensors 3001-3003 are depicted, this is for illustrative purposes only and is not meant to be limiting. The PCB 1920 can include any number of capacitive sensors and the capacitive sensors can be sampled using the Hadamard sequence described herein.

The capacitive sensors 3001-3003 can be aligned (not shown) or misaligned (shown) and can be of different shapes and/or sizes. In an embodiment, the capacitive sensors 3001-3003 are positioned in a bottom portion of the bottom portion 2204.

Water Number

Typically, pulse and digital or reed switch meters provide information on the amount of fluid flowing through pipes. For example, such meters can be used by property owners to determine an amount of water flowing through pipes. In some cases, these meters can be automatically read and the data can be transferred to a central system via a cellular network. However, such central systems can be cost-prohibitive to individual property owners or other users of a dendritic water system (e.g., apartment renters, school officials, office managers in a suite, etc.), as a contract to use the cellular network may be required. Accordingly, the devices described herein can use an existing private home network, such as an IEEE 802.11 protocol-based network (e.g., WI-FI), to relay data to the central system and thereby reduce the cost of usage.

Making such meter information accessible to individual property owners or other users of a dendritic water system can lead to more efficient water usage. However, the units of measurement (e.g., gallons in this case) may not be useful to some end users associated with one building that do not control water usage in other parts of the building (e.g., apartment renters).

Thus, the sensor data server 140 can generate customized water usage information for different end users. For example, the magnetic field sensors 114 can each be positioned near a water meter (not shown), as illustrated in FIGS. 6A-9 above. Water meters typically include a magnet that rotates along a axis longitudinal axis and an in-plane sensor that detects the north-south rotation of the magnet. Each time the north end of the magnet passes the sensor, the sensor measures a single rotation indicating that a certain volume of fluid has passed through the meter since the last time the north end of the magnet passed the sensor.

A magnetic field sensor 114 described herein is also positioned near a water meter. However, the magnetic field sensor 114 includes multi-axis sensors that detect changes in a magnetic field along three axes. Changes in the magnetic field measured by the magnetic field sensor 114 may not be correlated with any specific volume of fluid. Rather, the magnetic field sensor 114 measures the intensity (e.g., magnitude) and orientation of the magnetic field at each sampling period. This information may not correlate to an actual volume of fluid that passed through the water meter, but this information may indicate how the water meter caused the magnetic field to change as fluid passed through the water meter.

The magnetic field sensor 114 can transmit this information to the sensor data server 140 via the network 120 for storage and analysis. In particular, the predictive failure analyzer 147 can be configured to process the magnitude and orientation data received from the magnetic field sensor 114 over time to generate a value that corresponds with a speed of the change in the magnetic field over time. For example, the predictive failure analyzer 147 can perform a Fourier analysis of the magnitude and/or orientation data over time to generate a representation of this data in the frequency domain. A magnitude of the data represented in the frequency domain may indicate a speed of the change in the magnetic field at different time scales (e.g., 1 minute, 1 hour, 1 day, 1 week, etc.). This information can be useful in identifying human use patterns (e.g., the speed of the change in the magnetic field increases every 12 hours) and/or the stability of the dendritic water system (e.g., if the speed of the change in the magnetic field gradually increases over longer and longer time scales, this could indicate that a leak is present in the dendritic water system).

As an example use case, the processing performed by the predictive failure analyzer 147 may indicate that the speed of the change in the magnetic field increases between 9:00 am and 11:00 am every day except on weekends. If the magnetic field sensor 114 associated with these readings is located near a bathroom, the predictive failure analyzer 147 may identify a human use pattern—a bathroom fixture (e.g., a toilet) is used in the mornings between 9:00 am and 11:00 am on weekdays. Other human use patterns can include how many times ice is accessed from an ice maker, how many times a toilet is flushed per day, how many showers or baths are taken per day, and/or the like. Known human use patterns, which are correlated with specific sensor measurements over time or specific ranges of measurements, can be stored in the sensor data store 148. The predictive failure analyzer 147 can compare data provided by the sensors (such as the magnetic field sensor 114) with the known human use patterns to determine and/or identify a current or new human use pattern.

There are typically numerous devices coupled to the infrastructure of the dendritic water system in one of many different configurations. The characteristics of these devices may be governed by one of several environmental factors, such as the geometry of the respective device. The velocity of the flow of fluid in the dendritic water system, the pressure of the fluid, the viscosity of the fluid, and/or the demands of and/or the feedback noises from the appliances attached to the dendritic water system may work to create a particular signature of characteristics or physical attributes for a respective device that are consistent with that particular dendritic water system. These physical attributes can be correlated and/or combined by the sensor data server 140 (e.g., the predictive failure analyzer 147) with human use patterns, appliance timers based on human use patterns of appliances, and/or the like. The combined effect can produce patterns in the sensor data that can be correlated by the sensor data server 140 to human conditions. This may help utility companies or other entities reduce the cost of providing a service to end users and/or maintain a competitive advantage by reducing the cost to acquire the data necessary to identify these correlations.

The predictive failure analyzer 147 can use measurements taken by the encapsulated sensor systems 110, the acoustic sensors 112, the magnetic field sensors 114, and/or the pressure sensors 116 to generate a value indicative of a performance of the dendritic water system 150. When this value changes by a degree (e.g., if the value is an integer, a degree may be an increment or decrement of 1), the alert generator 142 can generate an alert. The alert can be transmitted to an account accessible by the user of the user device 160 (e.g., an email account), including in a user interface displayed by the user device 160, and/or transmitted to the user device 160 via the network 120 for display on the user device 160 (e.g., a text message). A user, via the user device 160, can then take an action to view the raw measurements taken by one or more sensors in the sensor system 100.

The user interface generator 144 can be configured to generate user interface data that causes a device, such as the user device 160, to display a user interface indicating the speed of the change in the magnetic field for a particular water meter, the value indicative of the performance of the dendritic water system 150, and/or any identified human use patterns or dendritic water system stability issues. The user interface data can be transmitted to the user device 160 via the network 120 for display.

In other embodiments, not shown, a display device can be mounted within the dendritic water system 150. The display device may be in communication with the network 120 and display the generated value indicative of a performance of the dendritic water system 150. Alternatively or in addition, the display device can display a number (referred to herein as a "water number") that is an index of the average water use correlation between the minute to minute flow number and the average minute to minute position number as calculated by the sensor data server 140. The water number can also be correlated with a water pressure value.

Data Graphs

Figure 33:
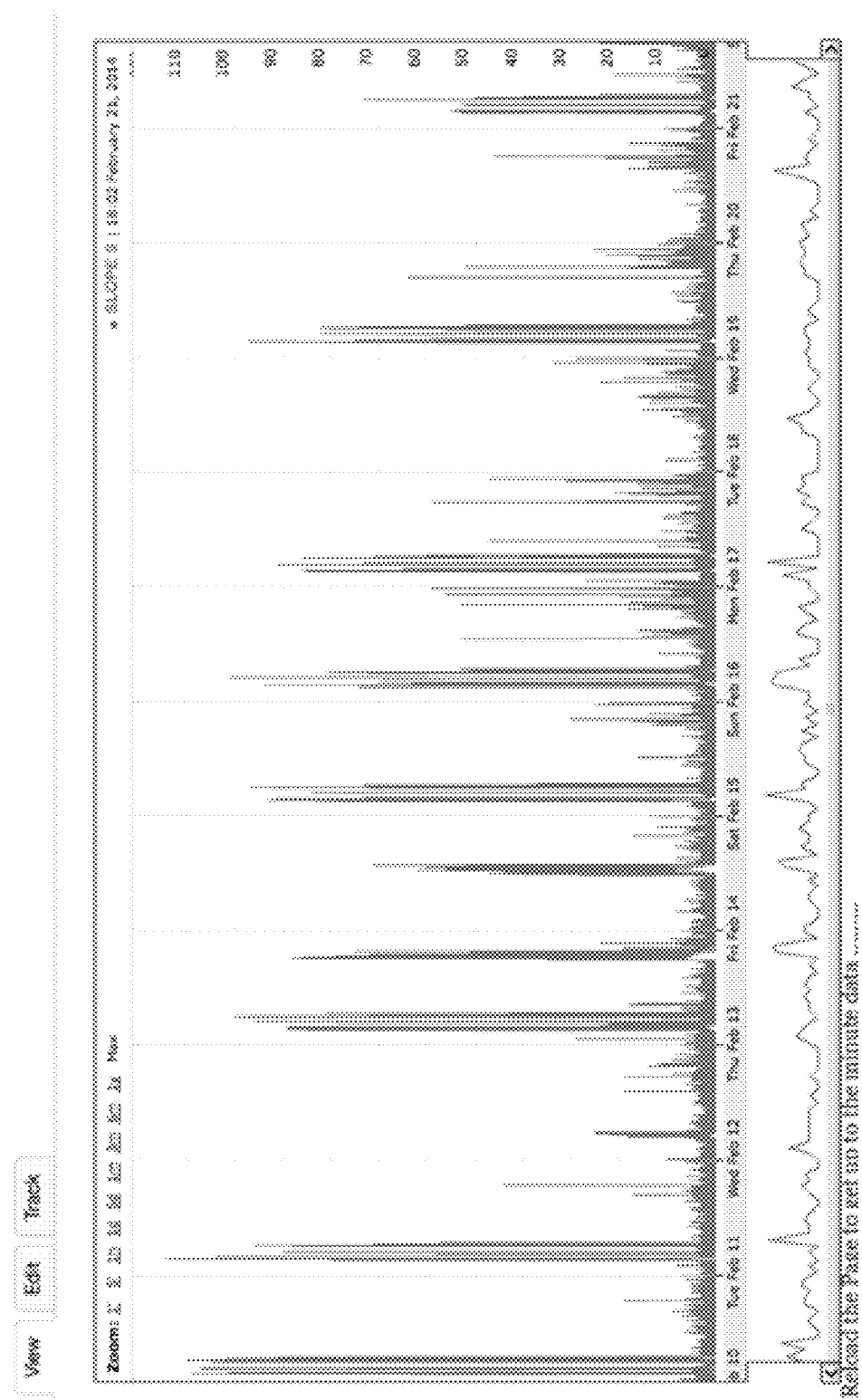
Figure 34:
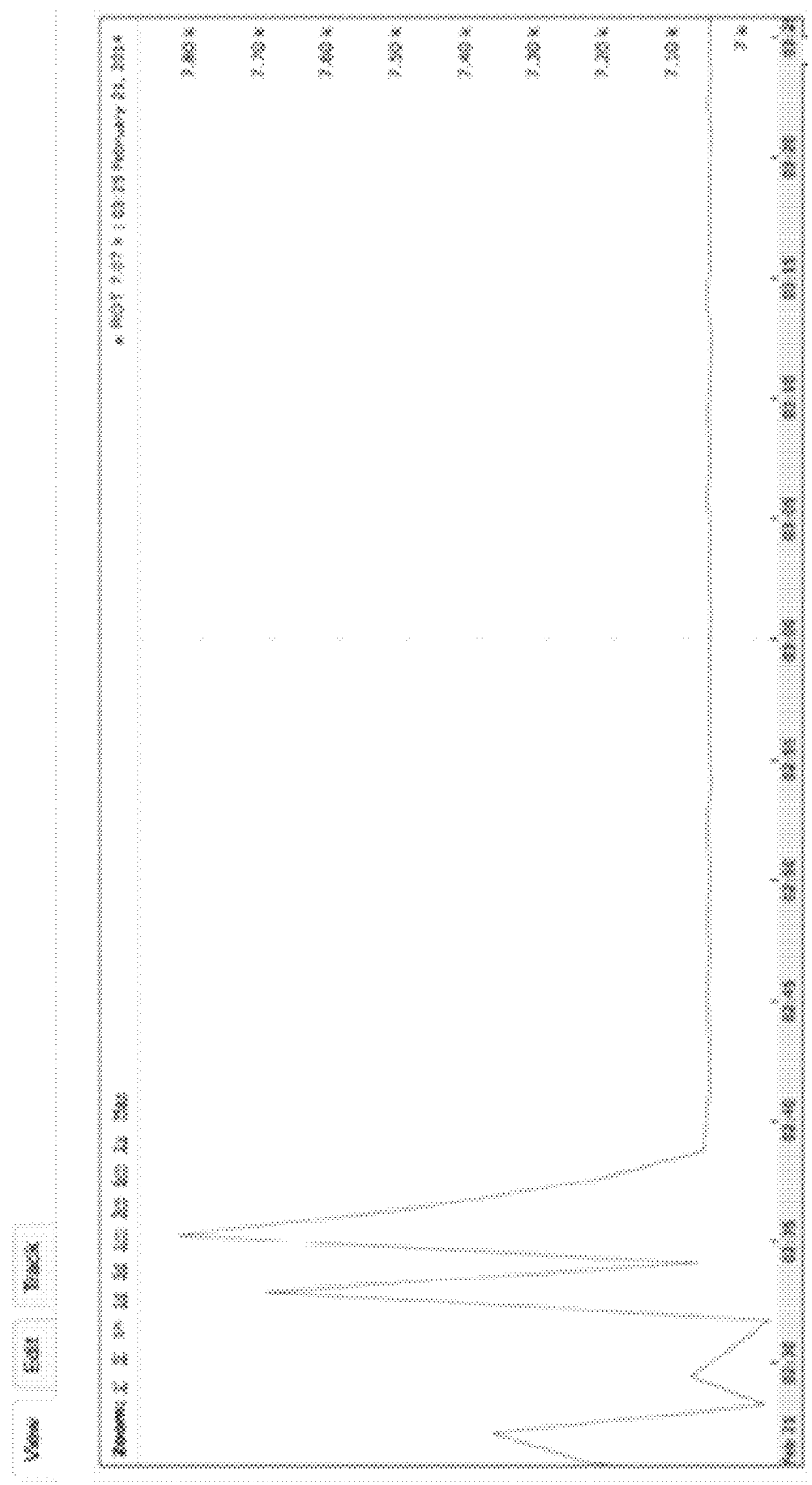
Figure 35:
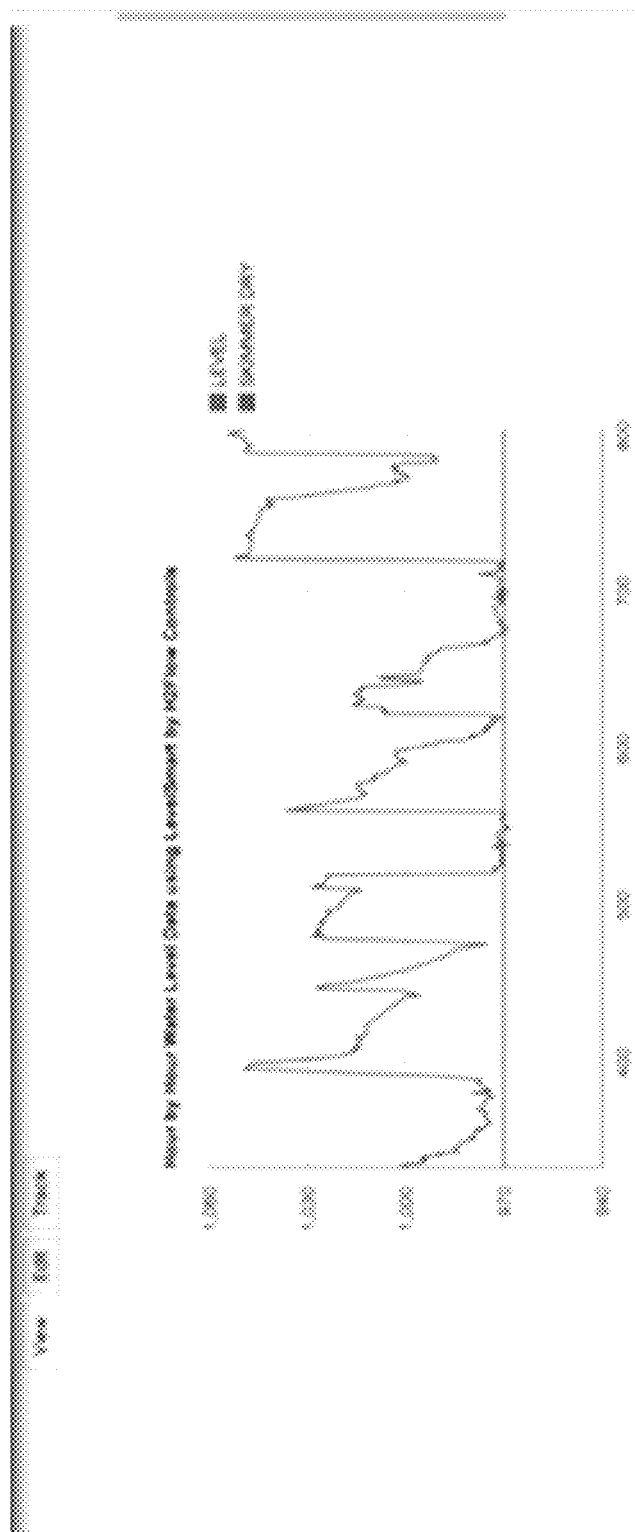
Figure 36:
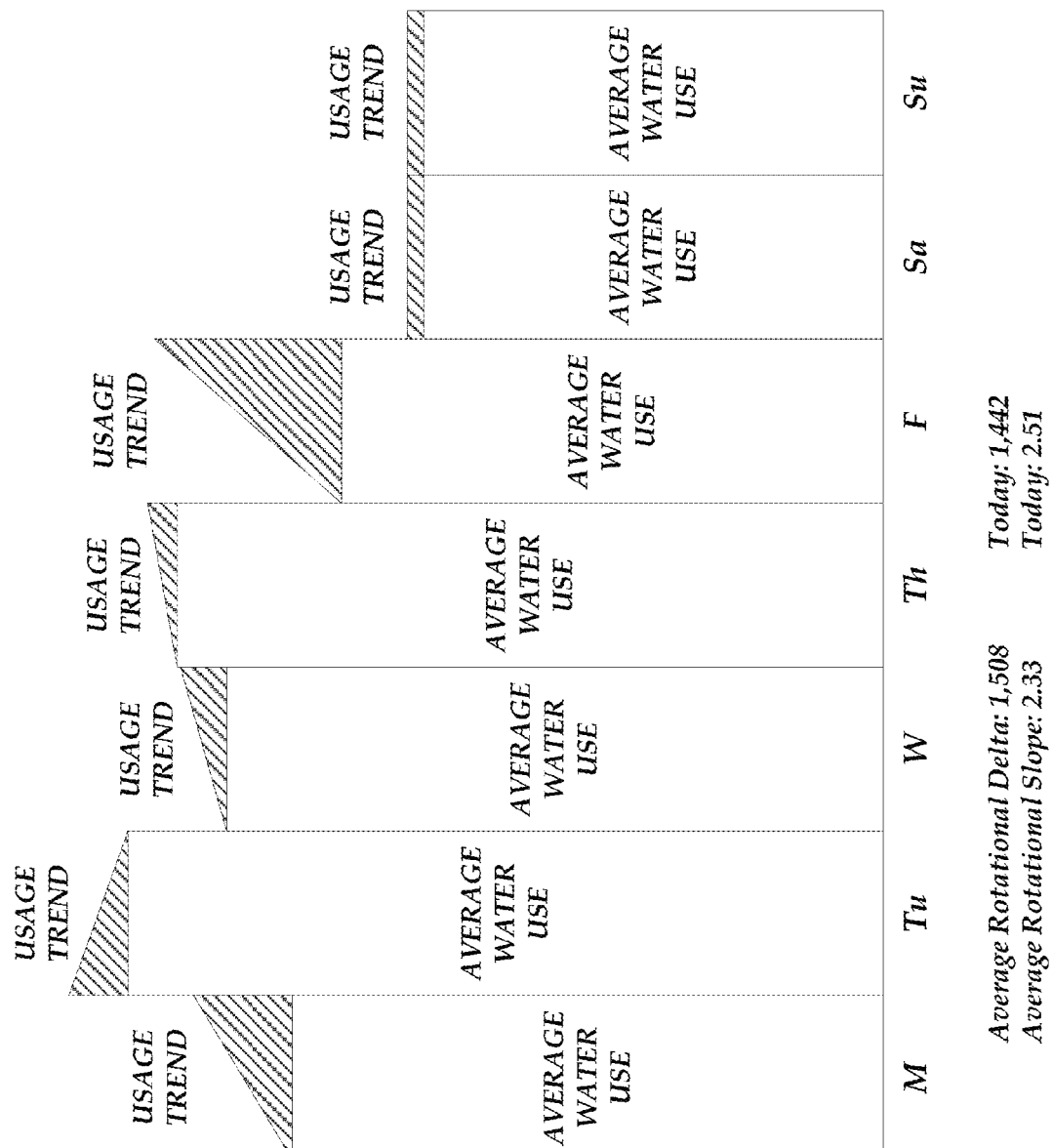

FIGS. 31-36 illustrate various graphs generated by the user interface generator 144 for display in the user device 160. Data for the graphs may be retrieved from the sensor data store 148. The graphs can depict user-defined or server-defined data. For example, a graph can plot water meter speed data (see FIG. 31), water meter movement data (e.g., the movement in one of three axes as detected by the magnetic field sensor 114, see FIG. 32), a trended plot of data over time (e.g., to visualize use patterns, which can be used to track the health of occupants given that the elderly, for example, have regular and periodic water use), water meter flow rate data (which can indicate use patterns and which can indicate a spectral distribution of amplitudes below the plotted data, see. FIG. 33), operational faults of equipment (e.g., as identified by spikes in water meter data, see FIG. 34), water levels over time (see FIG. 35), and/or human use pattern data (e.g., depicted as an average water use by day and a trend of water use by day, see FIG. 36).

The graphs can be generated based on the type of information being depicted and/or human use patterns or activities. For example, water use data can be graphed in a weekly format, where a daily average of the rotational speed in degrees per minute of the magnetic field produced by the water meter can be calculated. This daily average can then be plotted against a historical measure of the same value from a corresponding date (e.g., from the same day in the previous week, in the previous month, in the previous year, etc.). As another example, a sprinkler system may be configured to turn on three days a week. The graphs can be generated such that only data from these three days is plotted. As another example, the sensor data server 140 can determine the best method for displaying data based on data patterns of the dendritic water system 150.

The user interface generator 144 can also instruct the alert generator 142 to generate an alert based on the generated graph data. For example, if a trended plot graph shows that water use was stable for an individual, but then suddenly drops, this could indicate an issue with the individual's health. An alert can then be generated to notify a user of a potential health issue.

TERMINOLOGY

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry. The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating or otherwise vexing to user.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A magnetic field sensor, comprising:
   a head comprising a first sensor, a second sensor, and a third sensor, wherein the first sensor is oriented to measure a magnetic field generated by a water meter along a first axis, wherein the second sensor is oriented to measure the magnetic field along a second axis different from the first axis, wherein the third sensor is oriented to measure the magnetic field along a third axis different from the first axis and the second axis, and wherein the head is positioned a first distance from the water meter;
   a cable comprising a first end and a second end, wherein the first end of the cable is coupled with the head, wherein the cable is configured to receive a first measurement measured by the first sensor, a second measurement measured by the second sensor, and a third measurement measured by the third sensor, and wherein the cable is further configured to transport the first measurement, the second measurement, and the third measurement to the second end of the cable; and
   a transceiver coupled to the second end of the cable, wherein the transceiver is configured to wirelessly transmit the first measurement, the second measurement, and the third measurement received from the second end of the cable to a remote server over a network.

2. The magnetic field sensor of claim 1, wherein a front surface of the head is positioned the first distance from the water meter.

3. The magnetic field sensor of claim 1, wherein a left surface of the head is positioned the first distance from the water meter.

4. The magnetic field sensor of claim 1, wherein the water meter comprises a magnet that rotates about a first axis, and wherein the head is positioned in a plane that is generally transverse to the first axis.

5. The magnetic field sensor of claim 4, wherein the third sensor measures a rate of change of a magnetic field generated by the magnet in the water meter along the third axis, and wherein a faulty meter is detected if the rate of the change of the magnetic field generated by the magnet in the water meter along the third axis is greater than a threshold value.

6. The magnetic field sensor of claim 1, wherein the first sensor is a hall-effect sensor.

7. The magnetic field sensor of claim 1, wherein the first sensor is positioned in a first plane, and wherein the head further comprises a ferrite pole positioned in a second plane co-planar with the first plane.

8. The magnetic field sensor of claim 7, wherein the first plane is positioned above the second plane.

9. The magnetic field sensor of claim 7, wherein the first plane is positioned below the second plane.

10. The magnetic field sensor of claim 1, wherein the head further comprises an amplifier configured to amplify the first measurement measured by the first sensor.

11. The magnetic field sensor of claim 10, wherein the head further comprises an analog-to-digital circuit (ADC) configured to digitize the amplified first measurement, and wherein the ADC is further configured to transmit the digitized amplified first measurement to the first end of the cable.

12. The magnetic field sensor of claim 1, wherein the first sensor is configured to measure a rate of change of the magnetic field generated by the water meter along the first axis, and wherein the second sensor is configured to measure a rate of change of the magnetic field generated by the water meter along the second axis.

13. The magnetic field sensor of claim 1, wherein the head comprises a protective enclosure that protects the first sensor, the second sensor, and the third sensor from an environment exterior to the head.

14. The magnetic field sensor of claim 1, wherein a top of the head comprises a first depression for coupling the device with a pipe using a mounting component.

15. The magnetic field sensor of claim 14, wherein the mounting component is a plastic tie.

16. The magnetic field sensor of claim 1, further comprising a temperature sensor configured to measure a current temperature.

17. The magnetic field sensor of claim 16, wherein the head further comprises a microcontroller configured to adjust the first measurement measured by the first sensor based on the measured current temperature.

18. A magnetic field sensor, comprising:
   a head comprising a multi-axis sensor, wherein the multi-axis sensor is configured to measure a change in a magnetic field generated by a fluid meter along a first axis, along a second axis that is different from the first axis, and along a third axis that is different from the first axis and the second axis, and wherein the head is positioned a first distance from the fluid meter;
   a cable comprising a first end and a second end, wherein the first end of the cable is coupled with the head, wherein the cable is configured to receive a first measurement measured by the multi-axis sensor, and wherein the cable is further configured to transport the first measurement to the second end of the cable; and
   a transceiver coupled to the second end of the cable, wherein the transceiver is configured to associate with a network and transmit the first measurement received from the second end of the cable to a remote server via the network.

19. The magnetic field sensor of claim 18, wherein the multi-axis sensor is further configured to measure a magnitude of the magnetic field generated by the fluid meter and an orientation of the magnetic field generated by the fluid meter.

20. The magnetic field sensor of claim 18, wherein the fluid meter comprises one of a liquid meter used to measures a rate of flow of a liquid through a fixed location or a gas meter used to measure a rate of flow of a gas through the fixed location.

* * * * *